United States Patent
Kim et al.

[11] Patent Number: 5,461,024
[45] Date of Patent: Oct. 24, 1995

[54] THIOPHENESULFONYLUREA DERIVATIVES

[75] Inventors: Dae-Whang Kim; Dong Ju Jeon, both of Daejeon; Sang Soon Park, Chungchongbuk-do; Jae Chun Woo; Tae Jun Kim, both of Daejeon, all of Rep. of Korea

[73] Assignee: Korea Research Institute of Chemical Technology, Daejeon, Rep. of Korea

[21] Appl. No.: 117,011

[22] PCT Filed: Mar. 14, 1992

[86] PCT No.: PCT/KR92/00009

§ 371 Date: Dec. 9, 1993

§ 102(e) Date: Dec. 9, 1993

[87] PCT Pub. No.: WO92/16525

PCT Pub. Date: Oct. 1, 1992

[30] Foreign Application Priority Data

Mar. 14, 1991 [KR] Rep. of Korea ............ 91-4063

[51] Int. Cl.$^6$ ............ C07D 409/12; C07D 409/14; A01N 43/66
[52] U.S. Cl. ............ 504/213; 544/113; 544/198; 544/207; 544/209; 544/212; 544/219
[58] Field of Search ............ 504/213; 544/113, 544/198, 207, 209, 212, 219

OTHER PUBLICATIONS

Kimura et al, Chemical Abstracts, vol. 104, entry 186457 (1986).

*Primary Examiner*—John M. Ford
*Attorney, Agent, or Firm*—Kenyon & Kenyon

[57] ABSTRACT

A novel thiophenesulfonylurea derivative having herbicidal activity, having the formula (I):

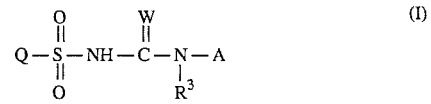

wherein the substituents are herein described.

11 Claims, No Drawings

THIOPHENESULFONYLUREA DERIVATIVES

TECHNICAL FIELD

The present invention relates to novel thiophenesulfonylurea derivatives having agriculturally suitable for herbicidal activity.

BACKGROUND OF THE INVENTION

It is publicly well known that sulfonylurea derivatives have a herbicidal activity. Here are the formulas for the sulfonylureas.

1) U.S. Pat. No. 4,370,480 discloses the compound having the following formula

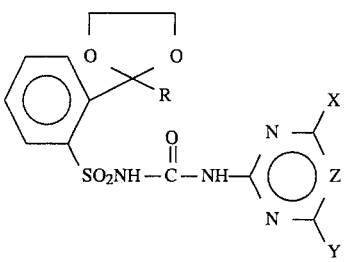

wherein,

R is H, alkyl, alkenyl, alkynyl or alkyl substituted with 1~4 of F, Cl, Br, $OCH_3$, CN or $CO_2R^1$, alkenyl substituted with 1~3 atoms of Cl, cycloalkyl, cycloalkenyl, cycloalkyl substituted with $CH_3$, $CH_2CH_3$, Cl, $OCH_3$, etc. or $CO_2R^1$;

X is H, Cl, $CH_3$, $OCH_3$, etc.;

Y is H, Cl, $C_1$–$C_4$ of alkyl, halogen, alkoxy or alkyl substituted with CN, etc.;

Z is CH.

2) U.S. Pat. No. 4,786,314 discloses the compound having the following formula

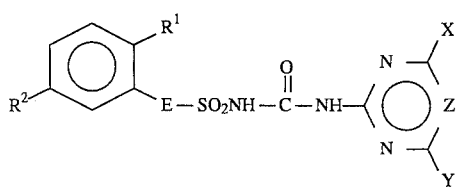

wherein, $R^1$ is alkyl, alkenyl, halogen, $NO_2$, haloalkenyl, alkynyl, haloalkynyl, alkoxy, haloalkoxy, alkoxyalkyl,

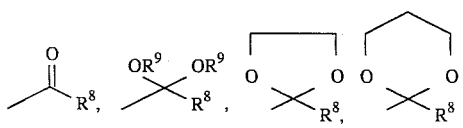

etc.;

$R^2$ is

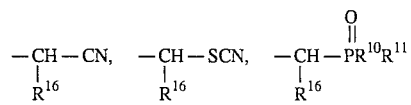

etc.;

$R^8$ is H, $C_1$–$C_4$ alkyl, alkenyl, alkynyl, $CH_2CH_2Cl$, $CH_2CH_2F$, $C_1$–$C_2$ alkyl substituted with OMe or SMe, or cycloalkyl.

3) U.S. Pat. No. 4,612,035 discloses the compound having the following formula

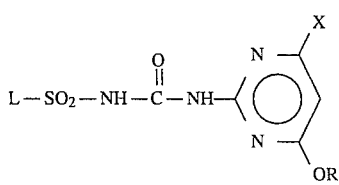

wherein,

L is phenyl, naphthyl, pyridine or thiophene having substitutent;

$R^1$ is

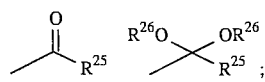

$R^{25}$ is H or alkyl;

$R^{26}$ is alkyl.

4) U.S. Pat. No. 4,659,369 discloses the compound having the following formula

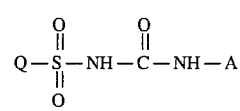

wherein,

Q is Q-1, Q-2, Q-3 or Q-4 as followings.

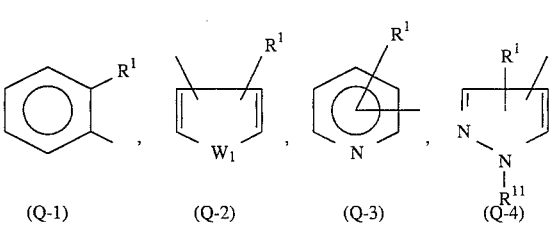

and then, $R^1$ is

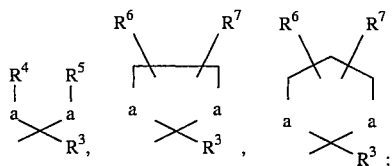

R³ is H, $C_1$–$C_3$ of alkyl or $C_1$–$C_3$ of alkoxy;
R⁴ and R⁵ are respectively $C_1$–$C_2$ of alkyl;
R⁶ and R⁷ are respectively H or $C_1$–$C_2$ of alkyl;
a is O, S or $NCH_3$;
$W_1$ is O or s;
A is

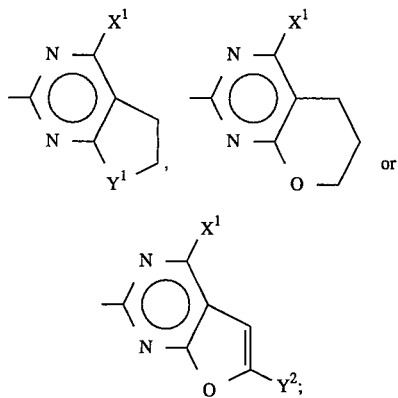

wherein, $X^1$ is $CH_3$, $OCH_3$, OEt or $OCHF_2$; $Y^1$ is O or $CH_2$; $Y^2$ is H or $CH_3$.

5) Japanes Patent Laid-Opened So 61-22083 discloses the compound having the following formula

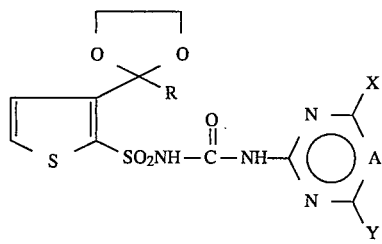

wherein,
R is H or alkyl group;
X and Y are respectively methyl or methoxy group;
A is N or CH.

As the above patents, many sulfonylurea herbicides have been known until recently.

Even with these herbicides, more and more weeds develop immunity forwards these herbicides and cause undesirable vegetations. Thus, continuous research is in demand to develop more effective and newer for a good harvest.

Therefore, the object of the present invention is to provide new thiophenesulfonylurea derivatives having a very prominent herbicidal activity with a good selectivity for various vegetations and agriculturally suitable herbicides for treatment of pre-emergence and/or post-emergence or plant growth regulants.

SUMMARY OF THE INVENTION

The present invention relates to novel thiophenesulfonylurea derivatives having the following general formula (I)

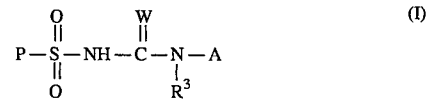

wherein,

P is P-1, P-2 or P-3 as followings

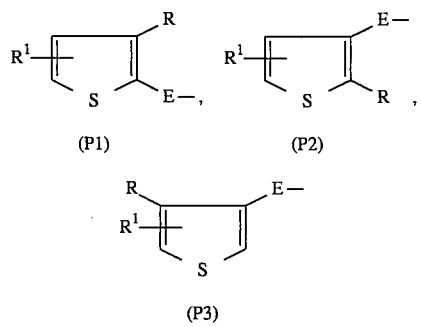

wherein,

R¹ is H, $C_1$–$C_3$ alkyl, $C_1$–$C_3$ haloalkyl, halogen, CN, $NO_2$, $C_1$–$C_3$ alkoxy, $C_1$–$C_3$ haloalkoxy, $SO_2NR'R''$, $C_1$–$C_3$ alkylthio, $C_1$–$C_3$ alkylsulfinyl, $C_1$–$C_3$ alkylsulfonyl, $SCHF_2$, $NH_2$, $NHCH_3$, $N(Me)_2$, $C_1$–$C_2$ alkyl substituted with $C_1$–$C_2$ alkoxy, $C_1$–$C_4$ haloalkoxy, SH, $SCH_3$, CN or OH; or $CO_2R'''$; and then R¹ is H, $C_1$–$C_4$ alkyl, $C_2$–$C_3$ cyanoalkyl, methoxy or ethoxy; R'' is H, $C_1$–$C_4$ alkyl, $C_3$–$C_4$ alkenyl, or when taken together connecting R' and R'', —$(CH_2)_3$—, —$(CH_2)_4$—, —$(CH_2)_5$— or $CH_2CH_2OCH_2CH_2$—, may be formed; R''' is $C_1$–$C_4$ alkyl, $C_3$–$C_4$ alkenyl, $C_3$–$C_4$ alkynyl, $C_1$–$C_4$ alkyl substituted with 1~3 halogens or cyano groups, $C_5$–$C_6$ cycloalkyl, $C_4$–$C_7$ cycloalkylalkyl or $C_2$–$C_4$ alkoxyalkyl;

R is

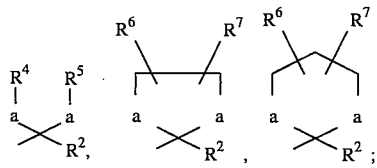

wherein, a is O or S; $R^2$ is $C_1$–$C_6$ alkyl substituted with 1~3 halogens; R⁴ and R⁵ are respectively $C_1$–$C_4$ of alkyl; and R⁶ and R⁷ are respectively H, $C_1$–$C_3$ alkyl or $C_1$–$C_3$ haloalkyl;

E is $CH_2$ single bond;

R³ is H or $CH_3$;

W is O or S;

A is A1, A2, A3, A4, A5, A6 or A7 as followings;

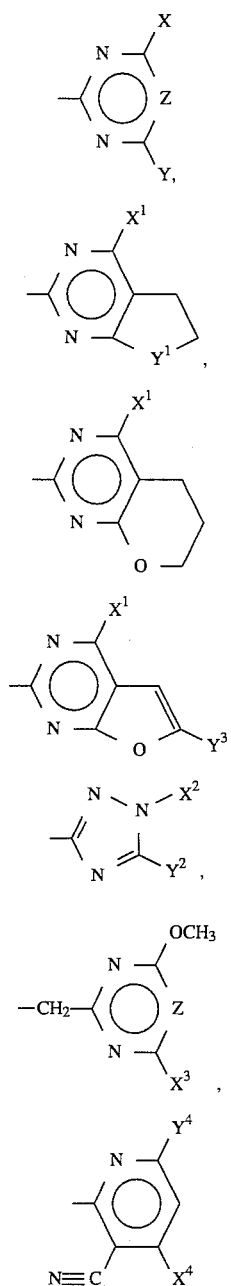

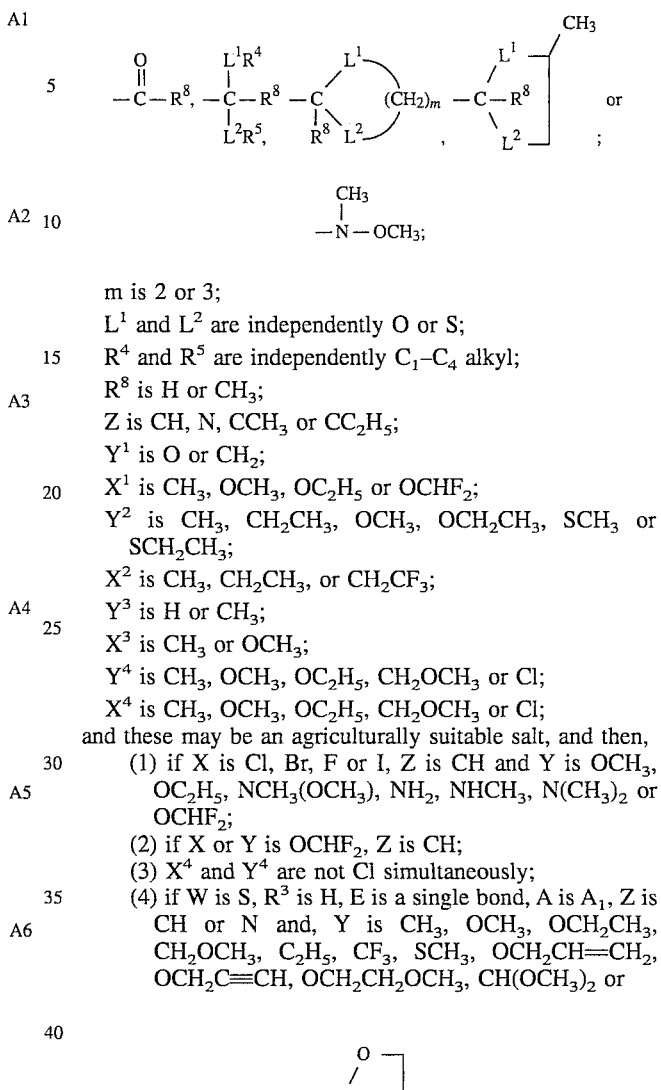

wherein,

X is H, $C_1$–$C_4$ alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, halogen, $C_2$–$C_5$ alkoxyalkyl, $C_2$–$C_5$ alkoxyalkoxy, amino, $C_1$–$C_3$ alkylamino, di($C_1$–$C_3$ alkyl) amino or $C_3$–$C_5$ cycloalkyl:

Y is H, $C_1$–$C_4$ alkyl, $C_1$–$C_4$ alkoxy, $C_1$–$C_4$ haloalkoxy, $C_1$–$C_4$ haloakylthio, $C_1$–$C_4$ alkylthio, $C_2$–$C_5$ alkoxyalkyl, $C_2$–$C_5$ alkoxyalkoxy, amino, $C_1$–$C_3$ alkylamino, di($C_1$–$C_3$ alkyl)amino, $C_3$–$C_4$ alkenyloxy, $C_3$–$C_4$ alkynyloxy, $C_2$–$C_5$ alkylthioalkyl, $C_1$–$C_4$ haloalkyl, $C_2$–$C_4$ alkynyl, azido, cyano, $C_2$–$C_5$ alkylsulfinylalkyl, $C_2$–$C_5$ alkylsulfonylalkyl, $CH_2OH$, $C_3$–$C_5$ cycloalkyl, $C_3$–$C_5$ cycloalkoxy, $C_2$–$C_5$ alkylthioalkoxy, m is 2 or 3;

$L^1$ and $L^2$ are independently O or S;

$R^4$ and $R^5$ are independently $C_1$–$C_4$ alkyl;

$R^8$ is H or $CH_3$;

Z is CH, N, $CCH_3$ or $CC_2H_5$;

$Y^1$ is O or $CH_2$;

$X^1$ is $CH_3$, $OCH_3$, $OC_2H_5$ or $OCHF_2$;

$Y^2$ is $CH_3$, $CH_2CH_3$, $OCH_3$, $OCH_2CH_3$, $SCH_3$ or $SCH_2CH_3$;

$X^2$ is $CH_3$, $CH_2CH_3$, or $CH_2CF_3$;

$Y^3$ is H or $CH_3$;

$X^3$ is $CH_3$ or $OCH_3$;

$Y^4$ is $CH_3$, $OCH_3$, $OC_2H_5$, $CH_2OCH_3$ or Cl;

$X^4$ is $CH_3$, $OCH_3$, $OC_2H_5$, $CH_2OCH_3$ or Cl;

and these may be an agriculturally suitable salt, and then, (1) if X is Cl, Br, F or I, Z is CH and Y is $OCH_3$, $OC_2H_5$, $NCH_3(OCH_3)$, $NH_2$, $NHCH_3$, $N(CH_3)_2$ or $OCHF_2$;

(2) if X or Y is $OCHF_2$, Z is CH;

(3) $X^4$ and $Y^4$ are not Cl simultaneously;

(4) if W is S, $R^3$ is H, E is a single bond, A is $A_1$, Z is CH or N and, Y is $CH_3$, $OCH_3$, $OCH_2CH_3$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or (5) if a number of total carbon atoms of X and Y is more than 4, a number of carbon atoms of $R^2$ is 4 or less than 4.

DETAILED DESCRIPTION OF THE INVENTION

Among the definitions according to the present invention, the following terms have the following meanings:

a) "Alkyl" used ether alone or in compound word such as "alkylthio" or "haloalkyl" etc. denotes straight chain or branched alkyls such as methyl, ethyl, n-propyl, isopropyl or buthyl isomers.

b) "Alkoxy" denotes methoxy, ethoxy, n-propoxy, isopropoxy or butoxy isomers.

c) "Alkenyl" denotes straight chain or branched alkenes, for example, vinyl, 1-propenyl, 2-propenyl or butenyl, pentenyl, hexenyl or heptenyl isomers etc.

d) "Alkynyl" denotes straight chain or branched alkynyl such as ethynyl, 1-propynyl, 2-propynyl, or butynyl, pentynyl or hexynyl isomers.

e) "Halogen" used ether alone or in compound word "halo" denotes chlorine, fluorine, bromine or Iodine.

A preferred group of thiophenesulfonylurea derivatives having the formula(I) shown as the below, in view of easiness of synthesis and herbicidal activity, wherein (1) $R^3$ is H; W is O; and E is single bond;

(2) $R^1$ is H, F, Cl, $C_1$–$C_2$ alkyl, $C_1$–$C_2$ haloalkyl, $C_{1–C2}$ alkoxy, $C_1$–$C_2$ haloalkoxy, $C_1$–$C_2$ alkylthio, $CH_2OCH_3$, OR $CH_2SCH_3$;

(3) X is $CH_3$, $OCH_3$, $OCH_2CH_3$, Cl, F, Br, $OCHF_2$, $CH_2F$, $OCH_2CH_2F$, $OCH_2CHF_2$, $OCH_2CF_3$, $CF_3$, $CH_2Cl$ or $CH_2Br$; Y is H, $C_1$–$C_3$ alkyl, $OCH_3$, $OCH_2CH_3$, $CH_2OCH_3$, $NHCH_3$, $NCH_3(OCH_3)$, $N(CH_3)_2$, $CF_3$, $SCH_3$, $OCH_2CH=CH_2$, $OCH_2C\equiv CH$, $CH_2OC_2H_5$, $OCH_2CH_2OCH_3$, $CH_2SCH_3$, $OCHF_2$, $SCHF_2$, cyclopropyl, $C\equiv CH$, or $C\equiv C-CH_3$;

(4) $R^2$ is $CH_2F$, $CHF_2$, $CHFCl$, $CH_2Cl$, $CH_2Br$, $CHFCH_3$, $CH_2CH_2F$, $CH_2CH_2CH_2F$, $CH_2CH_2Cl$, $CHClCH_3$, $CHCl_2$, $CHFCH_2F$, $CHClCH_2Cl$, $CHFCH_2Cl$, $CH_2CF_3$ or $CF(CH_3)_2$;

(5) A is $A_1$; X is $CH_3$, $OCH_3$, $OCH_2CH_3$, Cl or $OCHF_2$; Y is $CH_3$, $C_2H_5$, $OCH_3$, $CH_2OCH_3$, $CH(OCH_3)_2$, $OCHF_2$, $NHCH_3$, $N(Me)_2$ or cyclopropyl, and $R^1$ is H, $CH_3$ or $OCH_3$.

The novel compounds having the above formula(I) according to the present invention have a very strong herbicide activity and good selectivity for a useful vegetation.

The compounds of the present invention can be prepared by reactions as described in herein below.

The compounds of general formula(I) can be obtained by reacting the compounds having the following formula(II) with an amine compound of the following formula(III).

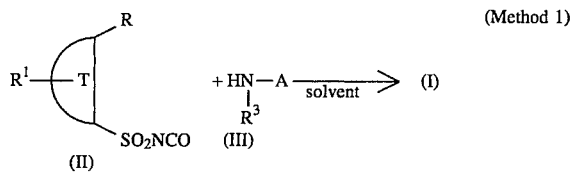

wherein,

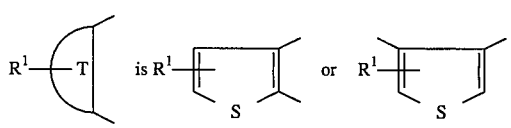

The above reaction may be carried out in solvent such as methylene chloride, dichloro ethane or chloroform, and then the solvent can be used with catalytic amount of base such as DABCO(1,4-diazabicyclo[5.4.0]undece-7-ene), DBU(1, 8-diazabicyclo[5.4.0]undece-7-ene), etc.

The compounds of general formula(I) can be obtained by reacting the compounds having the following formula(IV) with a carbamate compound of the following formula(V).

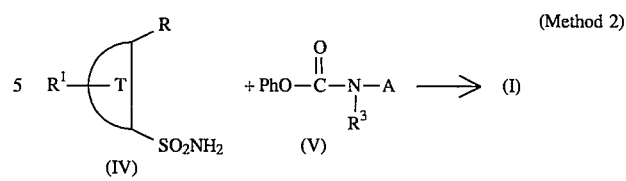

The compounds of the above formula(II) can be manufactured by reacting sulfonamide with phosgene.

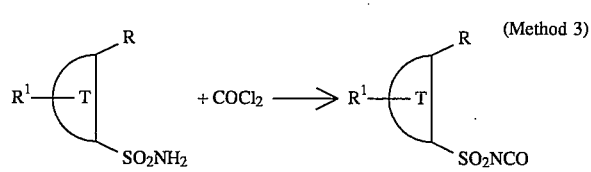

The thiophenesulfonamide compounds of the above formula(IV) may be prepared by the following reaction process.

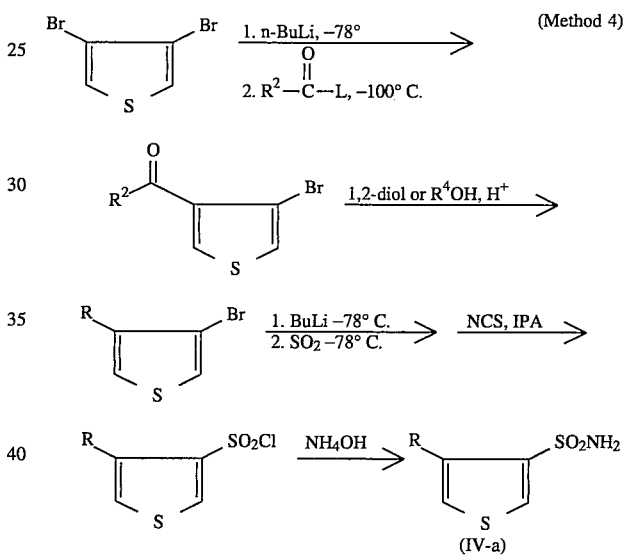

In the above reaction, L is leaving group such as OEt, $NMe_2$, or $N(CH_3)OCH_3$ and R, $R^1$ and $R^2$ are as the above defined.

Sulfonamide substituted at 2,3-position of the following formula(IV-b) can be obtained by the method 4 of the above, but 2,3-dibromothiophene is used as the starting material.

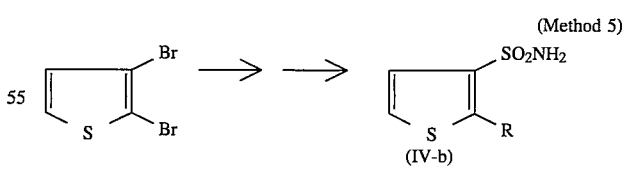

Sulfonamide of the following formula(IV-c) can be obtained by the following reaction process, and then 3-bromothiophene is used as the starting material.

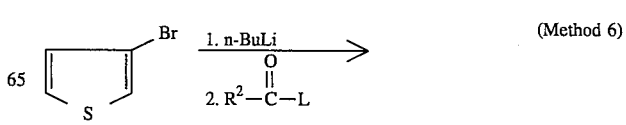

-continued

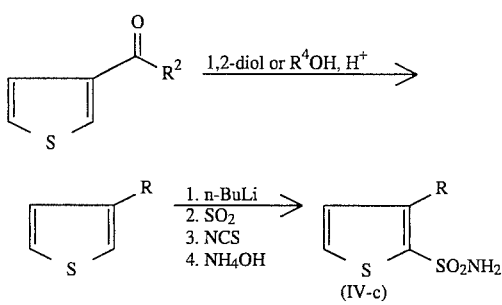

The heterocyclic amine compound of formula(III) may be prepared by a skill person in this technical field from a method disclosed in literatures or the simple transformation of it.

For example, European Patent Application No. 84,244 (Pub. Jul. 27, 1983) and J. Am. Chem. Soc., 69,3072(1947) of W. Braker et al. discloses a method for preparing aminopyrimidine and triazine substituted with acetyl group. European patent No. 72,347 and U.S. Pat. Nos. 4,443,243/ 4,487,915 disclose a method for preparing aminopyrimidine and/or triazine substituted with haloalkyl such as $OCHF_2$, $SCHF_2$, $OCH_2CH_2F$ anti $OCH_2CF_3$ etc. and haloalkylthio as a substitution group.

European Patent No. 108,708, U.S. Pat. Nos. 4,515,626/ 4,600,428 disclose cyclopropylpyrimidine and/or triazine substituted with alkyl, haloalkyl, alkoxy, haloalkoxy, alkylamino, dialkylamino and alkoxyalkyl group etc.

European Patent No. 15,863 discloses a method for preparing the compound of the above formula(VI), as 5,6-dihydro-puro[2,3-d] pyrimidine-2-amine compounds and cyclopenta[dd]pyrimidine-2-amine compounds which A is $A_2$; and 6,7-dihydro-5H-pyrano-[2,3-d] pyrimidine-2-amine compound which A is $A_3$.

European Patent No. 46,677 discloses puro[2,3-d]pyridine-2-amine compounds which A is $A_4$ in the formula(VI), and European Patent No. 73,562 discloses heterocyclic compounds which A is $A_5$.

The compound of formula(VI) which A is $A_6$ can be prepared by European Patent No. 94,260. The compound of formula(VI) which A is $A_7$ can be manufactured by the method of European Patent No. 125,864.

Common methods for preparing aminopyridine and triazine compounds are arranged on the following literatures: "The chemistry and Heterocyclic compounds", Series, Interscience Publishers, Inc., New York and London; "Pyrimidines", Vol. 16, D. J. Brown Ed.; "S-Triazines and Derivatives", Vol. 13, E. M. Smolin and L. Rapaport. Composition of triazine compounds is disclosed in F. C. Schaefer, U.S. Pat. No. 3,154,547 and K. R. Huffman and F. C. Schaefer, J. Org. Chem., 28, 1812(1963).

On the other hand, salts of the compound of the above formula(I) also are useful as herbicide, and they can be prepared by various methods according to prior art.

For example, metal salts of the compound can be prepared by reacting the above formula(I) compound with strong basic anion, e.g. alkali or alkaline earth metal solution having hydroxyl group, alkoxide or carbonate, and also quaternary amine salt alike.

A salt of the formula(I) compound may also be obtained by cation exchange. The cation exchange can be manufactured by directly reacting solution containing cation for exchange with solution of salt of formula(I), for example, solution of alkali metal or quaternary amine salt.

This method is useful when the desired salt is water insoluble, for example, copper salt is separated by filtering.

This ion exchange may be carried out by passing through a column of cation exchange resin with solution of salt of the formula(I), for example, alkaline metal or quarternary amine salt solution.

This method is useful when the desirable salt is water soluble, especially sodium, potassium or calcium salt.

The above manufacturing methods am summarized briefly, but the methods can be easily carried out by a skill person in this technical field of composition and manufacturing for sulfonyl urea or organic composition.

The compounds of the above general formula(I) according to the present invention are specified as the following Tables 1~45;

TABLE 1

| $R^1$ | $R^2$ | $R^3$ | X | Y | mp (°C.) |
|---|---|---|---|---|---|
| H | $CH_2F$ | H | $OCH_3$ | $OCH_3$ | 191–194 |
| H | $CH_2F$ | H | $CH_3$ | $OCH_3$ | 185–189 |
| H | $CH_2F$ | H | $CH_3$ | $CH_3$ | 179–184 |
| H | $CH_2F$ | H | Cl | $OCH_3$ | 182–185 |
| H | $CH_2F$ | H | Br | $OCH_3$ | |
| H | $CH_2F$ | H | H | $CH_3$ | |
| H | $CH_2F$ | H | $OCH_3$ | H | |
| H | $CH_2F$ | H | $OCH_3$ | $CH_2OC_2H_5$ | |
| H | $CH_2F$ | H | $OCF_2H$ | $OCH_3$ | |
| H | $CH_2F$ | H | $OCH_3$ | $CH(OCH_3)_2$ | |
| H | $CH_2F$ | H | $CH_3$ | $OC_2H_5$ | |
| H | $CH_2F$ | H | $CH_3$ | $CH_2OCH_3$ | |
| H | $CH_2F$ | H | $OCH_3$ | $CH_2OCH_3$ | |

TABLE 1-continued

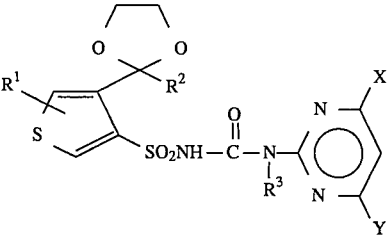

| R¹ | R² | R³ | X | Y | mp (°C.) |
|---|---|---|---|---|---|
| H | CH₂F | H | C₂H₅ | OCH₃ | |
| H | CH₂F | H | OC₂H₅ | OCH₃ | |
| H | CH₂F | H | OCH₂CF₃ | OCH₃ | |
| H | CH₂F | H | CF₂ | OCH₃ | |
| H | CH₂F | H | CH₂F | OCH₃ | |
| H | CH₂F | H | CH₂Cl | OCH₃ | |
| H | CH₂F | H | CH₂Br | OCH₃ | |
| H | CH₂F | H | F | OCH₃ | |
| H | CH₂F | H | I | OCH₃ | |
| H | CH₂F | H | OCH₂CH₂F | OCH₃ | |
| H | CH₂F | H | OCH₂CH₂CF₃ | OCH₃ | |
| H | CH₂F | H | OCH₂CHF₂ | CH₃ | |
| H | CH₂F | H | OCH₂CF₃ | CH₃ | |
| H | CH₂F | H | Cl | OC₂H₅ | |
| H | CH₂F | H | OC₂H₅ | NHCH₃ | |
| H | CH₂F | H | OC₂H₅ | CH₂SCH₃ | |
| H | CH₂F | H | OCF₂H | CH₃ | |
| H | CH₂F | H | Cl | OCF₂H | |
| H | CH₂F | H | NH₂ | OC₂H₅ | |
| H | CH₂F | H | n-C₃H₂ | OCH₃ | |
| H | CH₂F | H | NHCH₃ | OCH₃ | |
| H | CH₂F | H | OCH₃ | SCH₃ | |
| H | CH₂F | H | OCH₃ | SCF₂H | |
| H | CH₂F | H | OCH₃ | OCH₂CCH | |
| H | CH₂F | H | OCH₃ | OCH₂CH=CH₂ | |
| H | CH₂F | H | OCH₃ | CCH | |
| H | CH₂F | H | OCH₃ | N(CH₃)₂ | |
| H | CH₂F | H | OCH₃ | cyclopropyl | |
| H | CH₂F | H | OCH₃ | NH₂ | |
| H | CH₂F | H | OCH₃ | CF₃ | |
| H | CH₂F | H | OCH₃ | OCH₂CH₂OCH₃ | |
| H | CH₂F | H | OCH₃ | CH₂SCH₃ | |
| H | CH₂F | H | OCH₃ | CHO | |
| H | CH₂F | H | OCH₃ | COCH₃ | |
| H | CH₂F | H | OCH₃ | CH(SCH₃)OC₂H₅ | |
| H | CH₂F | H | OCH₃ | C(CH₃)(SCH₃)₂ | |
| H | CH₂F | H | OCH₃ | C(SC₂H₅)₂ | |
| H | CH₂F | H | OCH₃ | 1,3-dioxolan-2-yl | |
| H | CH₂F | H | OCH₃ | 2-methyl-1,3-oxathiolan-2yl | |
| H | CH₂F | H | OCH₃ | 1,3-oxathian-2-yl | |
| H | CH₂F | H | OCH₃ | 2-methyl-1,3-dithian-2-yl | |
| H | CH₂F | H | OCH₃ | 4-methyl-1,3-dioxolan-2-yl | |
| H | CH₂F | H | OCH₃ | 2-4-dimethyl-1,3-dithiolan-2-yl | |
| H | CH₂F | H | OCH₃ | N(OCH₃)(CH₃) | |
| H | CH₂F | H | OCH₃ | CCCH₃ | |
| H | CH₂F | H | OCH₃ | C₂H₅ | |
| H | CH₂F | H | OCH₃ | OCF₂Br | |
| H | CHFCH₃ | H | OCH₃ | OC₂H₅ | |
| H | CHFCH₃ | H | CH₃ | OCH₃ | |
| H | CHFCH₃ | H | CH₃ | CH₃ | |
| H | CHFCH₃ | H | Cl | OCH₃ | |
| H | CHFCH₃ | H | Br | OCH₃ | |
| H | CHFCH₃ | H | CH₃ | H | |
| H | CHFCH₃ | H | OCH₃ | CH₂OC₂H₅ | |
| H | CHFCH₃ | H | OCF₂H | OCH₃ | |
| H | CHFCH₃ | H | OCH₃ | CH(OCH₃)₂ | |
| H | CHFCH₃ | H | CH₃ | OC₂H₅ | |
| H | CHFCH₃ | H | CH₃ | CH₂OCH₃ | |
| H | CHFCH₃ | H | OCH₃ | CH₂OCH₃ | |
| H | CHFCH₃ | H | OCH₃ | C₂H₅ | |

TABLE 1-continued

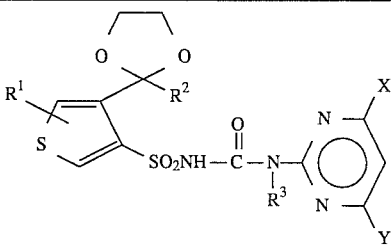

| R¹ | R² | R³ | X | Y | mp (°C.) |
|---|---|---|---|---|---|
| H | CHFCH₃ | H | OC₂H₅ | OCH₃ | |
| H | CHFCH₃ | H | OCH₂CF₃ | OCH₃ | |
| H | CHFCH₃ | H | CF₃ | OCH₃ | |
| H | CHFCH₃ | H | CH₂F | OCH₃ | |
| H | CHFCH₃ | H | CH₂Cl | OCH₃ | |
| H | CHFCH₃ | H | CH₂Br | OCH₃ | |
| H | CHFCH₃ | H | F | OCH₃ | |
| H | CHFCH₃ | H | I | OCH₃ | |
| H | CHFCH₃ | H | OCH₂CH₂F | OCH₃ | |
| H | CHFCH₃ | H | OCH₂CH₂CF₃ | OCH₃ | |
| H | CHFCH₃ | H | OCH₂CHF₂ | CH₃ | |
| H | CHFCH₃ | H | OCH₂CF₃ | CH₃ | |
| H | CHFCH₃ | H | Cl | OC₂H₅ | |
| H | CHFCH₃ | H | OC₂H₅ | NHCH₃ | |
| H | CHFCH₃ | H | OCH₃ | CH₂SCH₃ | |
| H | CHFCH₃ | H | OCF₂H | CH₃ | |
| H | CHFCH₃ | H | Cl | OCF₂H | |
| H | CH₂CH₂F | H | OCH₃ | OCH₃ | |
| H | CH₂CH₂F | H | CH₃ | OCH₃ | |
| H | CH₂CH₂F | H | CH₃ | CH₃ | |
| H | CH₂CH₂F | H | Cl | OCH₃ | |
| H | CH₂CH₂F | H | Br | OCH₃ | |
| H | CH₂CH₂F | H | CH₃ | H | |
| H | CH₂CH₂F | H | OCH₃ | H | |
| H | CH₂CH₂F | H | OCH₃ | CH₂OC₂H₅ | |
| H | CH₂CH₂F | H | OCF₂H | OCH₃ | |
| H | CH₂CH₂F | H | OCH₃ | CH(OCH₃)₂ | |
| H | CH₂CH₂F | H | CH₃ | OC₂H₅ | |
| H | CH₂CH₂F | H | CH₃ | CH₂OCH₃ | |
| H | CH₂CH₂F | H | OCH₃ | CH₂OCH₃ | |
| H | CH₂CH₂F | H | OCH₃ | C₂H₅ | |
| H | CH₂CH₂F | H | OC₂H₅ | OCH₃ | |
| H | CH₂CH₂F | H | OCH₂CF₃ | OCH₃ | |
| H | CH₂CH₂F | H | CF₃ | OCH₃ | |
| H | CH₂CH₂F | H | CH₂F | OCH₃ | |
| H | CH₂CH₂F | H | CH₂Cl | OCH₃ | |
| H | CH₂CH₂F | H | CH₂Br | OCH₃ | |
| H | CH₂CH₂F | H | F | OCH₃ | |
| H | CH₂CH₂F | H | I | OCH₃ | |
| H | CH₂CH₂F | H | OCH₂CH₂F | OCH₃ | |
| H | CH₂CH₂F | H | OCH₂CH₂CF₃ | OCH₃ | |
| H | CH₂CH₂F | H | OCH₂CHF₂ | CH₃ | |
| H | CH₂CH₂F | H | OCH₂CF₃ | CH₃ | |
| H | CH₂CH₂F | H | Cl | OC₂H₅ | |
| H | CH₂CH₂F | H | OC₂H₅ | NHCH₃ | |
| H | CH₂CH₂F | H | OCH₃ | CH₂SCH₃ | |
| H | CH₂CH₂F | H | OCF₂H | CH₃ | |
| H | CH₂CH₂F | H | Cl | OCF₂H | |
| H | CH₂Cl | H | OCH₃ | OCH₃ | 208–211 |
| H | CH₂Cl | H | CH₃ | OCH₃ | 205–209 |
| H | CH₂Cl | H | CH₃ | CH₃ | 203–206 |
| H | CH₂Cl | H | Cl | OCH₃ | 188–192 |
| H | CH₂Cl | H | Br | OCH₃ | |
| H | CH₂Cl | H | CH₃ | Cl | 186–190 |
| H | CH₂Cl | H | OCH₃ | H | |
| H | CH₂Cl | H | OCH₃ | CH₂OC₂H₅ | |
| H | CH₂Cl | H | OCF₂H | OCH₃ | |
| H | CH₂Cl | H | OCH₃ | CH(OCH₃)₂ | |
| H | CH₂Cl | H | CH₃ | OC₂H₅ | 175–186 |
| H | CH₂Cl | H | CH₃ | CH₂OCH₃ | |
| H | CH₂Cl | H | OCH₃ | CH₂OCH₃ | |
| H | CH₂Cl | H | OCH₃ | C₂H₅ | |
| H | CH₂Cl | H | OC₂H₅ | OCH₃ | |
| H | CH₂Cl | H | OCH₂CF₃ | OCH₃ | |
| H | CH₂Cl | H | CF₃ | OCH₃ | |

TABLE 1-continued

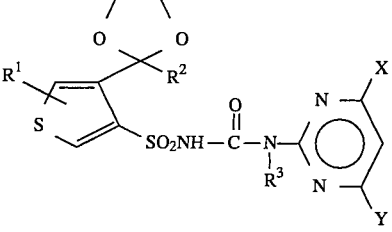

| R¹ | R² | R³ | X | Y | mp (°C.) |
|---|---|---|---|---|---|
| H | CH₂Cl | H | CH₂F | OCH₃ | |
| H | CH₂Cl | H | CH₂Cl | OCH₃ | |
| H | CH₂Cl | H | CH₂Br | OCH₃ | |
| H | CH₂Cl | H | F | OCH₃ | |
| H | CH₂Cl | H | I | OCH₃ | |
| H | CH₂Cl | H | OCH₂CH₂F | OCH₃ | |
| H | CH₂Cl | H | OCH₂CH₂CF₃ | OCH₃ | |
| H | CH₂Cl | H | OCH₂CHF₂ | CH₃ | |
| H | CH₂Cl | H | OCH₂CF₃ | CH₃ | |
| H | CH₂Cl | H | Cl | OC₂H₅ | 190–193 |
| H | CH₂Cl | H | OC₂H₅ | NHCH₃ | |
| H | CH₂Cl | H | OCH₃ | CH₂SCH₃ | |
| H | CH₂Cl | H | OCF₂H | CH₃ | |
| H | CH₂Cl | H | Cl | OCF₂H | |
| H | CHClCH₃ | H | OCH₃ | OCH₃ | |
| H | CHClCH₃ | H | CH₃ | OCH₃ | |
| H | CHClCH₃ | H | CH₃ | CH₃ | |
| H | CHClCH₃ | H | Cl | OCH₃ | |
| H | CHClCH₃ | H | Br | OCH₃ | |
| H | CHClCH₃ | H | CH₃ | H | |
| H | CHClCH₃ | H | OCH₃ | H | |
| H | CHClCH₃ | H | OCH₃ | CH₂OC₂H₅ | |
| H | CHClCH₃ | H | OCF₂H | OCH₃ | |
| H | CHClCH₃ | H | OCH₃ | CH(OCH₃)₂ | |
| H | CHClCH₃ | H | CH₃ | OC₂H₅ | |
| H | CHClCH₃ | H | CH₃ | CH₂OCH₃ | |
| H | CHClCH₃ | H | OCH₃ | CH₂OCH₃ | |
| H | CHClCH₃ | H | OCH₃ | C₂H₅ | |
| H | CHClCH₃ | H | OC₂H₅ | OCH₃ | |
| H | CHClCH₃ | H | OCH₂CF₃ | OCH₃ | |
| H | CHClCH₃ | H | CF₃ | OCH₃ | |
| H | CHClCH₃ | H | CH₂F | OCH₃ | |
| H | CHClCH₃ | H | CH₂Cl | OCH₃ | |
| H | CHClCH₃ | H | CH₂Br | OCH₃ | |
| H | CHClCH₃ | H | F | OCH₃ | |
| H | CHClCH₃ | H | I | OCH₃ | |
| H | CHClCH₃ | H | OCH₂CH₂F | OCH₃ | |
| H | CHClCH₃ | H | OCH₂CH₂CF₃ | OCH₃ | |
| H | CHClCH₃ | H | OCH₃CHF₂ | CH₃ | |
| H | CHClCH₃ | H | OCH₂CF₃ | CH₃ | |
| H | CHClCH₃ | H | Cl | OC₂H₅ | |
| H | CHClCH₃ | H | OC₂H₅ | NHCH₃ | |
| H | CHClCH₃ | H | OCH₃ | CH₂SCH₃ | |
| H | CHClCH₃ | H | OCF₂H | CH₃ | |
| H | CHClCH₃ | H | Cl | OCF₂H | |
| H | CH₂Br | H | OCH₃ | OCH₃ | |
| H | CH₂Br | H | CH₃ | OCH₃ | |
| H | CH₂Br | H | CH₃ | CH₃ | |
| H | CH₂Br | H | Cl | OCH₃ | |
| H | CH₂Br | H | Br | OCH₃ | |
| H | CH₂Br | H | CH₃ | H | |
| H | CH₂Br | H | OCH₃ | H | |
| H | CH₂Br | H | OCH₃ | CH₂OC₂H₅ | |
| H | CH₂Br | H | OCF₂H | OCH₃ | |
| H | CH₂Br | H | OCH₃ | CH(OCH₃)₂ | |
| H | CH₂Br | H | CH₃ | OC₂H₅ | |
| H | CH₂Br | H | CH₃ | CH₂OCH₃ | |
| H | CH₂Br | H | OCH₃ | CH₂OCH₃ | |
| H | CH₂Br | H | OCH₃ | C₂H₅ | |
| H | CH₂Br | H | OCH₂CF₃ | OCH₃ | |
| H | CH₂Br | H | OC₂H₅ | OCH₃ | |
| H | CH₂Br | H | CF₃ | OCH₃ | |
| H | CH₂Br | H | CH₂F | OCH₃ | |
| H | CH₂Br | H | CH₂Cl | OCH₃ | |
| H | CH₂Br | H | CH₂Br | OCH₃ | |

TABLE 1-continued

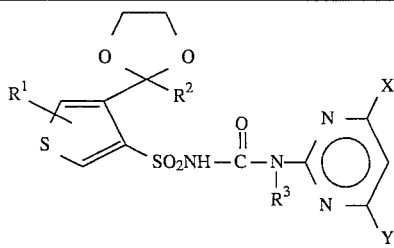

| R¹ | R² | R³ | X | Y | mp (°C.) |
|---|---|---|---|---|---|
| H | CH₂Br | H | F | OCH₃ | |
| H | CH₂Br | H | I | OCH₃ | |
| H | CH₂Br | H | OCH₂CH₂F | OCH₃ | |
| H | CH₂Br | H | OCH₂CH₂CF₃ | OCH₃ | |
| H | CH₂Br | H | OCH₂CHF₂ | CH₃ | |
| H | CH₂Br | H | OCH₂CF₃ | CH₃ | |
| H | CH₂Br | H | Cl | OC₂H₅ | |
| H | CH₂Br | H | OCH₂H₅ | NHCH₃ | |
| H | CH₂Br | H | OCH₃ | CH₂SCH₃ | |
| H | CH₂Br | H | OCF₂H | CH₃ | |
| H | CH₂Br | H | Cl | CHF₂H | |
| H | CF₃ | H | OCH₃ | OCH₃ | 209–212 |
| H | CF₃ | H | CH₃ | OCH₃ | 194–197 |
| H | CF₃ | H | CH₃ | CH₃ | 193–196 |
| H | CF₃ | H | Cl | OCH₃ | 196–200 |
| H | CHF₂ | H | Br | OCH₃ | |
| H | CHF₂ | H | CH₃ | H | |
| H | CHF₂ | H | OCH₃ | H | |
| H | CHF₂ | H | OCH₃ | CH₂OC₂H₅ | |
| H | CHF₂ | H | OCF₂H | OCH₃ | |
| H | CHF₂ | H | OCH₃ | CH(OCH₃)₂ | |
| H | CHF₂ | H | CH₃ | OC₂H₅ | |
| H | CHF₂ | H | CH₃ | CH₂OCH₃ | |
| H | CHF₂ | H | OCH₃ | CH₂OCH₃ | |
| H | CHF₂ | H | OCH₃ | C₂H₅ | |
| H | CHF₂ | H | OC₂H₅ | OCH₃ | |
| H | CHF₂ | H | OCH₂CF₃ | OCH₃ | |
| H | CHF₂ | H | CF₃ | OCH₃ | |
| H | CHF₂ | H | CH₂F | OCH₃ | |
| H | CHF₂ | H | CH₂Cl | OCH₃ | |
| H | CHF₂ | H | CH₂Br | OCH₃ | |
| H | CHF₂ | H | F | OCH₃ | |
| H | CHF₂ | H | I | OCH₃ | |
| H | CHF₂ | H | OCH₂CH₂F | OCH₃ | |
| H | CHF₂ | H | OCH₂CH₂CF₃ | OCH₃ | |
| H | CHF₂ | H | OCH₂CF₃ | CH₃ | |
| H | CHF₂ | H | OCH₂CHF₂ | CH₃ | |
| H | CHF₂ | H | Cl | OC₂H₅ | |
| H | CHF₂ | H | OC₂H₅ | NHCH₃ | |
| H | CHF₂ | H | OCH₃ | CH₂SCH₃ | |
| H | CHF₂ | H | OCF₂H | CH₃ | |
| H | CHF₂ | H | Cl | OCF₂H | |
| H | CHFCl | H | OCH₃ | OCH₃ | |
| H | CHFCl | H | CH₃ | OCH₃ | |
| H | CHFCl | H | CH₃ | CH₃ | |
| H | CHFCl | H | Cl | OCH₃ | |
| H | CHFCl | H | Br | OCH₃ | |
| H | CHFCl | H | CH₃ | H | |
| H | CHFCl | H | OCH₃ | H | |
| H | CHFCl | H | OCH₃ | CH₂OC₂H₅ | |
| H | CHFCl | H | OCF₂H | OCH₃ | |
| H | CHFCl | H | OCH₃ | CH(OCH₃)₂ | |
| H | CHFCl | H | CH₃ | OC₂H₅ | |
| H | CHFCl | H | CH₃ | CH₂OCH₃ | |
| H | CHFCl | H | OCH₃ | CH₂OCH₃ | |
| H | CHFCl | H | OCH₃ | C₂H₅ | |
| H | CHFCl | H | OC₂H₅ | OCH₃ | |
| H | CHFCl | H | OCH₂CF₃ | OCH₃ | |
| H | CHFCl | H | CF₃ | OCH₃ | |
| H | CHFCl | H | CH₂F | OCH₃ | |
| H | CHFCl | H | CH₂Cl | OCH₃ | |
| H | CHFCl | H | CH₂Br | OCH₃ | |
| H | CHFCl | H | F | OCH₃ | |
| H | CHFCl | H | I | OCH₃ | |
| H | CHFCl | H | OCH₂CH₂F | OCH₃ | |

TABLE 1-continued

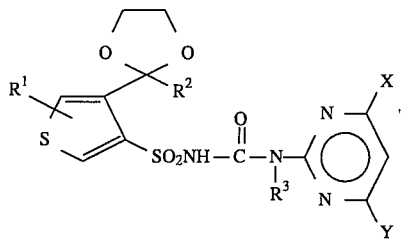

| R¹ | R² | R³ | X | Y | mp (°C.) |
|---|---|---|---|---|---|
| H | CHFCl | H | OCH₂CH₂CF₃ | OCH₃ | |
| H | CHFCl | H | OCH₂CHF₂ | CH₃ | |
| H | CHFCl | H | OCH₂CF₃ | CH₃ | |
| H | CHFCl | H | Cl | OC₂H₅ | |
| H | CHFCl | H | OC₂H₅ | NHCH₃ | |
| H | CHFCl | H | OCH₃ | CH₂SCH₃ | |
| H | CHFCl | H | OCF₂H | CH₃ | |
| H | CHFCl | H | Cl | OCF₂H | |
| H | CHFCl | H | n-C₃H₇ | OCH₃ | |
| H | CHFCl | H | OCH₃ | NHCH₃ | |
| H | CHFCl | H | OCH₃ | N(CH₃)₂ | |
| H | CHFCl | H | OCH₃ | cyclopropyl | |
| H | CHFCl | H | OCH₃ | OCH₂CH₂OCH₃ | |
| H | CHFCl | H | OCH₂H₅ | CH₂SCH₃ | |
| H | CHFCl | H | OCH₃ | CH(SCH₃)OC₂H₅ | |
| H | CHFCl | H | OCH₃ | CH(SC₂H₅)₂ | |
| H | CHFCl | H | OCH₃ | 1,3-dioxolan-2-yl | |
| H | CHFCl | H | OCH₃ | N(OCH₃)CH₃ | |
| H | CHFCl | H | OCH₃ | C₂H₅ | |
| H | CHFCl | H | OCH₃ | CF₃ | |
| 5-F | CH₂F | H | OCH₃ | OCH₃ | |
| 5-Cl | CH₂F | H | OCH₃ | OCH₃ | |
| 5-Cl | CH₂Cl | H | OCH₃ | OCH₃ | |
| 5-Cl | CH₂F | H | CH₃ | OCH₃ | |
| 5-Cl | CH₂F | H | CH₃ | CH₃ | |
| 5-Cl | CH₂F | H | Cl | OCH₃ | |
| 5-Br | CH₂F | H | OCH₃ | OCH₃ | |
| 5-CH₂CN | CH₂F | H | OCH₃ | OCH₃ | |
| 5-OCH₃ | CH₂F | H | OCH₃ | OCH₃ | |
| 5-SCH₃ | CH₂F | H | OCH₃ | OCH₃ | |
| 5-OCF₂H | CH₂F | H | OCH₃ | OCH₃ | |
| H | CH₂F | CH₃ | OCH₃ | OCH₃ | |
| H | CH₂F | CH₃ | CH₃ | OCH₃ | |
| H | CH₂Cl | CH₃ | OCH₃ | OCH₃ | |
| H | CHF₂ | CH₃ | OCH₃ | OCH₃ | |
| H | CH₂Br | CH₃ | OCH₃ | OCH₃ | |
| 5-Cl | CH₂Cl | CH₃ | OCH₃ | OCH₃ | |

TABLE 2

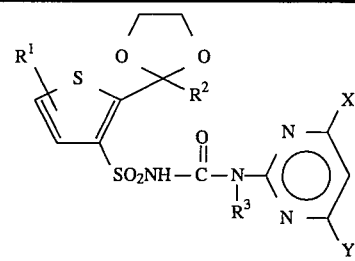

| R¹ | R² | R³ | X | Y | mp (°C.) |
|---|---|---|---|---|---|
| H | CH₂F | H | OCH₃ | OCH₃ | 134–137 |
| H | CH₂F | H | CH₃ | OCH₃ | 203–207 |
| H | CH₂F | H | CH₃ | CH₃ | 205–210 |
| H | CH₂F | H | Cl | OCH₃ | 180–184 |
| H | CH₂F | H | Br | OCH₃ | |
| H | CH₂F | H | Cl | CH₃ | |
| H | CH₂F | H | OCH₃ | H | 193–198 |
| H | CH₂F | H | OCH₃ | CH₂OC₂H₅ | |
| H | CH₂F | H | OCF₂H | OCH₃ | |

TABLE 2-continued

| R¹ | R² | R³ | X | Y | mp (°C.) |
|---|---|---|---|---|---|
| H | CH₂F | H | OCH₃ | CH(OCH₃)₂ | |
| H | CH₂F | H | CH₃ | OC₂H₅ | 187–190 |
| H | CH₂F | H | CH₃ | CH₂OCH₃ | |
| H | CH₂F | H | OCH₃ | CH₂OCH₃ | |
| H | CH₂F | H | C₂H₅ | OCH₃ | |
| H | CH₂F | H | OC₂H₅ | OCH₃ | |
| H | CH₂F | H | OCH₂CF₃ | OCH₃ | |
| H | CH₂F | H | CF₃ | OCH₃ | |
| H | CH₂F | H | CH₂F | OCH₃ | |
| H | CH₂F | H | CH₂Cl | OCH₃ | |
| H | CH₂F | H | CH₂Br | OCH₃ | |
| H | CH₂F | H | F | OCH₃ | |
| H | CH₂F | H | I | OCH₃ | |
| H | CH₂F | H | OCH₂CH₂F | OCH₃ | |
| H | CH₂F | H | OCH₂CH₂CF₃ | OCH₃ | |
| H | CH₂F | H | OCH₂CHF₂ | CH₃ | |
| H | CH₂F | H | OCH₂CF₃ | CH₃ | |
| H | CH₂F | H | Cl | OC₂H₅ | 170–172 |
| H | CH₂F | H | OC₂H₅ | NHCH₃ | |
| H | CH₂F | H | OC₂H₅ | CH₂SCH₃ | |
| H | CH₂F | H | OCF₂H | CH₃ | |
| H | CH₂F | H | Cl | OCF₂H | |
| H | CH₂F | H | NH₂ | OC₂H₅ | |
| H | CH₂F | H | n-C₃H₇ | OCH₃ | |
| H | CH₂F | H | NHCH₃ | OCH₃ | |
| H | CH₂F | H | OCH₃ | SCH₃ | |
| H | CH₂F | H | OCH₃ | SCF₂H | |
| H | CH₂F | H | OCH₃ | OCH₂CCH | |
| H | CH₂F | H | OCH₃ | OCH₂CH=CH₂ | |
| H | CH₂F | H | OCH₃ | CHCH | |
| H | CH₂F | H | OCH₃ | N(CH₃)₂ | |
| H | CH₂F | H | OCH₃ | cyclopropyl | |
| H | CH₂F | H | OCH₃ | NH₂ | |
| H | CH₂F | H | OCH₃ | CF₃ | |
| H | CH₂F | H | OCH₃ | OCH₂CH₂OCH₃ | |
| H | CH₂F | H | OCH₃ | CH₂SCH₃ | |
| H | CH₂F | H | OCH₃ | CHO | |
| H | CH₂F | H | OCH₃ | COCH₃ | |
| H | CH₂F | H | OCH₃ | CH(SCH₃)OC₂H₅ | |
| H | CH₂F | H | OCH₃ | C(CH₃)(SCH₃)₂ | |
| H | CH₂F | H | OCH₃ | C(SC₂H₅)₂ | |
| H | CH₂F | H | OCH₃ | 1,3-dioxolan-2-yl | |
| H | CH₂F | H | OCH₃ | 2-methyl-1,3-oxathiolan-2yl | |
| H | CH₂F | H | OCH₃ | 1,3-oxathian-2-yl | |
| H | CH₂F | H | OCH₃ | 2-methyl-1,3-dithian-2-yl | |
| H | CH₂F | H | OCH₃ | 4-methyl-1,3-dioxolan-2-yl | |
| H | CH₂F | H | OCH₃ | 2-4-dimethyl-1,3-dithiolan-2-yl | |
| H | CH₂F | H | OCH₃ | N(OCH₃)(CH₃) | |
| H | CH₂F | H | OCH₃ | CCCH₃ | |
| H | CH₂F | H | OCH₃ | C₂H₅ | |
| H | CH₂F | H | OCH₃ | OCF₂Br | |
| H | CHFCH₃ | H | OCH₃ | OC₂H₅ | |
| H | CHFCH₃ | H | CH₃ | OCH₃ | |
| H | CHFCH₃ | H | CH₃ | CH₃ | |
| H | CHFCH₃ | H | Cl | OCH₃ | |
| H | CHFCH₃ | H | Br | OCH₃ | |
| H | CHFCH₃ | H | CH₃ | H | |
| H | CHFCH₃ | H | OCH₃ | H | |
| H | CHFCH₃ | H | OCH₃ | CH₂OC₂H₅ | |
| H | CHFCH₃ | H | OCF₂H | OCH₃ | |
| H | CHFCH₃ | H | OCH₃ | CH(OCH₃)₂ | |

TABLE 2-continued

| R¹ | R² | R³ | X | Y | mp (°C.) |
|---|---|---|---|---|---|
| H | CHFCH₃ | H | CH₃ | OC₂H₅ | |
| H | CHFCH₃ | H | CH₃ | CH₂OCH₃ | |
| H | CHFCH₃ | H | OCH₃ | CH₂OCH₃ | |
| H | CHFCH₃ | H | OCH₃ | C₂H₅ | |
| H | CHFCH₃ | H | OC₂H₅ | OCH₃ | |
| H | CHFCH₃ | H | OCH₂CF₃ | OCH₃ | |
| H | CHFCH₃ | H | CF₃ | OCH₃ | |
| H | CHFCH₃ | H | CH₂F | OCH₃ | |
| H | CHFCH₃ | H | CH₂Cl | OCH₃ | |
| H | CHFCH₃ | H | CH₂Br | OCH₃ | |
| H | CHFCH₃ | H | F | OCH₃ | |
| H | CHFCH₃ | H | I | OCH₃ | |
| H | CHFCH₃ | H | OCH₂CH₂F | OCH₃ | |
| H | CHFCH₃ | H | OCH₂CH₂CF₃ | OCH₃ | |
| H | CHFCH₃ | H | OCH₂CHF₂ | CH₃ | |
| H | CHFCH₃ | H | OCH₂CF₃ | CH₃ | |
| H | CHFCH₃ | H | Cl | OC₂H₅ | |
| H | CHFCH₃ | H | OC₂H₅ | NHCH₃ | |
| H | CHFCH₃ | H | OCH₃ | CH₂SCH₃ | |
| H | CHFCH₃ | H | OCF₂H | CH₃ | |
| H | CHFCH₃ | H | Cl | OCF₂H | |
| H | CH₂CH₂F | H | OCH₃ | OCH₃ | |
| H | CH₂CH₂F | H | CH₃ | OCH₃ | |
| H | CH₂CH₂F | H | CH₃ | CH₃ | |
| H | CH₂CH₂F | H | Cl | OCH₃ | |
| H | CH₂CH₂F | H | Br | OCH₃ | |
| H | CH₂CH₂F | H | CH₃ | H | |
| H | CH₂CH₂F | H | OCH₃ | H | |
| H | CH₂CH₂F | H | OCH₃ | CH₂OC₂H₅ | |
| H | CH₂CH₂F | H | OCF₂H | OCH₃ | |
| H | CH₂CH₂F | H | OCH₃ | CH(OCH₃)₂ | |
| H | CH₂CH₂F | H | CH₃ | OC₂H₅ | |
| H | CH₂CH₂F | H | CH₃ | CH₂OCH₃ | |
| H | CH₂CH₂F | H | OCH₃ | CH₂OCH₃ | |
| H | CH₂CH₂F | H | OCH₃ | C₂H₅ | |
| H | CH₂CH₂F | H | OC₂H₅ | OCH₃ | |
| H | CH₂CH₂F | H | OCH₂CF₃ | OCH₃ | |
| H | CH₂CH₂F | H | CF₃ | OCH₃ | |
| H | CH₂CH₂F | H | CH₂F | OCH₃ | |
| H | CH₂CH₂F | H | CH₂Cl | OCH₃ | |
| H | CH₂CH₂F | H | CH₂Br | OCH₃ | |
| H | CH₂CH₂F | H | F | OCH₃ | |
| H | CH₂CH₂F | H | I | OCH₃ | |
| H | CH₂CH₂F | H | OCH₂CH₂F | OCH₃ | |
| H | CH₂CH₂F | H | OCH₂CH₂CF₃ | OCH₃ | |
| H | CH₂CH₂F | H | OCH₂CHF₂ | CH₃ | |
| H | CH₂CH₂F | H | OCH₂CF₃ | CH₃ | |
| H | CH₂CH₂F | H | Cl | OC₂H₅ | |
| H | CH₂CH₂F | H | OC₂H₅ | NHCH₃ | |
| H | CH₂CH₂F | H | OCH₃ | CH₂SCH₃ | |
| H | CH₂CH₂F | H | OCF₂H | CH₃ | |
| H | CH₂CH₂F | H | Cl | OCF₂H | |
| H | CH₂Cl | H | OCH₃ | OCH₃ | 190–193 |
| H | CH₂Cl | H | CH₃ | OCH₃ | 216–220 |
| H | CH₂Cl | H | CH₃ | CH₃ | 213–217 |
| H | CH₂Cl | H | Cl | OCH₃ | 196–202 |
| H | CH₂Cl | H | Br | OCH₃ | |
| H | CH₂Cl | H | CH₃ | Cl | 195–198 |
| H | CH₂Cl | H | OCH₃ | H | |
| H | CH₂Cl | H | OCH₃ | CH₂OC₂H₅ | |
| H | CH₂Cl | H | OCF₂H | OCH₃ | |
| H | CH₂Cl | H | OCH₃ | CH(OCH₃)₂ | |
| H | CH₂Cl | H | CH₃ | OC₂H₅ | 198–203 |
| H | CH₂Cl | H | CH₃ | CH₂OCH₃ | |
| H | CH₂Cl | H | OCH₃ | CH₂OCH₃ | |

TABLE 2-continued

| R¹ | R² | R³ | X | Y | mp (°C.) |
|---|---|---|---|---|---|
| H | CH₂Cl | H | OCH₃ | C₂H₅ | |
| H | CH₂Cl | H | OC₂H₅ | OCH₃ | |
| H | CH₂Cl | H | OCH₂CF₃ | OCH₃ | |
| H | CH₂Cl | H | CF₃ | OCH₃ | |
| H | CH₂Cl | H | CH₂F | OCH₃ | |
| H | CH₂Cl | H | CH₂Cl | OCH₃ | |
| H | CH₂Cl | H | CH₂Br | OCH₃ | |
| H | CH₂Cl | H | F | OCH₃ | |
| H | CH₂Cl | H | I | OCH₃ | |
| H | CH₂Cl | H | OCH₂CH₂F | OCH₃ | |
| H | CH₂Cl | H | OCH₂CH₂CF₃ | OCH₃ | |
| H | CH₂Cl | H | OCH₂CHF₂ | CH₃ | |
| H | CH₂Cl | H | OCH₂CF₃ | CH₃ | |
| H | CH₂Cl | H | Cl | OC₂H₅ | 193–196 |
| H | CH₂Cl | H | OC₂H₅ | NHCH₃ | |
| H | CH₂Cl | H | OCH₃ | CH₂SCH₃ | |
| H | CH₂Cl | H | OCF₂H | CH₃ | |
| H | CH₂Cl | H | Cl | OCF₂H | |
| H | CHClCH₃ | H | OCH₃ | OCH₃ | |
| H | CHClCH₃ | H | CH₃ | OCH₃ | |
| H | CHClCH₃ | H | CH₃ | CH₃ | |
| H | CHClCH₃ | H | Cl | OCH₃ | |
| H | CHClCH₃ | H | Br | OCH₃ | |
| H | CHClCH₃ | H | CH₃ | H | |
| H | CHClCH₃ | H | OCH₃ | H | |
| H | CHClCH₃ | H | OCH₃ | CH₂OC₂H₅ | |
| H | CHClCH₃ | H | OCF₂H | OCH₃ | |
| H | CHClCH₃ | H | OCH₃ | CH(OCH₃)₂ | |
| H | CHClCH₃ | H | CH₃ | OC₂H₅ | |
| H | CHClCH₃ | H | CH₃ | CH₂OCH₃ | |
| H | CHClCH₃ | H | OCH₃ | CH₂OCH₃ | |
| H | CHClCH₃ | H | OCH₃ | C₂H₅ | |
| H | CHClCH₃ | H | OC₂H₅ | OCH₃ | |
| H | CHClCH₃ | H | OCH₂CF₃ | OCH₃ | |
| H | CHClCH₃ | H | CF₃ | OCH₃ | |
| H | CHClCH₃ | H | CH₂F | OCH₃ | |
| H | CHClCH₃ | H | CH₂Cl | OCH₃ | |
| H | CHClCH₃ | H | CH₂Br | OCH₃ | |
| H | CHClCH₃ | H | F | OCH₃ | |
| H | CHClCH₃ | H | I | OCH₃ | |
| H | CHClCH₃ | H | OCH₂CH₂F | OCH₃ | |
| H | CHClCH₃ | H | OCH₂CH₂CF₃ | OCH₃ | |
| H | CHClCH₃ | H | OCH₂CHF₂ | CH₃ | |
| H | CHClCH₃ | H | OCH₂CF₃ | CH₃ | |
| H | CHClCH₃ | H | Cl | OC₂H₅ | |
| H | CHClCH₃ | H | OC₂H₅ | NHCH₃ | |
| H | CHClCH₃ | H | OCH₃ | CH₂SCH₃ | |
| H | CHClCH₃ | H | OCF₂H | CH₃ | |
| H | CHClCH₃ | H | Cl | OCF₂H | |
| H | CH₂Br | H | OCH₃ | OCH₃ | |
| H | CH₂Br | H | CH₃ | OCH₃ | |
| H | CH₂Br | H | CH₃ | CH₃ | |
| H | CH₂Br | H | Cl | OCH₃ | |
| H | CH₂Br | H | Br | OCH₃ | |
| H | CH₂Br | H | CH₃ | H | |
| H | CH₂Br | H | OCH₃ | H | |
| H | CH₂Br | H | OCH₃ | CH₂OC₂H₅ | |
| H | CH₂Br | H | OCF₂H | OCH₃ | |
| H | CH₂Br | H | OCH₃ | CH(OCH₃)₂ | |
| H | CH₂Br | H | CH₃ | OC₂H₅ | |
| H | CH₂Br | H | CH₃ | CH₂OCH₃ | |
| H | CH₂Br | H | OCH₃ | CH₂OCH₃ | |
| H | CH₂Br | H | OCH₃ | C₂H₅ | |
| H | CH₂Br | H | OC₂H₅ | OCH₃ | |
| H | CH₂Br | H | OCH₂CF₃ | OCH₃ | |

TABLE 2-continued

| R¹ | R² | R³ | X | Y | mp (°C.) |
|---|---|---|---|---|---|
| H | CH₂Br | H | CF₃ | OCH₃ | |
| H | CH₂Br | H | CH₂F | OCH₃ | |
| H | CH₂Br | H | CH₂Cl | OCH₃ | |
| H | CH₂Br | H | CH₂Br | OCH₃ | |
| H | CH₂Br | H | F | OCH₃ | |
| H | CH₂Br | H | I | OCH₃ | |
| H | CH₂Br | H | OCH₂CH₂F | OCH₃ | |
| H | CH₂Br | H | OCH₂CH₂CF₃ | OCH₃ | |
| H | CH₂Br | H | OCH₂CHF₂ | CH₃ | |
| H | CH₂Br | H | OCH₂CF₃ | CH₃ | |
| H | CH₂Br | H | Cl | OC₂H₅ | |
| H | CH₂Br | H | OC₂H₅ | NHCH₃ | |
| H | CH₂Br | H | OCH₃ | CH₂SCH₃ | |
| H | CH₂Br | H | OCF₂H | CH₃ | |
| H | CH₂Br | H | Cl | OCF₂H | |
| H | CHF₂ | H | OCH₃ | OCH₃ | |
| H | CHF₂ | H | CH₃ | OCH₃ | |
| H | CHF₂ | H | CH₃ | CH₃ | |
| H | CHF₂ | H | Cl | OCH₃ | |
| H | CHF₂ | H | Br | OCH₃ | |
| H | CHF₂ | H | CH₃ | H | |
| H | CHF₂ | H | OCH₃ | H | |
| H | CHF₂ | H | OCH₃ | CH₂OC₂H₅ | |
| H | CHF₂ | H | OCF₂H | OCH₃ | |
| H | CHF₂ | H | OCH₃ | CH(OCH₃)₂ | |
| H | CHF₂ | H | CH₃ | OC₂H₅ | |
| H | CHF₂ | H | CH₃ | CH₂OCH₃ | |
| H | CHF₂ | H | OCH₃ | CH₂OCH₃ | |
| H | CHF₂ | H | OCH₃ | C₂H₅ | |
| H | CHF₂ | H | OC₂H₅ | OCH₃ | |
| H | CHF₂ | H | OCH₂CF₃ | OCH₃ | |
| H | CHF₂ | H | CF₃ | OCH₃ | |
| H | CHF₂ | H | CH₂F | OCH₃ | |
| H | CHF₂ | H | CH₂Cl | OCH₃ | |
| H | CHF₂ | H | CH₂Br | OCH₃ | |
| H | CHF₂ | H | F | OCH₃ | |
| H | CHF₂ | H | I | OCH₃ | |
| H | CHF₂ | H | OCH₂CH₂F | OCH₃ | |
| H | CHF₂ | H | OCH₂CH₂CF₃ | OCH₃ | |
| H | CHF₂ | H | OCH₂CF₃ | CH₃ | |
| H | CHF₂ | H | OCH₂CHF₂ | CH₃ | |
| H | CHF₂ | H | Cl | OC₂H₅ | |
| H | CHF₂ | H | OC₂H₅ | NHCH₃ | |
| H | CHF₂ | H | OCH₃ | CH₂SCH₃ | |
| H | CHF₂ | H | OCF₂H | CH₃ | |
| H | CHF₂ | H | Cl | OCF₂H | |
| H | CHFCl | H | OCH₃ | OCH₃ | |
| H | CHFCl | H | CH₃ | OCH₃ | |
| H | CHFCl | H | CH₃ | CH₃ | |
| H | CHFCl | H | Cl | OCH₃ | |
| H | CHFCl | H | Br | OCH₃ | |
| H | CHFCl | H | CH₃ | H | |
| H | CHFCl | H | OCH₃ | H | |
| H | CHFCl | H | OCH₃ | CH₂OC₂H₅ | |
| H | CHFCl | H | OCF₂H | OCH₃ | |
| H | CHFCl | H | OCH₃ | CH(OCH₃)₂ | |
| H | CHFCl | H | CH₃ | OC₂H₅ | |
| H | CHFCl | H | CH₃ | CH₂OCH₃ | |
| H | CHFCl | H | OCH₃ | CH₂OCH₃ | |
| H | CHFCl | H | OCH₃ | C₂H₅ | |
| H | CHFCl | H | OC₂H₅ | OCH₃ | |
| H | CHFCl | H | OCH₂CF₃ | OCH₃ | |
| H | CHFCl | H | CF₃ | OCH₃ | |
| H | CHFCl | H | CH₂F | OCH₃ | |
| H | CHFCl | H | CH₂Cl | OCH₃ | |

TABLE 2-continued

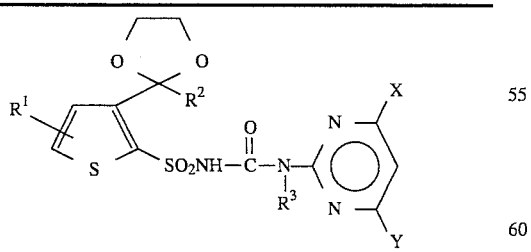

| R¹ | R² | R³ | X | Y | mp (°C.) |
|---|---|---|---|---|---|
| H | CHF(3 | H | CH₂Br | OCH₃ | |
| H | CHFCl | H | F | OCH₃ | |
| H | CHFCl | H | I | OCH₃ | |
| H | CHFCl | H | OCH₂CH₂F | OCH₃ | |
| H | CHFCl | H | OCH₂CH₂CF₃ | OCH₃ | |
| H | CHFCl | H | OCH₂CHF₂ | CH₃ | |
| H | CHFCl | H | OCH₂CF₃ | CH₃ | |
| H | CHFCl | H | Cl | OC₂H₅ | |
| H | CHFCl | H | OC₂H₅ | NHCH₃ | |
| H | CHFCl | H | OCH₃ | CH₂SCH₃ | |
| H | CHFCl | H | OCF₂H | CH₃ | |
| H | CHFCl | H | Cl | OCF₂H | |
| H | CHFCl | H | n-C₃H₇ | OCH₃ | |
| H | CHFCl | H | OCH₃ | NHCH₃ | |
| H | CHFCl | H | OCH₃ | N(CH₃)₂ | |
| H | CHFCl | H | OCH₃ | cyclopropyl | |
| H | CHFCl | H | OCH₃ | OCH₂CH₂OCH₃ | |
| H | CHFCl | H | OC₂H₅ | CH₂SCH₃ | |
| H | CHFCl | H | OCH₃ | CH(SCH₃)OC₂H₅ | |
| H | CHFCl | H | OCH₃ | CH(SC₂H₅)₂ | |
| H | CHFCl | H | OCH₃ | 1,3-dioxolan-2-yl | |
| H | CHFCl | H | OCH₃ | N(OCH₃)CH₃ | |
| H | CHFCl | H | OCH₃ | C₂H₅ | |
| H | CHFCl | H | OCH₃ | CF₃ | |
| 5-F | CH₂F | H | OCH₃ | OCH₃ | |
| 5-Cl | CH₂F | H | OCH₃ | OCH₃ | |
| 5-Cl | CH₂Cl | H | OCH₃ | OCH₃ | |
| 5-Cl | CH₂F | H | CH₃ | OCH₃ | |
| 5-Cl | CH₂F | H | CH₃ | CH₃ | |
| 5-Cl | CH₂F | H | Cl | OCH₃ | |
| 5-Br | CH₂F | H | OCH₃ | OCH₃ | |
| 5-CH₂CN | CH₂F | H | OCH₃ | OCH₃ | |
| 5-OCH₃ | CH₂F | H | OCH₃ | OCH₃ | |
| 5-SCH₃ | CH₂F | H | OCH₃ | OCH₃ | |
| 5-OCF₂H | CH₂F | H | OCH₃ | OCH₃ | |
| H | CH₂F | CH₃ | OCH₃ | OCH₃ | |
| H | CH₂F | CH₃ | CH₃ | OCH₃ | |
| H | CH₂Cl | CH₃ | OCH₃ | OCH₃ | |
| H | CHF₂ | CH₃ | OCH₃ | OCH₃ | |
| H | CH₂Br | CH₃ | OCH₃ | OCH₃ | |
| 4-Cl | CH₂Cl | CH₃ | OCH₃ | OCH₃ | |

TABLE 3

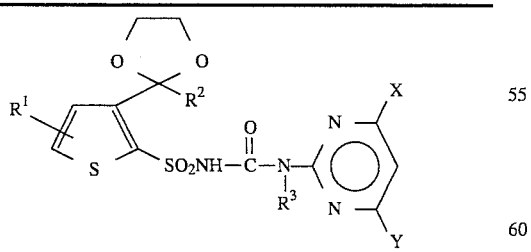

| R¹ | R² | R³ | X | Y | mp (°C.) |
|---|---|---|---|---|---|
| H | CH₂F | H | OCH₃ | OCH₃ | 193–196 |
| H | CH₂F | H | CH₃ | OCH₃ | |

TABLE 3-continued

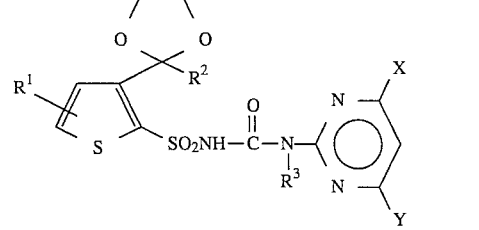

| R¹ | R² | R³ | X | Y | mp (°C.) |
|---|---|---|---|---|---|
| H | CH₂F | H | CH₃ | CH₃ | 175–178 |
| H | CH₂F | H | Cl | OCH₃ | 197– |

TABLE 3-continued

| R¹ | R² | R³ | X | Y | mp (°C.) |
|---|---|---|---|---|---|
| H | CH$_2$F | H | Br | OCH$_3$ | 201 |
| H | CH$_2$F | H | Cl | CH$_3$ | 195–199 |
| H | CH$_2$F | H | OCH$_3$ | H | |
| H | CH$_2$F | H | OCH$_3$ | CH$_2$OC$_2$H$_5$ | |
| H | CH$_2$F | H | OCF$_2$H | OCH$_3$ | |
| H | CH$_2$F | H | OCH$_3$ | CH(OCH$_3$)$_2$ | |
| H | CH$_2$F | H | CH$_3$ | OC$_2$H$_5$ | |
| H | CH$_2$F | H | CH$_3$ | CH$_2$OCH$_3$ | |
| H | CH$_2$F | H | OCH$_3$ | CH$_2$OCH$_3$ | |
| H | CH$_2$F | H | C$_2$H$_5$ | OCH$_3$ | |
| H | CH$_2$F | H | OC$_2$H$_5$ | OCH$_3$ | |
| H | CH$_2$F | H | OCH$_2$CF$_3$ | OCH$_3$ | |
| H | CH$_2$F | H | CF$_3$ | OCH$_3$ | |
| H | CH$_2$F | H | CH$_2$F | OCH$_3$ | |
| H | CH$_2$F | H | CH$_2$Cl | OCH$_3$ | |
| H | CH$_2$F | H | CH$_2$Br | OCH$_3$ | |
| H | CH$_2$F | H | F | OCH$_3$ | |
| H | CH$_2$F | H | I | OCH$_3$ | |
| H | CH$_2$F | H | OCH$_2$CH$_2$F | OCH$_3$ | |
| H | CH$_2$F | H | OCH$_2$CH$_2$CF$_3$ | OCH$_3$ | |
| H | CH$_2$F | H | OCH$_2$CHF$_2$ | CH$_3$ | |
| H | CH$_2$F | H | OCH$_2$CF$_3$ | CH$_3$ | |
| H | CH$_2$F | H | Cl | OC$_2$H$_5$ | 170–174 |
| H | CH$_2$F | H | OC$_2$H$_5$ | NHCH$_3$ | |
| H | CH$_2$F | H | OC$_2$H$_5$ | CH$_2$SCH$_3$ | |
| H | CH$_2$F | H | OCF$_2$H | CH$_3$ | |
| H | CH$_2$F | H | Cl | OCF$_2$H | |
| H | CH$_2$F | H | NH$_2$ | OC$_2$H$_5$ | |
| H | CH$_2$F | H | n-C$_3$H$_7$ | OCH$_3$ | |
| H | CH$_2$F | H | NHCH$_3$ | OCH$_3$ | |
| H | CH$_2$F | H | OCH$_3$ | SCH$_3$ | |
| H | CH$_2$F | H | OCH$_3$ | SCF$_2$H | |
| H | CH$_2$F | H | OCH$_3$ | OCH$_2$CCH | |
| H | CH$_2$F | H | OCH$_3$ | OCH$_2$CH=CH$_2$ | |
| H | CH$_2$F | H | OCH$_3$ | CCH | |
| H | CH$_2$F | H | OCH$_3$ | N(CH$_3$)$_2$ | |
| H | CH$_2$F | H | OCH$_3$ | cyclopropyl | |
| H | CH$_2$F | H | OCH$_3$ | NH$_2$ | |
| H | CH$_2$F | H | OCH$_3$ | CF$_3$ | |
| H | CH$_2$F | H | OCH$_3$ | OCH$_2$CH$_2$OCH$_3$ | |
| H | CH$_2$F | H | OCH$_3$ | CH$_2$SCH$_3$ | |
| H | CH$_2$F | H | OCH$_3$ | CHO | |
| H | CH$_2$F | H | OCH$_3$ | COCH$_3$ | |
| H | CH$_2$F | H | OCH$_3$ | CH(SCH$_3$)OC$_2$H$_5$ | |
| H | CH$_2$F | H | OCH$_3$ | C(CH$_3$)(SCH$_3$)$_2$ | |
| H | CH$_2$F | H | OCH$_3$ | C(SC$_2$H$_5$)$_2$ | |
| H | CH$_2$F | H | OCH$_3$ | 1,3-dioxolan-2-yl | |
| H | CH$_2$F | H | OCH$_3$ | 2-methyl-1,3-oxathiolan-2yl | |
| H | CH$_2$F | H | OCH$_3$ | 1,3-oxathian-2-yl | |
| H | CH$_2$F | H | OCH$_3$ | 2-methyl-1,3-dithian-2-yl | |
| H | CH$_2$F | H | OCH$_3$ | 4-methyl-1,3-dioxolan-2-yl | |
| H | CH$_2$F | H | OCH$_3$ | 2-4-dimethyl-1,3 dithiolan-2-yl | |
| H | CH$_2$F | H | OCH$_3$ | N(OCH$_3$)(CH$_3$) | |
| H | CH$_2$F | H | OCH$_3$ | CCCH$_3$ | |
| H | CH$_2$F | H | OCH$_3$ | C$_2$H$_5$ | |
| H | CH$_2$F | H | OCH$_3$ | OCF$_2$Br | |
| H | CHFCH$_3$ | H | OCH$_3$ | OC$_2$H$_5$ | |
| H | CHFCH$_3$ | H | CH$_3$ | OCH$_3$ | |
| H | CHFCH$_3$ | H | CH$_3$ | CH$_3$ | |
| H | CHFCH$_3$ | H | Cl | OCH$_3$ | |
| H | CHFCH$_3$ | H | Br | OCH$_3$ | |
| H | CHFCH$_3$ | H | CH$_3$ | H | |
| H | CHFCH$_3$ | H | OCH$_3$ | H | |
| H | CHFCH$_3$ | H | OCH$_3$ | CH$_2$OC$_2$H$_5$ | |
| H | CHFCH$_3$ | H | OCF$_2$H | OCH$_3$ | |
| H | CHFCH$_3$ | H | OCH$_3$ | CH(OCH$_3$)$_2$ | |
| H | CHFCH$_3$ | H | CH$_3$ | OC$_2$H$_5$ | |
| H | CHFCH$_3$ | H | CH$_3$ | CH$_2$OCH$_3$ | |
| H | CHFCH$_3$ | H | OCH$_3$ | CH$_2$OCH$_3$ | |
| H | CHFCH$_3$ | H | OCH$_3$ | C$_2$H$_5$ | |
| H | CHFCH$_3$ | H | OC$_2$H$_5$ | OCH$_3$ | |
| H | CHFCH$_3$ | H | OCH$_2$CF$_3$ | OCH$_3$ | |
| H | CHFCH$_3$ | H | CF$_3$ | OCH$_3$ | |
| H | CHFCH$_3$ | H | CH$_2$F | OCH$_3$ | |
| H | CHFCH$_3$ | H | CH$_2$Cl | OCH$_3$ | |
| H | CHFCH$_3$ | H | CH$_2$Br | OCH$_3$ | |
| H | CHFCH$_3$ | H | F | OCH$_3$ | |
| H | CHFCH$_3$ | H | I | OCH$_3$ | |
| H | CHFCH$_3$ | H | OCH$_2$CH$_2$F | OCH$_3$ | |
| H | CHFCH$_3$ | H | OCH$_2$CH$_2$CF$_3$ | OCH$_3$ | |
| H | CHFCH$_3$ | H | OCH$_2$CHF$_2$ | CH$_3$ | |
| H | CHFCH$_3$ | H | OCH$_2$CF$_3$ | CH$_3$ | |
| H | CHFCH$_3$ | H | Cl | OC$_2$H$_5$ | |
| H | CHFCH$_3$ | H | OC$_2$H$_5$ | NHCH$_3$ | |
| H | CHFCH$_3$ | H | OCH$_3$ | CH$_2$SCH$_3$ | |
| H | CHFCH$_3$ | H | OCF$_2$H | CH$_3$ | |
| H | CHFCH$_3$ | H | Cl | OCF$_2$H | |
| H | CH$_2$CH$_2$F | H | OCH$_3$ | OCH$_3$ | |
| H | CH$_2$CH$_2$F | H | CH$_3$ | OCH$_3$ | |
| H | CH$_2$CH$_2$F | H | CH$_3$ | CH$_3$ | |
| H | CH$_2$CH$_2$F | H | Cl | OCH$_3$ | |
| H | CH$_2$CH$_2$F | H | Br | OCH$_3$ | |
| H | CH$_2$CH$_2$F | H | CH$_3$ | H | |
| H | CH$_2$CH$_2$F | H | OCH$_3$ | H | |
| H | CH$_2$CH$_2$F | H | OCH$_3$ | CH$_2$OC$_2$H$_5$ | |
| H | CH$_2$CH$_2$F | H | OCF$_2$H | OCH$_3$ | |
| H | CH$_2$CH$_2$F | H | OCH$_3$ | CH(OCH$_3$)$_2$ | |
| H | CH$_2$CH$_2$F | H | CH$_3$ | OC$_2$H$_5$ | |
| H | CH$_2$CH$_2$F | H | CH$_3$ | CH$_2$OCH$_3$ | |
| H | CH$_2$CH$_2$F | H | OCH$_3$ | CH$_2$OCH$_3$ | |
| H | CH$_2$CH$_2$F | H | OCH$_3$ | C$_2$H$_5$ | |
| H | CH$_2$CH$_2$F | H | OC$_2$H$_5$ | OCH$_3$ | |
| H | CH$_2$CH$_2$F | H | OCH$_2$CF$_3$ | OCH$_3$ | |
| H | CH$_2$CH$_2$F | H | CF$_3$ | OCH$_3$ | |
| H | CH$_2$CH$_2$F | H | CH$_2$F | OCH$_3$ | |
| H | CH$_2$CH$_2$F | H | CH$_2$Cl | OCH$_3$ | |
| H | CH$_2$CH$_2$F | H | CH$_2$Br | OCH$_3$ | |
| H | CH$_2$CH$_2$F | H | F | OCH$_3$ | |
| H | CH$_2$CH$_2$F | H | I | OCH$_3$ | |
| H | CH$_2$CH$_2$F | H | OCH$_2$CH$_2$F | OCH$_3$ | |
| H | CH$_2$CH$_2$F | H | OCH$_2$CH$_2$CF$_3$ | OCH$_3$ | |
| H | CH$_2$CH$_2$F | H | OCH$_2$CHF$_2$ | CH$_3$ | |
| H | CH$_2$CH$_2$F | H | OCH$_2$CF$_3$ | CH$_3$ | |
| H | CH$_2$CH$_2$F | H | Cl | OC$_2$H$_5$ | |
| H | CH$_2$CH$_2$F | H | OC$_2$H$_5$ | NHCH$_3$ | |
| H | CH$_2$CH$_2$F | H | OCH$_3$ | CH$_2$SCH$_3$ | |
| H | CH$_2$CH$_2$F | H | OCF$_2$H | CH$_3$ | |
| H | CH$_2$CH$_2$F | H | Cl | OCF$_2$H | |
| H | CH$_2$Cl | H | OCH$_3$ | OCH$_3$ | |
| H | CH$_2$Cl | H | CH$_3$ | OCH$_3$ | |
| H | CH$_2$Cl | H | CH$_3$ | CH$_3$ | |

TABLE 3-continued

| R¹ | R² | R³ | X | Y | mp (°C.) |
|---|---|---|---|---|---|
| H | CH$_2$Cl | H | Cl | OCH$_3$ | |
| H | CH$_2$Cl | H | Br | OCH$_3$ | |
| H | CH$_2$Cl | H | CH$_3$ | H | |
| H | CH$_2$Cl | H | OCH$_3$ | H | |
| H | CH$_2$Cl | H | OCH$_3$ | CH$_2$OC$_2$H$_5$ | |
| H | CH$_2$Cl | H | OCF$_2$H | OCH$_3$ | |
| H | CH$_2$Cl | H | OCH$_3$ | CH(OCH$_3$)$_2$ | |
| H | CH$_2$Cl | H | CH$_3$ | OC$_2$H$_5$ | |
| H | CH$_2$Cl | H | CH$_3$ | CH$_2$OCH$_3$ | |
| H | CH$_2$Cl | H | OCH$_3$ | CH$_2$OCH$_3$ | |
| H | CH$_2$Cl | H | OCH$_3$ | C$_2$H$_5$ | |
| H | CH$_2$Cl | H | OC$_2$H$_5$ | OCH$_3$ | |
| H | CH$_2$Cl | H | OCH$_2$CF$_3$ | OCH$_3$ | |
| H | CH$_2$Cl | H | CF$_3$ | OCH$_3$ | |
| H | CH$_2$Cl | H | CH$_2$F | OCH$_3$ | |
| H | CH$_2$Cl | H | CH$_2$Cl | OCH$_3$ | |
| H | CH$_2$Cl | H | CH$_2$Br | OCH$_3$ | |
| H | CH$_2$Cl | H | F | OCH$_3$ | |
| H | CH$_2$Cl | H | I | OCH$_3$ | |
| H | CH$_2$Cl | H | OCH$_2$CH$_2$F | OCH$_3$ | |
| H | CH$_2$Cl | H | OCH$_2$CH$_2$CF$_3$ | OCH$_3$ | |
| H | CH$_2$Cl | H | OCH$_2$CHF$_2$ | CH$_3$ | |
| H | CH$_2$Cl | H | OCH$_2$CF$_3$ | CH$_3$ | |
| H | CH$_2$Cl | H | Cl | OC$_2$H$_5$ | |
| H | CH$_2$Cl | H | OC$_2$H$_5$ | NHCH$_3$ | |
| H | CH$_2$Cl | H | OCH$_3$ | CH$_2$SCH$_3$ | |
| H | CH$_2$Cl | H | OCF$_2$H | CH$_3$ | |
| H | CH$_2$Cl | H | Cl | OCF$_2$H | |
| H | CH$_2$Br | H | OCH$_3$ | OCH$_3$ | |
| H | CH$_2$Br | H | CH$_3$ | OCH$_3$ | |
| H | CH$_2$Cl | H | CH$_3$ | CH$_3$ | |
| H | CH$_2$Br | H | Cl | OCH$_3$ | |
| H | CH$_2$Br | H | Br | OCH$_3$ | |
| H | CH$_2$Br | H | CH$_3$ | H | |
| H | CH$_2$Br | H | OCH$_3$ | H | |
| H | CH$_2$Br | H | OCH$_3$ | CH$_2$OC$_2$H$_5$ | |
| H | CH$_2$Br | H | OCF$_2$H | OCH$_3$ | |
| H | CH$_2$Br | H | OCH$_3$ | CH(OCH$_3$)$_2$ | |
| H | CH$_2$Br | H | CH$_3$ | OC$_2$H$_5$ | |
| H | CH$_2$Br | H | CH$_3$ | CH$_2$OCH$_3$ | |
| H | CH$_2$Br | H | OCH$_3$ | CH$_2$OCH$_3$ | |
| H | CH$_2$Br | H | OCH$_3$ | C$_2$H$_5$ | |
| H | CH$_2$Br | H | OC$_2$H$_5$ | OCH$_3$ | |
| H | CH$_2$Br | H | OCH$_2$CF$_3$ | OCH$_3$ | |
| H | CH$_2$Br | H | CF$_3$ | OCH$_3$ | |
| H | CH$_2$Br | H | CH$_2$F | OCH$_3$ | |
| H | CH$_2$Br | H | CH$_2$Cl | OCH$_3$ | |
| H | CH$_2$Br | H | CH$_2$Br | OCH$_3$ | |
| H | CH$_2$Br | H | F | OCH$_3$ | |
| H | CH$_2$Br | H | I | OCH$_3$ | |
| H | CH$_2$Br | H | OCH$_2$CH$_2$F | OCH$_3$ | |
| H | CH$_2$Br | H | OCH$_2$CH$_2$CF$_3$ | OCH$_3$ | |
| H | CH$_2$Br | H | OCH$_2$CHF$_2$ | CH$_3$ | |
| H | CH$_2$Br | H | OCH$_2$CF$_3$ | CH$_3$ | |
| H | CH$_2$Br | H | Cl | OC$_2$H$_5$ | |
| H | CH$_2$Br | H | OC$_2$H$_5$ | NHCH$_3$ | |
| H | CH$_2$Br | H | OCH$_3$ | CH$_2$SCH$_3$ | |
| H | CH$_2$Br | H | OCF$_2$H | CH$_3$ | |
| H | CH$_2$Br | H | Cl | OCF$_2$H | |

TABLE 4

| R¹ | R² | R³ | X | Y | mp (°C.) |
|---|---|---|---|---|---|
| H | CH$_2$F | H | CH$_3$ | OCH$_3$ | 212–214 |
| H | CH$_2$F | H | OCH$_3$ | OCH$_3$ | 225–228 |
| H | CH$_2$F | H | OC$_2$H$_5$ | NHCH$_3$ | |
| H | CH$_2$F | H | OCH$_3$ | Cl | |
| H | CH$_2$F | H | OCH$_3$ | N(CH$_3$)$_2$ | |
| H | CH$_2$Cl | H | CH$_3$ | OCH$_3$ | 180–185 |
| H | CH$_2$Cl | H | OCH$_3$ | OCH$_3$ | 216–219 |
| H | CH$_2$Cl | H | OC$_2$H$_5$ | NHCH$_3$ | |
| H | CH$_2$Cl | H | OCH$_3$ | N(OCH$_3$)(CH$_3$) | |
| H | CH$_2$Cl | H | OCH$_3$ | N(CH$_3$)$_2$ | |
| H | CH$_2$Br | H | CH$_3$ | OCH$_3$ | |
| H | CH$_2$Br | H | OCH$_3$ | OCH$_3$ | |
| H | CH$_2$Br | H | OC$_2$H$_5$ | NHCH$_3$ | |
| H | CH$_2$Br | H | OCH$_3$ | N(OCH$_3$)(CH$_3$) | |
| H | CH$_2$Br | H | OCH$_3$ | N(CH$_3$)$_2$ | |
| H | CF$_3$ | H | CH$_3$ | OCH$_3$ | 205–209 |
| H | CF$_3$ | H | OCH$_3$ | OCH$_3$ | 220–223 |
| H | CHF$_2$ | H | OC$_2$H$_5$ | NHCH$_3$ | |
| H | CHF$_2$ | H | OCH$_3$ | N(OCH$_3$)(CH$_3$) | |
| H | CHF$_2$ | H | OCH$_3$ | N(CH$_3$)$_2$ | |
| H | CH$_2$F | CH$_3$ | OCH$_3$ | OCH$_3$ | |
| H | CH$_2$F | CH$_3$ | CH$_3$ | OCH$_3$ | |
| H | CH$_2$Br | CH$_3$ | OCH$_3$ | OCH$_3$ | |
| H | CH$_2$Cl | CH$_3$ | OCH$_3$ | OCH$_3$ | |
| H | CHF$_2$ | CH$_3$ | OCH$_3$ | OCH$_3$ | |
| H | CHF$_2$ | CH$_3$ | CH$_3$ | OCH$_3$ | |
| H | CHF$_2$ | CH$_3$ | OC$_2$H$_5$ | NHCH$_3$ | |
| H | CH$_2$F | CH$_3$ | OCH$_3$ | N(CH$_3$)$_2$ | |
| H | CHFCH$_3$ | H | CH$_3$ | OCH$_3$ | |
| H | CHFCH$_3$ | H | OCH$_3$ | OCH$_3$ | |
| H | CHFCH$_3$ | H | OC$_2$H$_5$ | NHCH$_3$ | |
| H | CHFCH$_3$ | H | OCH$_3$ | N(OCH$_3$)(CH$_3$) | |
| H | CHFCH$_3$ | H | OCH$_3$ | N(CH$_3$)$_2$ | |
| H | CHClCH$_3$ | H | CH$_3$ | OCH$_3$ | |
| H | CHClCH$_3$ | H | OCH$_3$ | OCH$_3$ | |
| H | CHClCH$_3$ | H | OC$_2$H$_5$ | NHCH$_3$ | |
| H | CHClCH$_3$ | H | OCH$_3$ | N(OCH$_3$)(CH$_3$) | |
| H | CHClCH$_3$ | H | OCH$_3$ | N(CH$_3$)$_2$ | |
| H | CH$_2$CH$_2$F | H | CH$_3$ | OCH$_3$ | |
| H | CH$_2$CH$_2$F | H | OCH$_3$ | OCH$_3$ | |
| H | CH$_2$CH$_2$F | H | OC$_2$H$_5$ | NHCH$_3$ | |
| H | CH$_2$CH$_2$F | H | OCH$_3$ | N(OCH$_3$)(CH$_3$) | |
| H | CH$_2$CH$_2$F | H | OCH$_3$ | N(CH$_3$)$_2$ | |
| H | CHFCl | H | OCH$_3$ | OCH$_3$ | |
| H | CHFCl | H | CH$_3$ | OCH$_3$ | |
| H | CHFCl | H | CH$_3$ | CH$_3$ | |
| H | CH$_2$Cl | H | Cl | OCH$_3$ | 219–222 |
| H | CHFCl | H | OCH$_3$ | CH$_2$OCH$_3$ | |
| H | CHFCl | H | CH$_3$ | OC$_2$H$_5$ | |
| H | CHFCl | H | OCH$_3$ | CH$_2$Cl | |
| H | CHFCl | H | F | OCH$_3$ | |
| H | CHFCl | H | OCH$_3$ | CH(OCH$_3$)$_2$ | |
| H | CHFCl | H | OCHF$_2$ | OCH$_3$ | |
| H | CHFCl | H | C$_2$H$_5$ | OCH$_3$ | |
| 5-F | CH$_2$F | H | CH$_3$ | OCH$_3$ | |

TABLE 4-continued

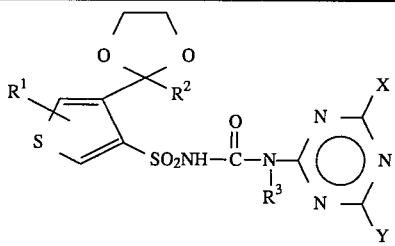

| R¹ | R² | R³ | X | Y | mp (°C.) |
|---|---|---|---|---|---|
| 5-Cl | CH₂F | H | OCH₃ | CH₃ | |
| 5-Br | CH₂F | H | CH₃ | OCH₃ | |
| 5-CH₂CN | CH₂F | H | OCH₃ | OCH₃ | |
| 5-OCH₃ | CH₂F | H | CH₃ | OCH₃ | |
| 5-SCH₃ | CH₂F | H | CH₃ | OCH₃ | |
| 5-OCF₂H | CH₂F | H | CH₃ | OCH₃ | |
| 5-Cl | CH₂Cl | H | CH₃ | OCH₃ | |
| 5-Cl | CH₂Br | H | OCH₃ | OCH₃ | |
| 5-Cl | CH₂F | H | OC₂H₅ | NHCH₃ | |
| 5-Cl | CH₂F | H | OCH₃ | OCH₃ | |

TABLE 5

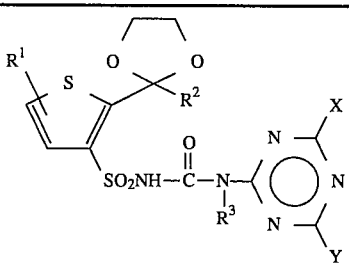

| R¹ | R² | R³ | X | Y | mp (°C.) |
|---|---|---|---|---|---|
| H | CH₂F | H | CH₃ | OCH₃ | 185–189 |
| H | CH₂F | H | OCH₃ | OCH₃ | 179–182 |
| H | CH₂F | H | OC₂H₅ | NHCH₃ | |
| H | CH₂F | H | OCH₃ | N(OCH₃)(CH₃) | |
| H | CH₂F | H | OCH₃ | N(CH₃)₂ | |
| H | CH₂Cl | H | CH₃ | OCH₃ | 173–177 |
| H | CH₂Cl | H | OCH₃ | OCH₃ | 186–190 |
| H | CH₂Cl | H | OC₂H₅ | Cl | 186–188 |
| H | CH₂Cl | H | OCH₃ | N(OCH₃)(CH₃) | |
| H | CH₂Cl | H | OCH₃ | N(CH₃)₂ | |
| H | CH₂Br | H | CH₃ | OCH₃ | |
| H | CH₂Br | H | OCH₃ | OCH₃ | |
| H | CH₂Br | H | OC₂H₅ | NHCH₃ | |
| H | CH₂Br | H | OCH₃ | N(OCH₃)(CH₃) | |
| H | CH₂Br | H | OCH₃ | N(CH₃)₂ | |
| H | CHF₂ | H | CH₃ | OCH₃ | |
| H | CHF₂ | H | OCH₃ | OCH₃ | |
| H | CHF₂ | H | OC₂H₅ | NHCH₃ | |
| H | CHF₂ | H | OCH₃ | N(OCH₃)(CH₃) | |
| H | CHF₂ | H | OCH₃ | N(CH₃)₂ | |
| H | CH₂F | CH₃ | OCH₃ | OCH₃ | |
| H | CH₂Cl | CH₃ | OCH₃ | OCH₃ | |
| H | CH₂F | CH₃ | CH₃ | OCH₃ | |
| H | CH₂Br | CH₃ | OCH₃ | OCH₃ | |
| H | CH₂Cl | CH₃ | CH₃ | OCH₃ | |
| H | CH₂Br | CH₃ | CH₃ | OCH₃ | |
| H | CHF₂ | CH₃ | OCH₃ | OCH₃ | |
| H | CHF₂ | CH₃ | CH₃ | OCH₃ | |
| H | CH₂F | CH₃ | OC₂H₅ | NHCH₃ | |
| H | CH₂F | CH₃ | OCH₃ | N(CH₃)₂ | |
| H | CHFCH₃ | H | CH₃ | OCH₃ | |
| H | CHFCH₃ | H | OCH₃ | OCH₃ | |
| H | CHFCH₃ | H | OC₂H₅ | NHCH₃ | |
| H | CHFCH₃ | H | OCH₃ | N(OCH₃)(CH₃) | |
| H | CHFCH₃ | H | OCH₃ | N(CH₃)₂ | |

TABLE 5-continued

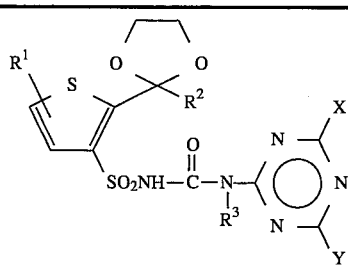

| R¹ | R² | R³ | X | Y | mp (°C.) |
|---|---|---|---|---|---|
| H | CHClCH₃ | H | CH₃ | OCH₃ | |
| H | CHClCH₃ | H | OCH₃ | OCH₃ | |
| H | CHClCH₃ | H | OC₂H₅ | NHCH₃ | |
| H | CHClCH₃ | H | OCH₃ | N(OCH₃)(CH₃) | |
| H | CHClCH₃ | H | OCH₃ | N(CH₃)₂ | |
| H | CH₂CH₂F | H | CH₃ | OCH₃ | |
| H | CH₂CH₂F | H | OCH₃ | OCH₃ | |
| H | CH₂CH₂F | H | OC₂H₅ | NHCH₃ | |
| H | CH₂CH₂F | H | OCH₃ | N(OCH₃)(CH₃) | |
| H | CH₂CH₂F | H | OCH₃ | N(CH₃)₂ | |
| H | CHFCl | H | OCH₃ | OCH₃ | |
| H | CHFCl | H | CH₃ | OCH₃ | |
| H | CHFCl | H | CH₃ | CH₃ | |
| H | CHFCl | H | Cl | OCH₃ | |
| H | CHFCl | H | OCH₃ | CH₂OCH₃ | |
| H | CHFCl | H | CH₃ | OC₂H₅ | |
| H | CHFCl | H | CH₂Cl | OCH₃ | |
| H | CHFCl | H | F | OCH₃ | |
| H | CHFCl | H | OCH₃ | CH(OCH₃)₂ | |
| H | CHFCl | H | OCHF₂ | OCH₃ | |
| H | CHFCl | H | C₂H₅ | OCH₃ | |
| 5-F | CH₂F | H | CH₃ | OCH₃ | |

TABLE 6

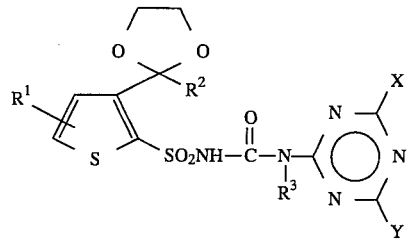

| R¹ | R² | R³ | X | Y | mp |
|---|---|---|---|---|---|
| H | CH₂F | H | CH₃ | OCH₃ | 162–167 |
| H | CH₂F | H | OCH₃ | OCH₃ | 195–198 |
| H | CH₂F | H | OC₂H₅ | NHCH₃ | |
| H | CH₂F | H | OCH₃ | N(OCH₃)(CH₃) | |
| H | CH₂F | H | OCH₃ | N(CH₃)₂ | |
| H | CH₂Cl | H | CH₃ | OCH₃ | |
| H | CH₂Cl | H | OCH₃ | OCH₃ | |
| H | CH₂Cl | H | OC₂H₅ | NHCH₃ | |
| H | CH₂Cl | H | OCH₃ | N(OCH₃)(CH₃) | |
| H | CH₂Cl | H | OCH₃ | N(CH₃)₂ | |
| H | CH₂Br | H | CH₃ | OCH₃ | |
| H | CH₂Br | H | OCH₃ | OCH₃ | |
| H | CH₂Br | H | OCH₂H₅ | NHCH₃ | |
| H | CH₂Br | H | OCH₃ | N(OCH₃)(CH₃) | |
| H | CH₂Br | H | OCH₃ | N(CH₃)₂ | |
| H | CHF₂ | H | CH₃ | OCH₃ | |
| H | CHF₂ | H | OCH₃ | OCH₃ | |
| H | CHF₂ | H | OC₂H₅ | NHCH₃ | |
| H | CHF₂ | H | OCH₃ | N(OCH₃)(CH₃) | |
| H | CHF₂ | H | OCH₃ | N(CH₃)₂ | |
| H | CH₂F | CH₃ | OCH₃ | OCH₃ | |
| H | CH₂Cl | CH₃ | OCH₃ | OCH₃ | |
| H | CH₂F | CH₃ | CH₃ | OCH₃ | |
| H | CH₂Br | CH₃ | OCH₃ | OCH₃ | |

TABLE 6-continued

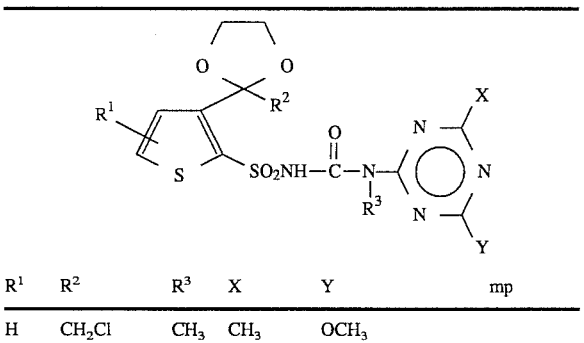

| R¹ | R² | R³ | X | Y | mp |
|---|---|---|---|---|---|
| H | CH₂Cl | CH₃ | CH₃ | OCH₃ | |
| H | CH₂Br | CH₃ | CH₃ | OCH₃ | |

TABLE 7

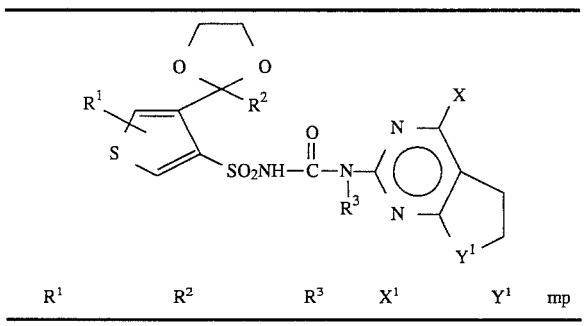

| R¹ | R² | R³ | X¹ | Y¹ | mp |
|---|---|---|---|---|---|
| H | CH₂F | H | CH₃ | O | |
| H | CH₂F | H | OCH₃ | O | |
| H | CH₂F | H | OC₂H₅ | O | |
| H | CH₂F | H | OCF₂H | O | |
| H | CH₂F | H | OCH₃ | CH₂ | |
| H | CH₂Cl | H | CH₃ | O | |
| H | CH₂Cl | H | OCH₃ | O | |
| H | CH₂Br | H | CH₃ | O | |
| H | CHFCH₃ | H | CH₃ | O | |
| H | CHClCH₃ | H | CH₃ | O | |
| 5-CH₃ | CH₂F | H | CH₃ | O | |
| 5-Cl | CH₂F | H | CH₃ | O | |
| 5-CH₃ | CH₂F | H | CH₃ | O | |
| 5-CH₂CN | CH₂F | H | CH₃ | O | |
| H | CH₂F | CH₃ | CH₃ | O | |
| H | CHF₂ | H | OCH₃ | O | |

TABLE 8

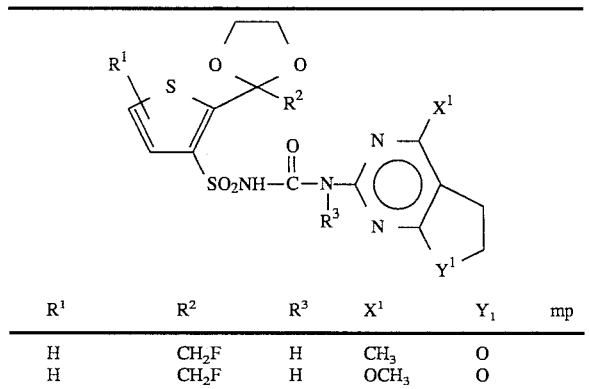

| R¹ | R² | R³ | X¹ | Y₁ | mp |
|---|---|---|---|---|---|
| H | CH₂F | H | CH₃ | O | |
| H | CH₂F | H | OCH₃ | O | |

TABLE 8-continued

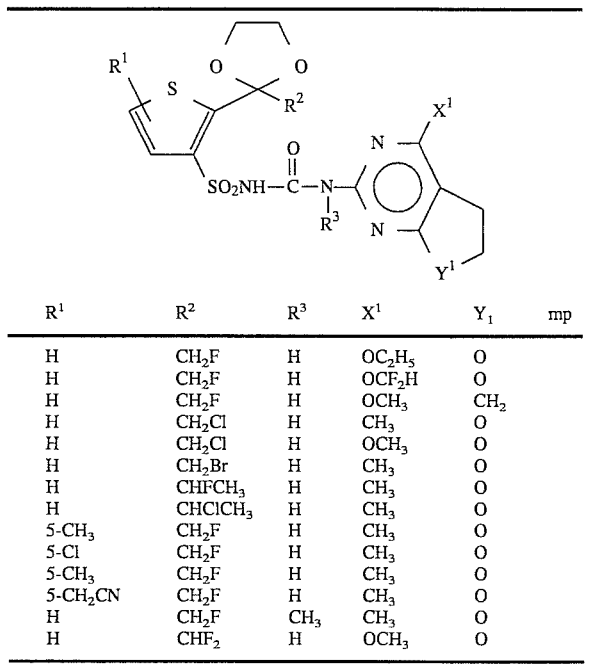

| R¹ | R² | R³ | X¹ | Y₁ | mp |
|---|---|---|---|---|---|
| H | CH₂F | H | OC₂H₅ | O | |
| H | CH₂F | H | OCF₂H | O | |
| H | CH₂F | H | OCH₃ | CH₂ | |
| H | CH₂Cl | H | CH₃ | O | |
| H | CH₂Cl | H | OCH₃ | O | |
| H | CH₂Br | H | CH₃ | O | |
| H | CHFCH₃ | H | CH₃ | O | |
| H | CHClCH₃ | H | CH₃ | O | |
| 5-CH₃ | CH₂F | H | CH₃ | O | |
| 5-Cl | CH₂F | H | CH₃ | O | |
| 5-CH₃ | CH₂F | H | CH₃ | O | |
| 5-CH₂CN | CH₂F | H | CH₃ | O | |
| H | CH₂F | CH₃ | CH₃ | O | |
| H | CHF₂ | H | OCH₃ | O | |

TABLE 9

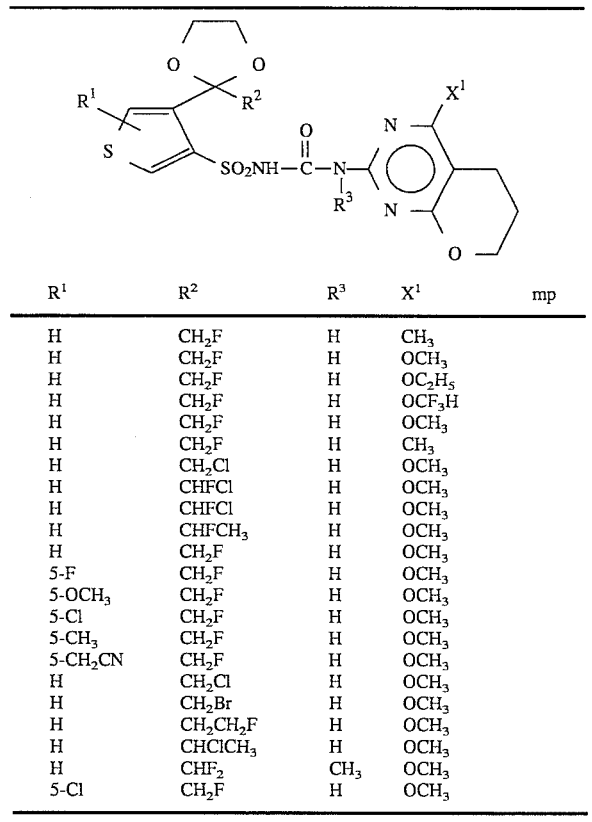

| R¹ | R² | R³ | X¹ | mp |
|---|---|---|---|---|
| H | CH₂F | H | CH₃ | |
| H | CH₂F | H | OCH₃ | |
| H | CH₂F | H | OC₂H₅ | |
| H | CH₂F | H | OCF₃H | |
| H | CH₂F | H | OCH₃ | |
| H | CH₂F | H | CH₃ | |
| H | CH₂Cl | H | OCH₃ | |
| H | CHFCl | H | OCH₃ | |
| H | CHFCl | H | OCH₃ | |
| H | CHFCH₃ | H | OCH₃ | |
| H | CH₂F | H | OCH₃ | |
| 5-F | CH₂F | H | OCH₃ | |
| 5-OCH₃ | CH₂F | H | OCH₃ | |
| 5-Cl | CH₂F | H | OCH₃ | |
| 5-CH₃ | CH₂F | H | OCH₃ | |
| 5-CH₂CN | CH₂F | H | OCH₃ | |
| H | CH₂Cl | H | OCH₃ | |
| H | CH₂Br | H | OCH₃ | |
| H | CH₂CH₂F | H | OCH₃ | |
| H | CHClCH₃ | H | OCH₃ | |
| H | CHF₂ | CH₃ | OCH₃ | |
| 5-Cl | CH₂F | H | OCH₃ | |

TABLE 10

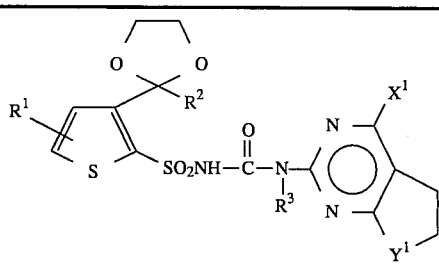

| R¹ | R² | R³ | X¹ | Y¹ | mp |
|---|---|---|---|---|---|
| H | $CH_2F$ | H | $CH_3$ | O | |
| H | $CH_2F$ | H | $OCH_3$ | O | |
| H | $CH_2F$ | H | $OC_2H_5$ | O | |
| H | $CH_2F$ | H | $OCF_2H$ | O | |
| H | $CH_2F$ | H | $OCH_3$ | $CH_2$ | |
| H | $CH_2Cl$ | H | $C_3$ | O | |
| H | $CH_2Cl$ | H | $OCH_3$ | O | |
| H | $CH_2Br$ | H | $CH_3$ | O | |
| H | $CHFCH_3$ | H | $CH_3$ | O | |
| H | $CHClCH_3$ | H | $CH_3$ | O | |
| 5-$CH_3$ | $CH_2F$ | H | $CH_3$ | O | |
| 5-Cl | $CH_2F$ | H | $CH_3$ | O | |
| 5-$CH_3$ | $CH_2F$ | H | $CH_3$ | O | |
| 5-$CH_2CN$ | $CH_2F$ | H | $CH_3$ | O | |
| H | $CH_2F$ | H | $CH_3$ | O | |
| H | $CHF_2$ | H | $OCH_3$ | O | |

TABLE 11

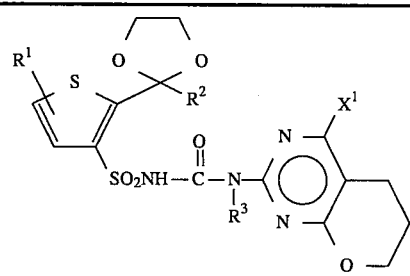

| R¹ | R² | R³ | X¹ | mp |
|---|---|---|---|---|
| H | $CH_2F$ | H | $CH_3$ | |
| H | $CH_2F$ | H | $OCH_3$ | |
| H | $CH_2F$ | H | $OC_2H_5$ | |
| H | $CH_2F$ | H | $OCF_2H$ | |
| H | $CH_2F$ | H | $OCH_3$ | |
| H | $CH_2F$ | H | $CH_3$ | |
| H | $CH_2Cl$ | H | $OCH_3$ | |
| H | CHFCl | H | $OCH_3$ | |
| H | CHFCl | H | $OCH_3$ | |
| H | $CHFCH_3$ | H | $OCH_3$ | |
| H | $CH_2F$ | H | $OCH_3$ | |
| 5-F | $CH_2F$ | H | $OCH_3$ | |
| 5-$OCH_3$ | $CH_2F$ | H | $OCH_3$ | |
| 5-Cl | $CH_2F$ | H | $OCH_3$ | |
| 5-$CH_3$ | $CH_2F$ | H | $OCH_3$ | |
| 5-$CH_2CN$ | $CH_2F$ | H | $OCH_3$ | |
| H | $CH_2Cl$ | H | $OCH_3$ | |
| H | $CH_2Br$ | H | $OCH_3$ | |
| H | $CH_2CH_2F$ | H | $OCH_3$ | |
| H | $CHClCH_3$ | H | $OCH_3$ | |
| H | $CHF_2$ | H | $OCH_3$ | |
| 4-Cl | $CH_2F$ | H | $OCH_3$ | |

TABLE 12

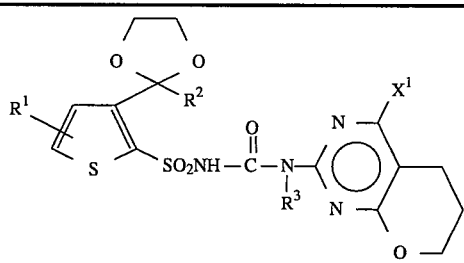

| R¹ | R² | R³ | X¹ | mp |
|---|---|---|---|---|
| H | $CH_2F$ | H | $CH_3$ | |
| H | $CH_2F$ | H | $OCH_3$ | |
| H | $CH_2F$ | H | $OC_2H_5$ | |
| H | $CH_2F$ | H | $OCF_2H$ | |
| H | $CH_2Cl$ | H | $CH_3$ | |
| H | $CH_2Cl$ | H | $OCH_3$ | |
| H | $CH_2Br$ | H | $CH_3$ | |
| H | $CHF_2$ | H | $CH_3$ | |
| H | $CHF_2$ | H | $OCH_3$ | |
| H | $CHFCH_3$ | H | $CH_3$ | |
| H | $CHFCH_3$ | H | $OCH_3$ | |
| H | CHFCl | H | $OCH_3$ | |
| H | CHFCl | H | $CH_3$ | |
| 5-Cl | CHFCl | H | $CH_3$ | |
| 5-Cl | CHFCl | H | $OCH_3$ | |
| 5-Cl | $CH_2F$ | H | $CH_3$ | |
| 5-Cl | $CH_2F$ | H | $OCH_3$ | |
| 5-$CH_3$ | $CH_2F$ | H | $CH_3$ | |
| 5-$OCH_3$ | $CH_2F$ | H | $CH_3$ | |
| H | $CH_2F$ | $CH_3$ | $CH_3$ | |
| H | $CH_2F$ | $CH_3$ | $OCH_3$ | |
| H | $CHClCH_3$ | H | $OCH_3$ | |
| H | $CH_2CH_2F$ | H | $OCH_3$ | |

TABLE 13

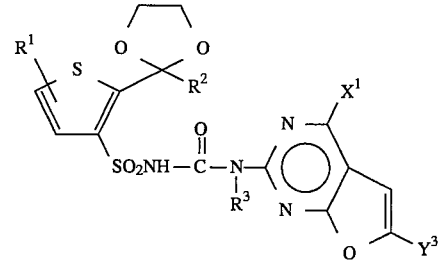

| R¹ | R² | R³ | X¹ | Y³ | mp |
|---|---|---|---|---|---|
| H | $CH_2F$ | H | $CH_3$ | $CH_3$ | |
| H | $CH_2F$ | H | $OCH_3$ | $CH_3$ | |
| H | $CH_2F$ | H | $OC_2H_5$ | $CH_3$ | |
| H | $CH_2F$ | H | $OCF_2H$ | $CH_3$ | |
| H | $CH_2F$ | H | $OCH_3$ | H | |
| H | $CH_2F$ | H | $CH_3$ | H | |
| H | $CH_2Cl$ | H | $OCH_3$ | $OCH_3$ | |
| H | CHFCl | H | $OCH_3$ | $OCH_3$ | |
| H | CHFCl | H | $OCH_3$ | $CH_3$ | |
| H | $CHFCH_3$ | H | $OCH_3$ | $OCH_3$ | |
| H | $CH_2F$ | H | $OCH_3$ | $OCH_3$ | |
| 5-F | $CH_2F$ | H | $OCH_3$ | $OCH_3$ | |
| 5-$OCH_3$ | $CH_2F$ | H | $OCH_3$ | $OCH_3$ | |
| 5-Cl | $CH_2F$ | H | $OCH_3$ | $OCH_3$ | |
| 5-$CH_3$ | $CH_2F$ | H | $OCH_3$ | $OCH_3$ | |
| 5-$CH_3$ | $CH_2F$ | H | $OCH_3$ | $CH_3$ | |
| H | $CH_2Cl$ | H | $OCH_3$ | $CH_3$ | |
| H | $CH_2Br$ | H | $OCH_3$ | $CH_3$ | |
| H | $CH_2CH_2F$ | H | $OCH_3$ | $CH_3$ | |
| H | $CHClCH_3$ | H | $OCH_3$ | $CH_3$ | |
| H | $CHF_2$ | H | $OCH_3$ | $CH_3$ | |

TABLE 13-continued

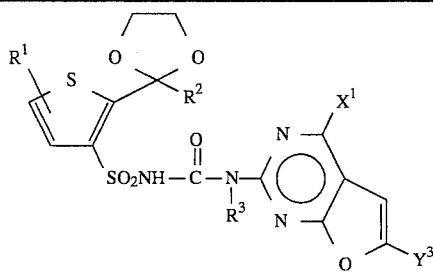

| R¹ | R² | R³ | X¹ | Y³ | mp |
|---|---|---|---|---|---|
| 5-Cl | CH₂F | H | OCH₃ | CH₃ | |

TABLE 14

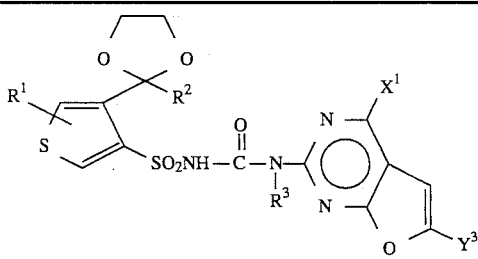

| R¹ | R² | R³ | X¹ | Y³ | mp |
|---|---|---|---|---|---|
| H | CH₂F | H | CH₃ | CH₃ | |
| H | CH₂F | H | OCH₃ | CH₃ | |
| H | CH₂F | H | OC₂H₅ | CH₃ | |
| H | CH₂F | H | OCF₂H | CH₃ | |
| H | CH₂F | H | OCH₃ | H | |
| H | CH₂F | H | CH₃ | H | |
| H | CH₂Cl | H | OCH₃ | OCH₃ | |
| H | CHFCl | H | OCH₃ | OCH₃ | |
| H | CHFCl | H | OCH₃ | CH₃ | |
| H | CHFCH₃ | H | OCH₃ | OCH₃ | |
| 5-F | CH₂F | H | OCH₃ | OCH₃ | |
| 5-OCH₃ | CH₂F | H | OCH₃ | OCH₃ | |
| 5-Cl | CH₂F | H | OCH₃ | OCH₃ | |
| 5-CH₃ | CH₂F | H | OCH₃ | OCH₃ | |
| 5-CH₂CN | CH₂F | H | OCH₃ | CH₃ | |
| H | CH₂Cl | H | OCH₃ | CH₃ | |
| H | CH₂Br | H | OCH₃ | CH₃ | |
| H | CH₂CH₂F | H | OCH₃ | CH₃ | |
| H | CHClCH₃ | H | OCH₃ | CH₃ | |
| H | CHF₂ | H | OCH₃ | CH₃ | |
| 5-Cl | CH₂F | H | OCH₃ | CH₃ | |

TABLE 15

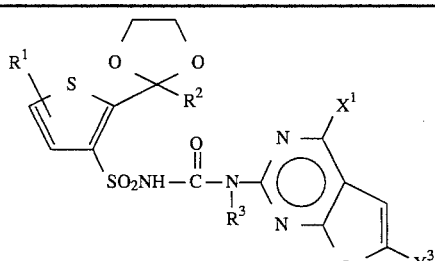

| R¹ | R² | R³ | X¹ | Y³ | mp |
|---|---|---|---|---|---|
| H | CH₂F | H | CH₃ | CH₃ | |

TABLE 15-continued

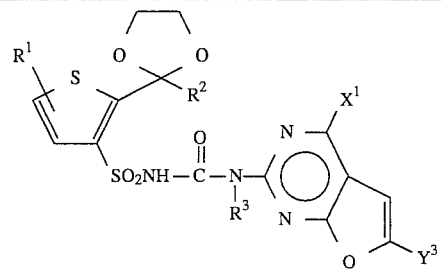

| R¹ | R² | R³ | X¹ | Y³ | mp |
|---|---|---|---|---|---|
| H | CH₂F | H | OCH₃ | CH₃ | |
| H | CH₂F | H | OC₂H₅ | CH₃ | |
| H | CH₂F | H | OCF₂H | CH₃ | |
| H | CH₂F | H | OCH₃ | H | |
| H | CH₂F | H | CH₃ | H | |
| H | CH₂Cl | H | OCH₃ | OCH₃ | |
| H | CHFCl | H | OCH₃ | OCH₃ | |
| H | CHFCl | H | OCH₃ | CH₃ | |
| H | CHFCH₃ | H | OCH₃ | OCH₃ | |
| H | CH₂F | H | OCH₃ | OCH₃ | |
| 5-F | CH₂F | H | OCH₃ | OCH₃ | |
| 5-OCH₃ | CH₂F | H | OCH₃ | OCH₃ | |
| 5-Cl | CH₂F | H | OCH₃ | OCH₃ | |
| 5-CH₃ | CH₂F | H | OCH₃ | OCH₃ | |
| 5-CH₂CN | CH₂F | H | OCH₃ | CH₃ | |
| H | CH₂Cl | H | OCH₃ | CH₃ | |
| H | CH₂Br | H | OCH₃ | CH₃ | |
| H | CH₂CH₂F | H | OCH₃ | CH₃ | |
| H | CHClCH₃ | H | OCH₃ | CH₃ | |
| H | CHF₂ | H | OCH₃ | CH₃ | |
| 5-Cl | CH₂F | H | OCH₃ | CH₃ | |

TABLE 16

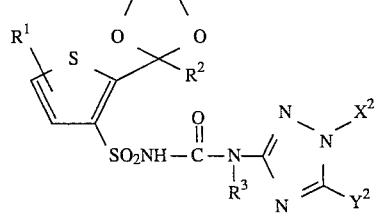

| R¹ | R² | R³ | X² | Y² | mp |
|---|---|---|---|---|---|
| H | CH₂F | H | CH₃ | OCH₃ | |
| H | CH₂F | H | CH₃ | OC₂H₅ | |
| H | CH₂F | H | CH₃ | SCH₃ | |
| H | CH₂F | H | CH₃ | SC₂H₅ | |
| H | CH₂F | H | CH₃ | CH₃ | |
| H | CH₂F | H | CH₃ | C₂H₅ | |
| H | CH₂F | H | C₂H₅ | OCH₃ | |
| H | CH₂F | H | CH₂CF₃ | OCH₃ | |
| H | CH₂Cl | H | CH₃ | OCH₃ | |
| H | CHFCl | H | CH₃ | OCH₃ | |
| H | CHF₂ | H | CH₃ | OCH₃ | |
| 5-CH₃ | CH₂F | H | CH₃ | OCH₃ | |
| 5-F | CH₂F | H | CH₃ | OCH₃ | |
| 5-Cl | CH₂F | H | CH₃ | OCH₃ | |
| 5-OCH₃ | CH₂F | H | CH₃ | OCH₃ | |
| 5-Cl | CH₂F | H | CH₃ | CH₃ | |
| 5-CH₂CN | CH₂F | H | CH₃ | OCH₃ | |
| H | CH₂Br | H | CH₃ | OCH₃ | |
| H | CH₂CH₂F | H | CH₃ | OCH₃ | |
| H | CHFCl | H | CH₃ | CH₃ | |
| H | CHFCH₃ | H | CH₃ | OCH₃ | |
| H | CHClCH₃ | H | CH₃ | OCH₃ | |

TABLE 17

| R¹ | R² | R³ | X² | Y² | mp |
|---|---|---|---|---|---|
| H | CH₂F | H | CH₃ | OCH₃ | |
| H | CH₂F | H | CH₃ | OC₂H₅ | |
| H | CH₂F | H | CH₃ | SCH₃ | |
| H | CH₂F | H | CH₃ | SC₂H₅ | |
| H | CH₂F | H | CH₃ | CH₃ | |
| H | CH₂F | H | CH₃ | C₂H₅ | |
| H | CH₂F | H | C₂H₅ | OCH₃ | |
| H | CH₂F | H | CH₂CF₃ | OCH₃ | |
| H | CH₂Cl | H | CH₃ | OCH₃ | |
| H | CHFCl | H | CH₃ | OCH₃ | |
| H | CHF₂ | H | CH₃ | OCH₃ | |
| 5-CH₃ | CH₂F | H | CH₃ | OCH₃ | |
| 5-F | CH₂F | H | CH₃ | OCH₃ | |
| 5-Cl | CH₂F | H | CH₃ | OCH₃ | |
| 5-OCH₃ | CH₂F | H | CH₃ | OCH₃ | |
| 5-Cl | CH₂F | H | CH₃ | CH₃ | |
| 5-CH₂CN | CH₂F | H | CH₃ | OCH₃ | |
| H | CH₂Br | H | CH₃ | OCH₃ | |
| H | CH₂CH₂F | H | CH₃ | OCH₃ | |
| H | CHFCl | H | CH₃ | CH₃ | |
| H | CHFCH₃ | H | CH₃ | OCH₃ | |
| H | CHClCH₃ | H | CH₃ | OCH₃ | |

TABLE 18

| R¹ | R² | R³ | X² | Y² | mp |
|---|---|---|---|---|---|
| H | CH₂F | H | CH₃ | OCH₃ | |
| H | CH₂F | H | CH₃ | OC₂H₅ | |
| H | CH₂F | H | CH₃ | SCH₃ | |
| H | CH₂F | H | CH₃ | SC₂H₅ | |
| H | CH₂F | H | CH₃ | CH₃ | |
| H | CH₂F | H | CH₃ | C₂H₅ | |
| H | CH₂F | H | C₂H₅ | OCH₃ | |
| H | CH₂F | H | CH₂CF₃ | OCH₃ | |
| H | CH₂Cl | H | CH₃ | OCH₃ | |
| H | CHFCl | H | CH₃ | OCH₃ | |
| H | CHF₂ | H | CH₃ | OCH₃ | |
| 5-CH₃ | CH₂F | H | CH₃ | OCH₃ | |
| 5-F | CH₂F | H | CH₃ | OCH₃ | |
| 5-Cl | CH₂F | H | CH₃ | OCH₃ | |
| 5-OCH₃ | CH₂F | H | CH₃ | OCH₃ | |
| 5-Cl | CH₂F | H | CH₃ | CH₃ | |
| 5-CH₂CN | CH₂F | H | CH₃ | OCH₃ | |
| H | CH₂Br | H | CH₃ | OCH₃ | |
| H | CH₂CH₂F | H | CH₃ | OCH₃ | |
| H | CHFCl | H | CH₃ | CH₃ | |
| H | CHFCH₃ | H | CH₃ | OCH₃ | |
| H | CHClCH₃ | H | CH₃ | OCH₃ | |

TABLE 19

| R¹ | R² | R³ | X³ | mp |
|---|---|---|---|---|
| H | CH₂F | H | CH₃ | |
| H | CH₂F | H | OCH₃ | |
| H | CH₂Cl | H | CH₃ | |
| H | CH₂Cl | H | OCH₃ | |
| H | CHF₂ | H | OCH₃ | |
| H | CHF₂ | H | CH₃ | |
| H | CHFCl | H | CH₃ | |
| H | CHFCl | H | OCH₃ | |
| H | CHFCH₃ | H | CH₃ | |
| H | CHFCH₃ | H | OCH₃ | |
| H | CHClCH₃ | H | OCH₃ | |
| 5-F | CH₂F | H | OCH₃ | |
| 5-Cl | CH₂F | H | OCH₃ | |
| 5-CH₃ | CH₂F | H | OCH₃ | |
| 5-OHC₃ | CH₂F | H | CH₃ | |
| 5-CH₂CN | CH₂F | H | CH₃ | |
| 5-Cl | CH₂F | H | OCH₃ | |
| H | CH₂CH₂F | H | OCH₃ | |
| H | CH₂F | CH₃ | OCH₃ | |
| H | CH₂CH₂F | H | CH₃ | |

TABLE 20

| R¹ | R² | R³ | X³ | mp |
|---|---|---|---|---|
| H | CH₂F | H | CH₃ | |
| H | CH₂F | H | OCH₃ | |
| H | CH₂Cl | H | CH₃ | |
| H | CH₂Cl | H | OCH₃ | |
| H | CHF₂ | H | OCH₃ | |
| H | CHF₂ | H | CH₃ | |
| H | CHFCl | H | CH₃ | |
| H | CHFCl | H | OCH₃ | |
| H | CHFCH₃ | H | CH₃ | |
| H | CHFCH₃ | H | OCH₃ | |
| H | CHClCH₃ | H | OCH₃ | |
| 5-F | CH₂F | H | OCH₃ | |
| 5-Cl | CH₂F | H | OCH₃ | |
| 5-CH₃ | CH₂F | H | OCH₃ | |
| 5-OCH₃ | CH₂F | H | CH₃ | |
| 5-CH₂CN | CH₂F | H | CH₃ | |
| 5-Cl | CH₂F | H | OCH₃ | |
| H | CH₂CH₂F | H | OCH₃ | |
| H | CH₂F | CH₃ | OCH₃ | |
| H | CH₂CH₂F | H | CH₃ | |

TABLE 21

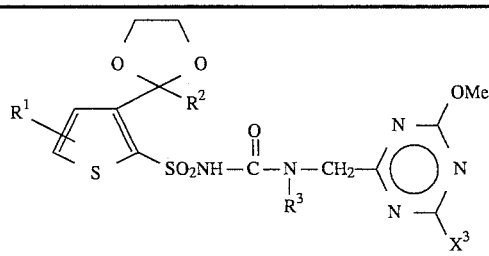

| R¹ | R² | R³ | X³ | mp |
|---|---|---|---|---|
| H | CH₂F | H | CH₃ | |
| H | CH₂F | H | OCH₃ | |
| H | CH₂Cl | H | CH₃ | |
| H | CH₂Cl | H | OCH₃ | |
| H | CHF₂ | H | OCH₃ | |
| H | CHF₂ | H | CH₃ | |
| H | CHFCl | H | CH₃ | |
| H | CHFCl | H | OCH₃ | |
| H | CHFCH₃ | H | CH₃ | |
| H | CHFCH₃ | H | OCH₃ | |
| H | CHClCH₃ | H | OCH₃ | |
| 5-F | CH₂F | H | OCH₃ | |
| 5-Cl | CH₂F | H | OCH₃ | |
| 5-CH₃ | CH₂F | H | CH₃ | |
| 5-OCH₃ | CH₂F | H | CH₃ | |
| 5-CH₂CN | CH₂F | H | CH₃ | |
| 5-Cl | CH₂F | H | OCH₃ | |
| H | CH₂CH₂F | H | OCH₃ | |
| H | CH₂F | CH₃ | OCH₃ | |
| H | CH₂CH₂F | H | CH₃ | |

TABLE 22

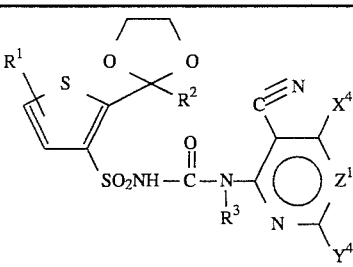

| R¹ | R² | R³ | X⁴ | Y⁴ | Z¹ | mp |
|---|---|---|---|---|---|---|
| H | CH₂F | H | CH₃ | CH₃ | CH | |
| H | CH₂F | H | CH₃ | CH₃ | N | |
| H | CH₂F | H | OCH₃ | CH₃ | CH | |
| H | CH₂F | H | OCH₃ | CH₃ | N | |
| H | CH₂F | H | OCH₃ | OCH₃ | CH | |
| H | CH₂F | H | OCH₃ | OCH₃ | N | |
| H | CH₂F | H | Cl | CH₃ | CH | |
| H | CH₂F | H | OCH₃ | Cl | CH | |
| H | CH₂F | H | OC₂H₅ | CH₃ | CH | |
| H | CH₂F | H | CH₂OCH₃ | CH₃ | N | |
| H | CH₂F | H | CH₂OCH₃ | OCH₃ | CH | |
| H | CH₂F | H | OC₂H₅ | OC₂H₅ | N | |
| H | CH₂Cl | H | OCH₃ | CH₃ | CH | |
| H | CH₂Cl | H | OCH₃ | OCH₃ | CH | |
| H | CH₂Cl | H | OCH₃ | CH₃ | N | |
| H | CH₂Cl | H | OCH₃ | OCH₃ | N | |
| H | CHF₂ | H | OCH₃ | CH₃ | CH | |
| H | CHFCl | H | OCH₃ | CH₃ | CH | |
| H | CHFCH₃ | H | OCH₃ | CH₃ | CH | |
| H | CHClCH₃ | H | OCH₃ | CH₃ | CH | |
| 5-F | CH₂F | H | OCH₃ | CH₃ | CH | |

TABLE 22-continued

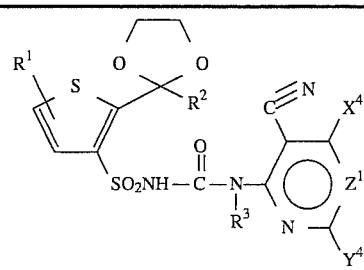

| R¹ | R² | R³ | X⁴ | Y⁴ | Z¹ | mp |
|---|---|---|---|---|---|---|
| 5-CH₃ | CH₂F | H | OCH₃ | CH₃ | CH | |
| 5-OCH₃ | CH₂F | H | OCH₃ | CH₃ | CH | |
| 5-Cl | CH₂F | H | OCH₃ | CH₃ | CH | |
| 5-CH₂CN | CH₂F | H | OCH₃ | CH₃ | CH | |
| H | CH₂F | CH₃ | OCH₃ | CH₃ | CH | |
| H | CH₂CH₂F | H | OCH₃ | CH₃ | CH | |
| H | CH₂CH₂Cl | H | OCH₃ | CH₃ | CH | |
| H | CHFCl | H | OCH₃ | OCH₃ | CH | |

TABLE 23

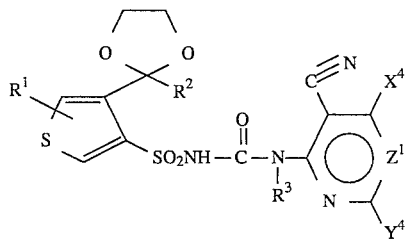

| R¹ | R² | R³ | X⁴ | Y⁴ | Z¹ | mp |
|---|---|---|---|---|---|---|
| H | CH₂F | H | CH₃ | CH₃ | CH | |
| H | CH₂F | H | CH₃ | CH₃ | N | |
| H | CH₂F | H | OCH₃ | CH₃ | CH | |
| H | CH₂F | H | OCH₃ | CH₃ | N | |
| H | CH₂F | H | OCH₃ | OCH₃ | CH | |
| H | CH₂F | H | OCH₃ | OCH₃ | N | |
| H | CH₂F | H | Cl | CH₃ | CH | |
| H | CH₂F | H | OCH₃ | Cl | CH | |
| H | CH₂F | H | OC₂H₅ | CH₃ | CH | |
| H | CH₂F | H | CH₂OCH₃ | CH₃ | N | |
| H | CH₂F | H | CH₂OCH₃ | OCH₃ | CH | |
| H | CH₂F | H | OC₂H₅ | OC₂H₅ | N | |
| H | CH₂Cl | H | OCH₃ | CH₃ | CH | |
| H | CH₂Cl | H | OCH₃ | OCH₃ | CH | |
| H | CH₂Cl | H | OCH₃ | CH₃ | N | |
| H | CH₂Cl | H | OCH₃ | OCH₃ | N | |
| H | CHF₂ | H | OCH₃ | CH₃ | CH | |
| H | CHFCl | H | OCH₃ | CH₃ | CH | |
| H | CHFCH₃ | H | OCH₃ | CH₃ | CH | |
| H | CHClCH₃ | H | OCH₃ | CH₃ | CH | |
| 5-F | CH₂F | H | OCH₃ | CH₃ | CH | |
| 5-CH₃ | CH₂F | H | OCH₃ | CH₃ | CH | |
| 5-OCH₃ | CH₂F | H | OCH₃ | CH₃ | CH | |
| 5-Cl | CH₂F | H | OCH₃ | CH₃ | CH | |
| 5-CH₂CN | CH₂F | H | OCH₃ | CH₃ | CH | |
| H | CH₂F | CH₃ | OCH₃ | CH₃ | CH | |
| H | CH₂CH₂F | H | OCH₃ | CH₃ | CH | |
| H | CH₂CH₂Cl | H | OCH₃ | CH₃ | CH | |
| H | CHFCl | H | OCH₃ | OCH₃ | CH | |

TABLE 24

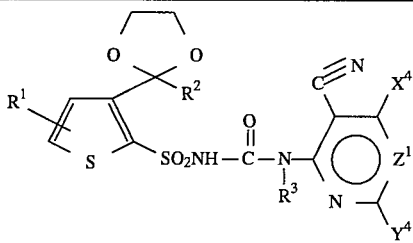

| R¹ | R² | R³ | X⁴ | Y⁴ | Z¹ | mp |
|---|---|---|---|---|---|---|
| H | $CH_2F$ | H | $CH_3$ | $CH_3$ | CH | |
| H | $CH_2F$ | H | $CH_3$ | $CH_3$ | N | |
| H | $CH_2F$ | H | $OCH_3$ | $CH_3$ | CH | |
| H | $CH_2F$ | H | $OCH_3$ | $CH_3$ | N | |
| H | $CH_2F$ | H | $OCH_3$ | $OCH_3$ | CH | |
| H | $CH_2F$ | H | $OCH_3$ | $OCH_3$ | N | |
| H | $CH_2F$ | H | Cl | $CH_3$ | CH | |
| H | $CH_2F$ | H | $OCH_3$ | Cl | CH | |
| H | $CH_2F$ | H | $OC_2H_5$ | $CH_3$ | CH | |
| H | $CH_2F$ | H | $CH_2OCH_3$ | $CH_3$ | N | |
| H | $CH_2F$ | H | $CH_2OCH_3$ | $OCH_3$ | CH | |
| H | $CH_2F$ | H | $OC_2H_5$ | $OC_2H_5$ | N | |
| H | $CH_2Cl$ | H | $OCH_3$ | $CH_3$ | CH | |
| H | $CH_2Cl$ | H | $OCH_3$ | $OCH_3$ | CH | |
| H | $CH_2Cl$ | H | $OCH_3$ | $CH_3$ | N | |
| H | $CH_2Cl$ | H | $OCH_3$ | $OCH_3$ | N | |
| H | $CHF_2$ | H | $OCH_3$ | $CH_3$ | CH | |
| H | $CHFCl$ | H | $OCH_3$ | $CH_3$ | CH | |
| H | $CHFCH_3$ | H | $OCH_3$ | $CH_3$ | CH | |
| H | $CHClCH_3$ | H | $OCH_3$ | $CH_3$ | CH | |
| 5-F | $CH_2F$ | H | $OCH_3$ | $CH_3$ | CH | |
| 5-$CH_3$ | $CH_2F$ | H | $OCH_3$ | $CH_3$ | CH | |
| 5-$OCH_3$ | $CH_2F$ | H | $OCH_3$ | $CH_3$ | CH | |
| 5-Cl | $CH_2F$ | H | $OCH_3$ | $CH_3$ | CH | |
| 5-$CH_2CN$ | $CH_2F$ | H | $OCH_3$ | $CH_3$ | CH | |
| H | $CH_2F$ | $CH_3$ | $OCH_3$ | $CH_3$ | CH | |
| H | $CH_2CH_2F$ | H | $OCH_3$ | $CH_3$ | CH | |
| H | $CH_2CH_2Cl$ | H | $OCH_3$ | $CH_3$ | CH | |
| H | $CHFCl$ | H | $OCH_3$ | $OCH_3$ | CH | |

TABLE 25

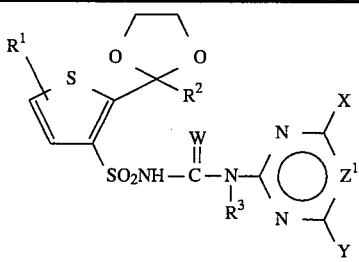

| R¹ | R² | R³ | W | X | Y | Z¹ | mp |
|---|---|---|---|---|---|---|---|
| H | $CH_2F$ | H | S | $OCH_3$ | $OCH_3$ | CH | |
| H | $CH_2F$ | H | S | $CH_3$ | $OCH_3$ | N | |
| H | $CH_2F$ | H | S | $OCH_3$ | $OCH_3$ | N | |
| H | $CH_2Cl$ | H | S | $OCH_3$ | $OCH_3$ | CH | |
| H | $CH_2Br$ | H | S | $OCH_3$ | $OCH_3$ | CH | |
| H | $CHF_2$ | H | S | $OCH_3$ | $OCH_3$ | CH | |
| H | $CHFCl$ | H | S | $OCH_3$ | $OCH_3$ | CH | |
| H | $CHFCH_3$ | H | S | $OCH_3$ | $OCH_3$ | CH | |
| H | $CHClCH_3$ | H | S | $OCH_3$ | $OCH_3$ | CH | |
| 5-$OCH_3$ | $CH_2F$ | H | S | $OCH_3$ | $OCH_3$ | CH | |
| 5-Cl | $CH_2F$ | H | S | $OCH_3$ | $OCH_3$ | CH | |
| H | $CH_2F$ | $CH_3$ | S | $OCH_3$ | $OCH_3$ | CH | |
| H | $CH_2F$ | H | S | $OCH_3$ | $CH_3$ | CH | |

TABLE 26

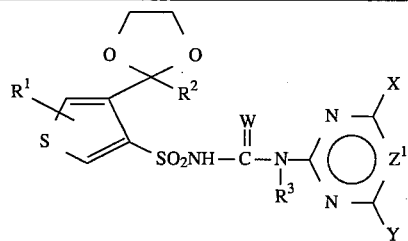

| R¹ | R² | R³ | W | X | Y | Z¹ | mp |
|---|---|---|---|---|---|---|---|
| H | $CH_2F$ | H | S | $OCH_3$ | $OCH_3$ | CH | |
| H | $CH_2F$ | H | S | $CH_3$ | $OCH_3$ | N | |
| H | $CH_2F$ | H | S | $OCH_3$ | $OCH_3$ | N | |
| H | $CH_2Cl$ | H | S | $OCH_3$ | $OCH_3$ | CH | |
| H | $CH_2Br$ | H | S | $OCH_3$ | $OCH_3$ | CH | |
| H | $CHF_2$ | H | S | $OCH_3$ | $OCH_3$ | CH | |
| H | $CHFCl$ | H | S | $OCH_3$ | $OCH_3$ | CH | |
| H | $CHFCH_3$ | H | S | $OCH_3$ | $OCH_3$ | CH | |
| H | $CHClCH_3$ | H | S | $OCH_3$ | $OCH_3$ | CH | |
| 5-$OCH_3$ | $CH_2F$ | H | S | $OCH_3$ | $OCH_3$ | CH | |
| 5-Cl | $CH_2F$ | H | S | $OCH_3$ | $OCH_3$ | CH | |
| H | $CH_2F$ | $CH_3$ | S | $OCH_3$ | $OCH_3$ | CH | |
| H | $CH_2F$ | H | S | $OCH_3$ | $CH_3$ | CH | |

TABLE 27

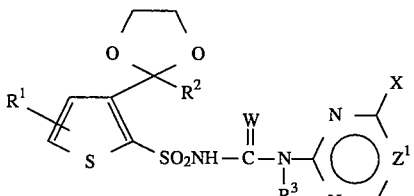

| R¹ | R² | R³ | W | X | Y | Z¹ | mp |
|---|---|---|---|---|---|---|---|
| H | $CH_2F$ | H | S | $OCH_3$ | $OCH_3$ | CH | |
| H | $CH_2F$ | H | S | $CH_3$ | $OCH_3$ | N | |
| H | $CH_2F$ | H | S | $OCH_3$ | $OCH_3$ | N | |
| H | $CH_2Cl$ | H | S | $OCH_3$ | $OCH_3$ | CH | |
| H | $CH_2Br$ | H | S | $OCH_3$ | $OCH_3$ | CH | |
| H | $CHF_2$ | H | S | $OCH_3$ | $OCH_3$ | CH | |
| H | $CHFCl$ | H | S | $OCH_3$ | $OCH_3$ | CH | |
| H | $CHFCH_3$ | H | S | $OCH_3$ | $OCH_3$ | CH | |
| H | $CHClCH_3$ | H | S | $OCH_3$ | $OCH_3$ | CH | |
| 5-$OCH_3$ | $CH_2F$ | H | S | $OCH_3$ | $OCH_3$ | CH | |
| H | $CH_2F$ | $CH_3$ | S | $OCH_3$ | $OCH_3$ | CH | |
| H | $CH_2F$ | H | S | $OCH_3$ | $CH_3$ | CH | |

TABLE 28

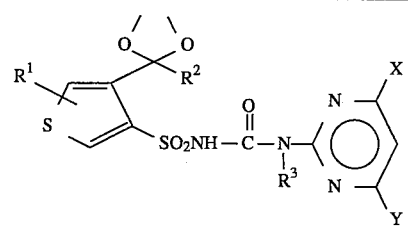

| R¹ | R² | R³ | X | Y | mp (°C.) |
|---|---|---|---|---|---|
| H | $CH_2F$ | H | $OCH_3$ | $OCH_3$ | 115–117 |
| H | $CH_2F$ | H | $CH_3$ | $OCH_3$ | |
| H | $CH_2F$ | H | $CH_3$ | $CH_3$ | 125–130 |

TABLE 28-continued

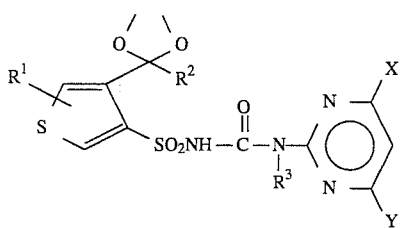

| R¹ | R² | R³ | X | Y | mp (°C.) |
|---|---|---|---|---|---|
| H | CH₂F | H | Cl | OCH₃ | |
| H | CH₂F | H | Br | OCH₃ | |
| H | CH₂F | H | H | CH₃ | |
| H | CH₂F | H | OCH₃ | H | |
| H | CH₂F | H | OCH₃ | CH₂OC₂H₅ | |
| H | CH₂F | H | OCF₂H | OCH₃ | |
| H | CH₂F | H | OCH₃ | CH(OCH₃)₂ | |
| H | CH₂F | H | CH₃ | OC₂H₅ | |
| H | CH₂F | H | CH₃ | CH₂OCH₃ | |
| H | CH₂F | H | OCH₃ | CH₂OCH₃ | |
| H | CH₂F | H | OCH₃ | C₂H₅ | |
| H | CH₂F | H | OC₂H₅ | OCH₃ | |
| H | CH₂F | H | OCH₂CF₃ | OCH₃ | |
| H | CH₂F | H | CF₃ | OCH₃ | |
| H | CH₂F | H | CH₂F | OCH₃ | |
| H | CH₂F | H | CH₂Cl | OCH₃ | |
| H | CH₂F | H | CH₂Br | OCH₃ | |
| H | CH₂F | H | F | OCH₃ | |
| H | CH₂F | H | I | OCH₃ | |
| H | CH₂F | H | OCH₂CH₂F | OCH₃ | |
| H | CH₂F | H | OCH₂CH₂CF₃ | OCH₃ | |
| H | CH₂F | H | OCH₂CHF₂ | CH₃ | |
| H | CH₂F | H | OCH₂CF₃ | CH₃ | |
| H | CH₂F | H | Cl | OC₂H₅ | |
| H | CH₂F | H | OC₂H₅ | NHCH₃ | |
| H | CH₂F | H | OC₂H₅ | CH₂SCH₃ | |
| H | CH₂F | H | OCF₂H | CH₃ | |
| H | CH₂F | H | Cl | OCF₂H | |
| H | CH₂F | H | NH₂ | OC₂H₅ | |
| H | CH₂F | H | n-C₃H₇ | OCH₃ | |
| H | CH₂F | H | NHCH₃ | OCH₃ | |
| H | CH₂F | H | OCH₃ | SCH₃ | |
| H | CH₂F | H | OCH₃ | SCF₂H | |
| H | CH₂F | H | OCH₃ | OCH₂CCH | |
| H | CH₂F | H | OCH₃ | OCH₂CH=CH₂ | |
| H | CH₂F | H | OCH₃ | CCH | |
| H | CH₂F | H | OCH₃ | N(CH₃)₂ | |
| H | CH₂F | H | OCH₃ | cyclopropyl | |
| H | CH₂F | H | OCH₃ | NH₂ | |
| H | CH₂F | H | OCH₃ | CF₃ | |
| H | CH₂F | H | OCH₃ | OCH₃CH₂OCH₃ | |
| H | CH₂F | H | OCH₃ | CH₂SCH₃ | |
| H | CH₂F | H | OCH₃ | CHO | |
| H | CH₂F | H | OCH₃ | COCH₃ | |
| H | CH₂F | H | OCH₃ | CH(SCH₃)OC₂H₅ | |
| H | CH₂F | H | OCH₃ | C(CH₂)(SCH₃)₂ | |
| H | CH₂F | H | OCH₃ | C(SC₂H₅)₂ | |
| H | CH₂F | H | OCH₃ | 1,3-dioxolan-2-yl | |
| H | CH₂F | H | OCH₃ | 2-methyl-1,3-oxathiolan-2yl | |
| H | CH₂F | H | OCH₃ | 1,3-oxathian-2-yl | |
| H | CH₂F | H | OCH₃ | 2-methyl-1,3-dithian-2-yl | |
| H | CH₂F | H | OCH₃ | 4-methyl-1,3-dioxolan-2-yl | |
| H | CH₂F | H | OCH₃ | 2-4-dimethyl-1,3-dithiolan-2-yl | |
| H | CH₂F | H | OCH₃ | N(OCH₃)(CH₃) | |
| H | CH₂F | H | OCH₃ | CCCH₃ | |
| H | CH₂F | H | OCH₃ | C₂H₅ | |
| H | CH₂F | H | OCH₃ | OCF₂Br | |
| H | CHFCH₃ | H | OCH₃ | OC₂H₅ | |
| H | CHFCH₃ | H | CH₃ | OCH₃ | |
| H | CF₃ | H | CH₃ | CH₃ | 196–199 |

TABLE 28-continued

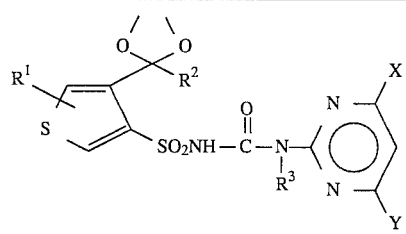

| R¹ | R² | R³ | X | Y | mp (°C.) |
|---|---|---|---|---|---|
| H | CHFCH₃ | H | Cl | OCH₃ | |
| H | CHFCH₃ | H | Br | OCH₃ | |
| H | CHFCH₃ | H | CH₃ | H | |
| H | CHFCH₃ | H | OCH₃ | H | |
| H | CHFCH₃ | H | OCH₃ | CH₂OC₂H₅ | |
| H | CHFCH₃ | H | OCF₂H | OCH₃ | |
| H | CHFCH₃ | H | OCH₃ | CH(OCH₃)₂ | |
| H | CHFCH₃ | H | CH₃ | OC₂H₅ | |
| H | CHFCH₃ | H | CH₃ | CH₂OCH₃ | |
| H | CHFCH₃ | H | OCH₃ | CH₂OCH₃ | |
| H | CHFCH₃ | H | OCH₃ | C₂H₅ | |
| H | CHFCH₃ | H | OC₂H₅ | OCH₃ | |
| H | CHFCH₃ | H | OCH₂CF₃ | OCH₃ | |
| H | CHFCH₃ | H | CF₃ | OCH₃ | |
| H | CHFCH₃ | H | CH₂F | OCH₃ | |
| H | CHFCH₃ | H | CH₂Cl | OCH₃ | |
| H | CHFCH₃ | H | CH₂Br | OCH₃ | |
| H | CHFCH₃ | H | F | OCH₃ | |
| H | CHFCH₃ | H | I | OCH₃ | |
| H | CHFCH₃ | H | OCH₂CH₂F | OCH₃ | |
| H | CHFCH₃ | H | OCH₃CH₂CF₃ | OCH₃ | |
| H | CHFCH₃ | H | OCH₂CHF₂ | CH₃ | |
| H | CHFCH₃ | H | OCH₂CF₃ | CH₃ | |
| H | CHFCH₃ | H | Cl | OC₂H₅ | |
| H | CHFCH₃ | H | OC₂H₅ | NHCH₃ | |
| H | CHFCH₃ | H | OCH₃ | CH₂SCH₃ | |
| H | CHFCH₃ | H | OCF₂H | CH₃ | |
| H | CHFCH₃ | H | Cl | OCF₂H | |
| H | CH₂CH₂F | H | OCH₃ | OCH₃ | |
| H | CH₂CH₂F | H | CH₃ | OCH₃ | |
| H | CH₂CH₂F | H | CH₃ | CH₃ | |
| H | CH₂CH₂F | H | Cl | OCH₃ | |
| H | CH₂CH₂F | H | Br | OCH₃ | |
| H | CH₂CH₂F | H | CH₃ | H | |
| H | CH₂CH₂F | H | OCH₃ | H | |
| H | CH₂CH₂F | H | OCH₃ | CH₂OC₂H₅ | |
| H | CH₂CH₂F | H | OCF₂H | OCH₃ | |
| H | CH₂CH₂F | H | OCH₃ | CH(OCH₃)₂ | |
| H | CH₂CH₂F | H | CH₃ | OC₂H₅ | |
| H | CH₂CH₂F | H | CH₃ | CH₂OCH₃ | |
| H | CH₂CH₂F | H | OCH₃ | CH₂OCH₃ | |
| H | CH₂CH₂F | H | OCH₃ | C₂H₅ | |
| H | CH₂CH₂F | H | OC₂H₅ | OCH₃ | |
| H | CH₂CH₂F | H | OCH₂CF₃ | OCH₃ | |
| H | CH₂CH₂F | H | CF₃ | OCH₃ | |
| H | CH₂CH₂F | H | CH₂F | OCH₃ | |
| H | CH₂CH₂F | H | CH₂Cl | OCH₃ | |
| H | CH₂CH₂F | H | CH₂Br | OCH₃ | |
| H | CH₂CH₂F | H | F | OCH₃ | |
| H | CH₂CH₂F | H | I | OCH₃ | |
| H | CH₂CH₂F | H | OCH₂CH₂F | OCH₃ | |
| H | CH₂CH₂F | H | OCH₃CH₂CF₃ | OCH₃ | |
| H | CH₂CH₂F | H | OCH₂CHF₂ | CH₃ | |
| H | CH₂CH₂F | H | OCH₂CF₃ | CH₃ | |
| H | CF₃ | H | Cl | OC₂H₅ | 165–167 |
| H | CH₂CH₂F | H | OC₂H₅ | NHCH₃ | |
| H | CH₂CH₂F | H | OCH₃ | CH₂SCH₃ | |
| H | CH₂CH₂F | H | OCF₂H | CH₃ | |
| H | CH₂CH₂F | H | Cl | OCF₂H | |
| H | CF₃ | H | OCH₃ | OCH₃ | 180–182 |
| H | CF₃ | H | CH₃ | OCH₃ | 188–191 |
| H | CH₂Cl | H | CH₃ | CH₃ | 166– |

TABLE 28-continued

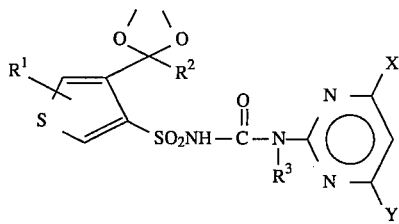

| R¹ | R² | R³ | X | Y | mp (°C.) |
|---|---|---|---|---|---|
| H | CF₃ | H | Cl | OCH₃ | 169 |
| | | | | | 173–174 |
| H | CH₂Cl | H | Br | OCH₃ | |
| H | CH₂Cl | H | CH₃ | H | |
| H | CH₂Cl | H | OCH₃ | H | |
| H | CH₂Cl | H | OCH₃ | CH₂OC₂H₅ | |
| H | CH₂Cl | H | OCF₂H | OCH₃ | |
| H | CH₂Cl | H | OCH₃ | CH(OCH₃)₂ | |
| H | CH₂Cl | H | CH₃ | OC₂H₅ | |
| H | CH₂Cl | H | CH₃ | CH₂OCH₃ | |
| H | CH₂Cl | H | OCH₃ | CH₂OCH₃ | |
| H | CH₂Cl | H | OCH₃ | C₂H₅ | |
| H | CH₂Cl | H | OC₂H₅ | OCH₃ | |
| H | CH₂Cl | H | OCH₂CF₃ | OCH₃ | |
| H | CH₂Cl | H | CF₃ | OCH₃ | |
| H | CH₂Cl | H | CH₂F | OCH₃ | |
| H | CH₂Cl | H | CH₂Cl | OCH₃ | |
| H | CH₂Cl | H | CH₂Br | OCH₃ | |
| H | CH₂Cl | H | F | OCH₃ | |
| H | CH₂Cl | H | I | OCH₃ | |
| H | CH₂Cl | H | OCH₂CH₂F | OCH₃ | |
| H | CH₂Cl | H | OCH₂CH₂CF₃ | OCH₃ | |
| H | CH₂Cl | H | OCH₂CHF₂ | CH₃ | |
| H | CH₂Cl | H | OCH₂CF₃ | CH₃ | |
| H | CH₂Cl | H | Cl | OC₂H₅ | |
| H | CH₂Cl | H | OCH₂H₅ | NHCH₃ | |
| H | CH₂Cl | H | OCH₃ | CH₂SCH₃ | |
| H | CH₂Cl | H | OCF₂H | CH₃ | |
| H | CH₂Cl | H | Cl | OCF₂H | |
| H | CH₂Br | H | OCH₃ | OCH₃ | |
| H | CH₂Br | H | CH₃ | OCH₃ | |
| H | CH₂Br | H | CH₃ | CH₃ | |
| H | CH₂Br | H | Cl | OCH₃ | |
| H | CH₂Br | H | Br | OCH₃ | |
| H | CH₂Br | H | CH₃ | H | |
| H | CH₂Br | H | OCH₃ | H | |
| H | CH₂Br | H | OCH₃ | CH₂OC₂H₅ | |
| H | CH₂Br | H | OCF₂H | OCH₃ | |
| H | CH₂Br | H | OCH₃ | CH(OCH₃)₂ | |
| H | CH₂Br | H | CH₃ | OC₂H₅ | |
| H | CH₂Br | H | CH₃ | CH₂OCH₃ | |
| H | CH₂Br | H | OCH₃ | CH₂OCH₃ | |
| H | CH₂Br | H | OCH₃ | CH₂H₅ | |
| H | CH₂Br | H | OC₂H₅ | OCH₃ | |
| H | CH₂Br | H | OCH₂CF₃ | OCH₃ | |
| H | CH₂Br | H | CF₃ | OCH₃ | |
| H | CH₂Br | H | CH₂F | OCH₃ | |
| H | CH₂Br | H | CH₂Cl | OCH₃ | |
| H | CH₂Br | H | CH₂Br | OCH₃ | |
| H | CH₂Br | H | F | OCH₃ | |
| H | CH₂Br | H | I | OCH₃ | |
| H | CH₂Br | H | OCH₂CH₂F | OCH₃ | |
| H | CH₂Br | H | OCH₂CH₂CF₃ | OCH₃ | |
| H | CH₂Br | H | OCH₂CHF₂ | CH₃ | |
| H | CH₂Br | H | OCH₂CF₃ | CH₃ | |
| H | CH₂Br | H | Cl | OC₂H₅ | |
| H | CH₂Br | H | OC₂H₅ | NHCH₃ | |
| H | CH₂Br | H | OCH₃ | CH₂SCH₃ | |
| H | CH₂Br | H | OCF₂H | CH₃ | |
| H | CH₂Br | H | Cl | OCF₂H | |

TABLE 29

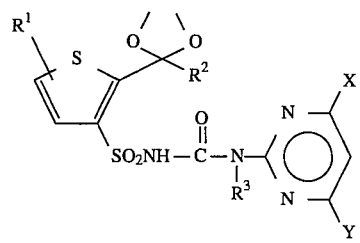

| R¹ | R² | R³ | X | Y | mp (°C.) |
|---|---|---|---|---|---|
| H | CH₂F | H | OCH₃ | OCH₃ | 172–175 |
| H | CH₂F | H | CH₃ | OCH₃ | 186–187 |
| H | CH₂F | H | CH₃ | CH₃ | 190–194 |
| H | CH₂F | H | Cl | OCH₃ | 148–151 |
| H | CH₂F | H | Br | OCH₃ | |
| H | CH₂F | H | Cl | CH₃ | 172–176 |
| H | CH₂F | H | OCH₃ | H | |
| H | CH₂F | H | OCH₃ | CH₂OC₂H₅ | |
| H | CH₂F | H | OCF₂H | OCH₃ | |
| H | CH₂F | H | OCH₃ | CH(OCH₃)₂ | |
| H | CH₂F | H | CH₃ | OC₂H₅ | 160–163 |
| H | CH₂F | H | CH₃ | CH₂OCH₃ | |
| H | CH₂F | H | OCH₃ | CH₂OCH₃ | |
| H | CH₂F | H | C₂H₅ | OCH₃ | |
| H | CH₂F | H | OC₂H₅ | OCH₃ | |
| H | CH₂F | H | OCH₂CF₃ | OCH₃ | |
| H | CH₂F | H | CF₃ | OCH₃ | |
| H | CH₂F | H | CH₂F | OCH₃ | |
| H | CH₂F | H | CH₂Cl | OCH₃ | |
| H | CH₂F | H | CH₂Br | OCH₃ | |
| H | CH₂F | H | F | OCH₃ | |
| H | CH₂F | H | I | OCH₃ | |
| H | CH₂F | H | OCH₂CH₂F | OCH₃ | |
| H | CH₂F | H | OCH₂CH₂CF₃ | OCH₃ | |
| H | CH₂F | H | OCH₃CHF₂ | CH₃ | |
| H | CH₂F | H | OCH₂CF₃ | CH₃ | |
| H | CH₂F | H | Cl | OC₂H₅ | 140–145 |
| H | CH₂F | H | OC₂H₅ | NHCH₃ | |
| H | CH₂F | H | OC₂H₅ | CH₂SCH₃ | |
| H | CH₂F | H | OCF₂H | CH₃ | |
| H | CH₂F | H | Cl | OCF₂H | |
| H | CH₂F | H | NH₂ | OC₂H₅ | |
| H | CH₂F | H | n-C₃H₇ | OCH₃ | |
| H | CH₂F | H | NHCH₃ | OCH₃ | |
| H | CH₂F | H | OCH₃ | SCH₃ | |
| H | CH₂F | H | OCH₃ | SCF₂H | |
| H | CH₂F | H | OCH₃ | OCH₂CCH | |
| H | CH₂F | H | OCH₃ | OCH₂CH=CH₂ | |
| H | CH₂F | H | OCH₃ | CCH | |
| H | CH₂F | H | OCH₃ | N(CH₃)₂ | |
| H | CH₂F | H | OCH₃ | cyclopropyl | |
| H | CH₂F | H | OCH₃ | NH₂ | |
| H | CH₂F | H | OCH₃ | CF₃ | |
| H | CH₂F | H | OCH₃ | OCH₃CH₂OCH₃ | |
| H | CH₂F | H | OCH₃ | CH₂SCH₃ | |
| H | CH₂F | H | OCH₃ | CHO | |
| H | CH₂F | H | OCH₃ | COCH₃ | |
| H | CH₂F | H | OCH₃ | CH(SCH₃)OC₂H₅ | |
| H | CH₂F | H | OCH₃ | C(CH₃)(SCH₃)₂ | |
| H | CH₂F | H | OCH₃ | C(SC₂H₅)₂ | |
| H | CH₂F | H | OCH₃ | 1,3-dioxolan-2-yl | |
| H | CH₂F | H | OCH₃ | 2-methyl-1,3-oxathiolan-2yl | |
| H | CH₂F | H | OCH₃ | 1,3-oxathian-2-yl | |
| H | CH₂F | H | OCH₃ | 2-methyl-1,3-dithian-2-yl | |
| H | CH₂F | H | OCH₃ | 4-methyl-1,3- | |

TABLE 29-continued

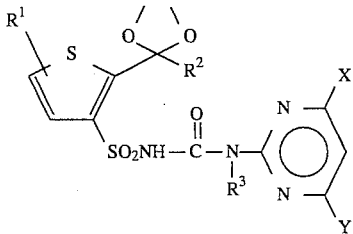

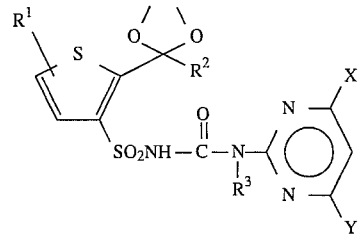

| R¹ | R² | R³ | X | Y | mp (°C.) |
|---|---|---|---|---|---|
| H | $CH_2F$ | H | $OCH_3$ | 2,4-dimethyl-1,3-dioxolan-2-yl dithiolan-2-yl | |
| H | $CH_2F$ | H | $OCH_3$ | $N(OCH_3)(CH_3)$ | |
| H | $CH_2F$ | H | $OCH_3$ | $CCCH_3$ | |
| H | $CH_2F$ | H | $OCH_3$ | $C_2H_5$ | |
| H | $CH_2F$ | H | $OCH_3$ | $OCF_2Br$ | |
| H | $CHFCH_3$ | H | $OCH_3$ | $OC_2H_5$ | |
| H | $CHFCH_3$ | H | $CH_3$ | $OCH_3$ | |
| H | $CHFCH_3$ | H | $CH_3$ | $CH_3$ | |
| H | $CHFCH_3$ | H | Cl | $OCH_3$ | |
| H | $CHFCH_3$ | H | Br | $OCH_3$ | |
| H | $CHFCH_3$ | H | $CH_3$ | H | |
| H | $CHFCH_3$ | H | $OCH_3$ | H | |
| H | $CHFCH_3$ | H | $OCH_3$ | $CH_2OC_2H_5$ | |
| H | $CHFCH_3$ | H | $OCF_2H$ | $OCH_3$ | |
| H | $CHFCH_3$ | H | $OCH_3$ | $CH(OCH_3)_2$ | |
| H | $CHFCH_3$ | H | $CH_3$ | $OC_2H_5$ | |
| H | $CHFCH_3$ | H | $CH_3$ | $CH_2OCH_3$ | |
| H | $CHFCH_3$ | H | $OCH_3$ | $CH_2OCH_3$ | |
| H | $CHFCH_3$ | H | $OCH_3$ | $C_2H_5$ | |
| H | $CHFCH_3$ | H | $OC_2H_5$ | $OCH_3$ | |
| H | $CHFCH_3$ | H | $OCH_2CF_3$ | $OCH_3$ | |
| H | $CHFCH_3$ | H | $CF_3$ | $OCH_3$ | |
| H | $CHFCH_3$ | H | $CH_2F$ | $OCH_3$ | |
| H | $CHFCH_3$ | H | $CH_2Cl$ | $OCH_3$ | |
| H | $CHFCH_3$ | H | $CH_2Br$ | $OCH_3$ | |
| H | $CHFCH_3$ | H | F | $OCH_3$ | |
| H | $CHFCH_3$ | H | I | $OCH_3$ | |
| H | $CHFCH_3$ | H | $OCH_2CH_2F$ | $OCH_3$ | |
| H | $CHFCH_3$ | H | $OCH_2CH_2CF_3$ | $OCH_3$ | |
| H | $CHFCH_3$ | H | $OCH_2CHF_2$ | $CH_3$ | |
| H | $CHFCH_3$ | H | $OCH_2CF_3$ | $CH_3$ | |
| H | $CHFCH_3$ | H | Cl | $OC_2H_5$ | |
| H | $CHFCH_3$ | H | $OC_2H_5$ | $NHCH_3$ | |
| H | $CHFCH_3$ | H | $OCH_3$ | $CH_2SCH_3$ | |
| H | $CHFCH_3$ | H | $OCF_2H$ | $CH_3$ | |
| H | $CHFCH_3$ | H | Cl | $OCF_2H$ | |
| H | $CH_2CH_2F$ | H | $OCH_3$ | $OCH_3$ | |
| H | $CH_2CH_2F$ | H | $CH_3$ | $OCH_3$ | |
| H | $CH_2CH_2F$ | H | $CH_3$ | $CH_3$ | |
| H | $CH_2CH_2F$ | H | Cl | $OCH_3$ | |
| H | $CH_2CH_2F$ | H | Br | $OCH_3$ | |
| H | $CH_2CH_2F$ | H | $CH_3$ | Cl | |
| H | $CH_2CH_2F$ | H | $OCH_3$ | H | |
| H | $CH_2CH_2F$ | H | $OCH_3$ | $CH_2OC_2H_5$ | |
| H | $CH_2CH_2F$ | H | $OCF_2H$ | $OCH_3$ | |
| H | $CH_2CH_2F$ | H | $OCH_3$ | $CH(OCH_3)_2$ | |
| H | $CH_2CH_2F$ | H | $CH_3$ | $OC_2H_5$ | |
| H | $CH_2CH_2F$ | H | $CH_3$ | $CH_2OCH_3$ | |
| H | $CH_2CH_2F$ | H | $OCH_3$ | $CH_2OCH_3$ | |
| H | $CH_2CH_2F$ | H | $OCH_3$ | $C_2H_5$ | |
| H | $CH_2CH_2F$ | H | $OC_2H_5$ | $OCH_3$ | |
| H | $CH_2CH_2F$ | H | $OCH_2CF_3$ | $OCH_3$ | |
| H | $CH_2CH_2F$ | H | $CF_3$ | $OCH_3$ | |
| H | $CH_2CH_2F$ | H | $CH_2F$ | $OCH_3$ | |
| H | $CH_2CH_2F$ | H | $CH_2Cl$ | $OCH_3$ | |
| H | $CH_2CH_2F$ | H | $CH_2Br$ | $OCH_3$ | |
| H | $CH_2CH_2F$ | H | F | $OCH_3$ | |
| H | $CH_2CH_2F$ | H | I | $OCH_3$ | |
| H | $CH_2CH_2F$ | H | $OCH_2CH_2F$ | $OCH_3$ | |
| H | $CH_2CH_2F$ | H | $OCH_2CH_2CF_3$ | $OCH_3$ | |
| H | $CH_2CH_2F$ | H | $OCH_2CHF_2$ | $CH_3$ | |
| H | $CH_2CH_2F$ | H | $OCH_2CF_3$ | $CH_3$ | |
| H | $CH_2CH_2F$ | H | Cl | $OC_2H_5$ | |
| H | $CH_2CH_2F$ | H | $OCH_2H_5$ | $NHCH_3$ | |
| H | $CH_2CH_2F$ | H | $OCH_3$ | $CH_2SCH_3$ | |
| H | $CH_2CH_2F$ | H | $OCF_2H$ | $CH_3$ | |
| H | $CH_2CH_2F$ | H | Cl | $OCF_2H$ | |
| H | $CH_2Cl$ | H | $OCH_3$ | $OCH_3$ | |
| H | $CH_2Cl$ | H | $CH_3$ | $OCH_3$ | 157–160 |
| H | $CH_2Cl$ | H | Cl | $OCH_3$ | 156–159 |
| H | $CH_2Cl$ | H | Br | $OCH_3$ | |
| H | $CH_2Cl$ | H | $CH_3$ | Cl | 149–153 |
| H | $CH_2Cl$ | H | $OCH_3$ | H | |
| H | $CH_2Cl$ | H | $OCH_3$ | $CH_2OC_2H_5$ | |
| H | $CH_2Cl$ | H | $OCF_2H$ | $OCH_3$ | |
| H | $CH_2Cl$ | H | $OCH_3$ | $CH(OCH_3)_2$ | |
| H | $CH_2Cl$ | H | $CH_3$ | $OC_2H_5$ | 178–180 |
| H | $CH_2Cl$ | H | $CH_3$ | $CH_2OCH_3$ | |
| H | $CH_2Cl$ | H | $OCH_3$ | $CH_2OCH_3$ | |
| H | $CH_2Cl$ | H | $OCH_3$ | $C_2H_5$ | |
| H | $CH_2Cl$ | H | $OC_2H_5$ | $OCH_3$ | |
| H | $CH_2Cl$ | H | $OCH_2CF_3$ | $OCH_3$ | |
| H | $CH_2Cl$ | H | $CF_3$ | $OCH_3$ | |
| H | $CH_2Cl$ | H | $CH_2F$ | $OCH_3$ | |
| H | $CH_2Cl$ | H | $CH_2Cl$ | $OCH_3$ | |
| H | $CH_2Cl$ | H | $CH_2Br$ | $OCH_3$ | |
| H | $CH_2Cl$ | H | F | $OCH_3$ | |
| H | $CH_2Cl$ | H | I | $OCH_3$ | |
| H | $CH_2Cl$ | H | $OCH_2CH_2F$ | $OCH_3$ | |
| H | $CH_2Cl$ | H | $OCH_2CH_2CF_3$ | $OCH_3$ | |
| H | $CH_2Cl$ | H | $OCH_2CHF_2$ | $CH_3$ | |
| H | $CH_2Cl$ | H | $OCH_2CF_3$ | $CH_3$ | |
| H | $CH_2Cl$ | H | Cl | $OC_2H_5$ | 147–149 |
| H | $CH_2Cl$ | H | $OC_2H_5$ | $NHCH_3$ | |
| H | $CH_2Cl$ | H | $OCH_3$ | $CH_2SCH_3$ | |
| H | $CH_2Cl$ | H | $OCF_2H$ | $CH_3$ | |
| H | $CH_2Cl$ | H | Cl | $OCF_2H$ | |
| H | $CH_2Br$ | H | $OCH_3$ | $OCH_3$ | |
| H | $CH_2Br$ | H | $CH_3$ | $OCH_3$ | |
| H | $CH_2Br$ | H | $CH_3$ | $CH_3$ | |
| H | $CH_2Br$ | H | Cl | $OCH_3$ | |
| H | $CH_2Br$ | H | Br | $OCH_3$ | |
| H | $CH_2Br$ | H | $CH_3$ | H | |
| H | $CH_2Br$ | H | $OCH_3$ | H | |
| H | $CH_2Br$ | H | $OCH_3$ | $CH_2OC_2H_5$ | |
| H | $CH_2Br$ | H | $OCF_2H$ | $OCH_3$ | |
| H | $CH_2Br$ | H | $OCH_3$ | $CH(OCH_3)_2$ | |
| H | $CH_2Br$ | H | $CH_3$ | $OC_2H_5$ | |
| H | $CH_2Br$ | H | $CH_3$ | $CH_2OCH_3$ | |
| H | $CH_2Br$ | H | $OCH_3$ | $CH_2OCH_3$ | |
| H | $CH_2Br$ | H | $OCH_3$ | $C_2H_5$ | |
| H | $CH_2Br$ | H | $OC_2H_5$ | $OCH_3$ | |
| H | $CH_2Br$ | H | $OCH_2CF_3$ | $OCH_3$ | |
| H | $CH_2Br$ | H | $CF_3$ | $OCH_3$ | |
| H | $CH_2Br$ | H | $CH_2F$ | $OCH_3$ | |
| H | $CH_2Br$ | H | $CH_2Cl$ | $OCH_3$ | |
| H | $CH_2Br$ | H | $CH_2Br$ | $OCH_3$ | |
| H | $CH_2Br$ | H | F | $OCH_3$ | |
| H | $CH_2Br$ | H | I | $OCH_3$ | |
| H | $CH_2Br$ | H | $OCH_2CH_2F$ | $OCH_3$ | |
| H | $CH_2Br$ | H | $OCH_2CH_2CF_3$ | $OCH_3$ | |

TABLE 29-continued

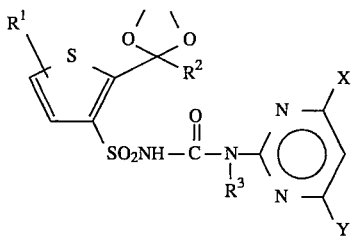

| R¹ | R² | R³ | X | Y | mp (°C.) |
|----|----|----|----|----|----|
| H | CH₂Br | H | OCH₂CHF₂ | CH₃ | |
| H | CH₂Br | H | OCH₂CF₃ | CH₃ | |
| H | CH₂Br | H | Cl | OC₂H₅ | |
| H | CH₂Br | H | OC₂H₅ | NHCH₃ | |
| H | CH₂Br | H | OCH₃ | CH₂SCH₃ | |
| H | CH₂Br | H | OCF₂H | CH₃ | |
| H | CH₂Br | H | Cl | OCF₂H | |

TABLE 30

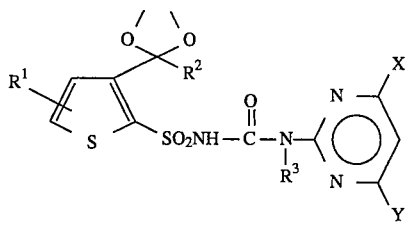

| R¹ | R² | R³ | X | Y | mp (°C.) |
|----|----|----|----|----|----|
| H | CH₂F | H | CH₃ | OCH₃ | 172–177 |
| H | CH₂F | H | OCH₃ | OCH₃ | 183–187 |
| H | CH₂F | H | OC₂H₅ | NHCH₃ | |
| H | CH₂F | H | OCH₃ | N(OCH₃)(CH₃) | |
| H | CH₂F | H | OCH₃ | N(CH₃)₂ | |
| H | CH₂Cl | H | CH₃ | OCH₃ | |
| H | CH₂Cl | H | OCH₃ | OCH₃ | |
| H | CH₂Cl | H | OC₂H₅ | NHCH₃ | |
| H | CH₂Cl | H | OCH₃ | N(OCH₃)(CH₃) | |
| H | CH₂Cl | H | OCH₃ | N(CH₃)₂ | |
| H | CH₂Br | H | CH₃ | OCH₃ | |
| H | CH₂Br | H | OCH₃ | OCH₃ | |
| H | CH₂Br | H | OC₂H₅ | NHCH₃ | |
| H | CH₂Br | H | OCH₃ | N(OCH₃)(CH₃) | |
| H | CH₂Br | H | OCH₃ | N(CH₃)₂ | |
| H | CHF₂ | H | CH₃ | OCH₃ | |
| H | CHF₂ | H | OCH₃ | OCH₃ | |
| H | CHF₂ | H | OC₂H₅ | NHCH₃ | |
| H | CHF₂ | H | OCH₃ | N(OCH₃)(CH₃) | |
| H | CHF₂ | H | OCH₃ | N(CH₃)₂ | |
| H | CH₂F | CH₃ | OCH₃ | OCH₃ | |
| H | CH₂Cl | CH₃ | OCH₃ | OCH₃ | |
| H | CH₂F | CH₃ | CH₃ | OCH₃ | |
| H | CH₂Br | CH₃ | OCH₃ | OCH₃ | |
| H | CH₂Cl | CH₃ | CH₃ | OCH₃ | |
| H | CH₂Br | CH₃ | CH₃ | OCH₃ | |
| H | CHF₂ | CH₃ | OCH₃ | OCH₃ | |
| H | CHF₂ | CH₃ | CH₃ | OCH₃ | |
| H | CH₂F | CH₃ | OC₂H₅ | NHCH₃ | |
| H | CH₂F | CH₃ | OCH₃ | N(CH₃)₂ | |
| H | CHFCH₃ | H | CH₃ | OCH₃ | |
| H | CHFCH₃ | H | OCH₃ | OCH₃ | |
| H | CHFCH₃ | H | OC₂H₅ | NHCH₃ | |
| H | CHFCH₃ | H | OCH₃ | N(OCH₃)(CH₃) | |
| H | CHFCH₃ | H | OCH₃ | N(CH₃)₂ | |
| H | CHClCH₃ | H | CH₃ | OCH₃ | |
| H | CHClCH₃ | H | OCH₃ | OCH₃ | |
| H | CHClCH₃ | H | OC₂H₅ | NHCH₃ | |
| H | CHClCH₃ | H | OCH₃ | N(OCH₃)(CH₃) | |

TABLE 30-continued

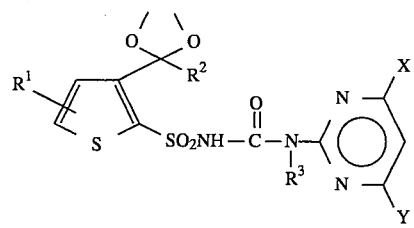

| R¹ | R² | R³ | X | Y | mp (°C.) |
|----|----|----|----|----|----|
| H | CHClCH₃ | H | OCH₃ | N(CH₃)₂ | |
| H | CH₂CH₂F | H | CH₃ | OCH₃ | |
| H | CH₂CH₂F | H | OCH₃ | OCH₃ | |
| H | CH₂CH₂F | H | OC₂H₅ | NHCH₃ | |
| H | CH₂CH₂F | H | OCH₃ | N(OCH₃)(CH₃) | |
| H | CH₂CH₂F | H | OCH₃ | N(CH₃)₂ | |
| H | CHFCl | H | OCH₃ | OCH₃ | |
| H | CHFCl | H | CH₃ | OCH₃ | |
| H | CHFCl | H | CH₃ | CH₃ | |
| H | CHFCl | H | Cl | OCH₃ | |
| H | CHFCl | H | OCH₃ | CH₂OCH₃ | |
| H | CHFCl | H | CH₃ | OC₂H₅ | |
| H | CHFCl | H | CH₂Cl | OCH₃ | |
| H | CHFCl | H | F | OCH₃ | |
| H | CHFCl | H | OCH₃ | CH(OCH₃)₂ | |
| H | CHFCl | H | OCHF₂ | OCH₃ | |
| H | CHFCl | H | C₂H₅ | OCH₃ | |
| 5-F | CH₂F | H | CH₃ | OCH₃ | |

TABLE 31

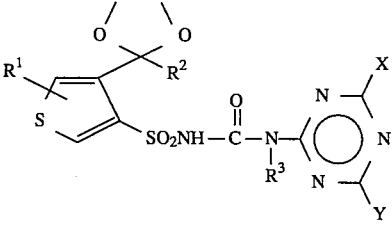

| R¹ | R² | R³ | X | Y | mp (°C.) |
|----|----|----|----|----|----|
| H | CH₂F | H | CH₃ | OCH₃ | 129–133 |
| H | CH₂F | H | OCH₃ | OCH₃ | 139–142 |
| H | CH₂F | H | OC₂H₅ | NHCH₃ | |
| H | CH₂F | H | OCH₃ | N(OCH₃)(CH₃) | |
| H | CH₂F | H | OCH₃ | N(CH₃)₂ | |
| H | CH₂Cl | H | CH₃ | OCH₃ | 138–141 |
| H | CH₂Cl | H | OCH₃ | OCH₃ | 133–136 |
| H | CH₂Cl | H | OC₂H₅ | NHCH₃ | |
| H | CH₂Cl | H | OCH₃ | N(OCH₃)(CH₃) | |
| H | CH₂Cl | H | OCH₃ | N(CH₃)₂ | |
| H | CH₂Br | H | CH₃ | OCH₃ | |
| H | CH₂Br | H | OCH₃ | OCH₃ | |
| H | CH₂Br | H | OC₂H₅ | NHCH₃ | |
| H | CH₂Br | H | OCH₃ | N(OCH₃)(CH₃) | |
| H | CH₂Br | H | OCH₃ | N(CH₃)₂ | |
| H | CHF₂ | H | CH₃ | OCH₃ | |
| H | CHF₂ | H | OCH₃ | OCH₃ | |
| H | CHF₂ | H | OC₂H₅ | NHCH₃ | |
| H | CHF₂ | H | OCH₃ | N(OCH₃)(CH₃) | |
| H | CHF₂ | H | OCH₃ | N(CH₃)₂ | |
| H | CH₂F | CH₃ | OCH₃ | OCH₃ | |
| H | CH₂Cl | CH₃ | OCH₃ | OCH₃ | |
| H | CH₂F | CH₃ | CH₃ | OCH₃ | |
| H | CH₂Br | CH₃ | OCH₃ | OCH₃ | |
| H | CH₂Cl | CH₃ | CH₃ | OCH₃ | |
| H | CH₂Br | CH₃ | CH₃ | OCH₃ | |
| H | CHF₂ | CH₃ | OCH₃ | OCH₃ | |
| H | CHF₂ | CH₃ | CH₃ | OCH₃ | |
| H | CH₂F | CH₃ | OC₂H₅ | NHCH₃ | |
| H | CH₂F | CH₃ | OCH₃ | N(CH₃)₂ | |

TABLE 31-continued

| R¹ | R² | R³ | X | Y | mp (°C.) |
|---|---|---|---|---|---|
| H | CHFCH₃ | H | CH₃ | OCH₃ | |
| H | CHFCH₃ | H | OCH₃ | OCH₃ | |
| H | CHFCH₃ | H | OC₂H₅ | NHCH₃ | |
| H | CHFCH₃ | H | OCH₃ | N(OCH₃)(CH₃) | |
| H | CHFCH₃ | H | OCH₃ | N(CH₃)₂ | |
| H | CHClCH₃ | H | CH₃ | OCH₃ | |
| H | CHClCH₃ | H | OCH₃ | OCH₃ | |
| H | CHClCH₃ | H | OC₂H₅ | NHCH₃ | |
| H | CHClCH₃ | H | OCH₃ | N(OCH₃)(CH₃) | |
| H | CHClCH₃ | H | OCH₃ | N(CH₃)₂ | |
| H | CH₂CH₂F | H | CH₃ | OCH₃ | |
| H | CH₂CH₂F | H | OCH₃ | OCH₃ | |
| H | CH₂CH₂F | H | OC₂H₅ | NHCH₃ | |
| H | CH₂CH₂F | H | OCH₃ | N(OCH₃)(CH₃) | |
| H | CH₂CH₂F | H | OCH₃ | N(CH₃)₂ | |
| H | CHF₃ | H | OCH₃ | OCH₃ | 165–166 |
| H | CHF₃ | H | OCH₃ | OCH₃ | 174–176 |
| H | CHF₃ | H | CH₃ | OCH₃ | |
| H | CHFCl | H | Cl | OCH₃ | |
| H | CHFCl | H | OCH₃ | CH₂OCH₃ | |
| H | CHFCl | H | CH₃ | OC₂H₅ | |
| H | CHFCl | H | CH₂Cl | OCH₃ | |
| H | CHFCl | H | F | OCH₃ | |
| H | CHFCl | H | OCH₃ | CH(OCH₃)₂ | |
| H | CHFCl | H | OCHF₂ | OCH₃ | |
| H | CHFCl | H | C₂H₅ | OCH₃ | |
| 5-F | CH₂F | H | CH₃ | OCH₃ | |

TABLE 32

| R¹ | R² | R³ | X | Y | mp (°C.) |
|---|---|---|---|---|---|
| H | CH₂F | H | CH₃ | OCH₃ | 153–157 |
| H | CH₂F | H | OCH₃ | OCH₃ | 135–139 |
| H | CH₂F | H | OC₂H₅ | NHCH₃ | |
| H | CH₂F | H | OCH₃ | N(OCH₃)(CH₃) | |
| H | CH₂F | H | OCH₃ | N(CH₃)₂ | |
| H | CH₂Cl | H | CH₃ | OCH₃ | 138–140 |
| H | CH₂Cl | H | OCH₃ | OCH₃ | 127–129 |
| H | CH₂Cl | H | OC₂H₅ | NHCH₃ | |
| H | CH₂Cl | H | OCH₃ | N(OCH₃)(CH₃) | |
| H | CH₂Cl | H | OCH₃ | N(CH₃)₂ | |
| H | CH₂Br | H | CH₃ | OCH₃ | |
| H | CH₂Br | H | OCH₃ | OCH₃ | |
| H | CH₂Br | H | OC₂H₅ | NHCH₃ | |
| H | CH₂Br | H | OCH₃ | N(OCH₃)(CH₃) | |
| H | CH₂Br | H | OCH₃ | N(CH₃)₂ | |
| H | CHF₂ | H | CH₃ | OCH₃ | |
| H | CHF₂ | H | OCH₃ | OCH₃ | |
| H | CHF₂ | H | OC₂H₅ | NHCH₃ | |
| H | CHF₂ | H | OCH₃ | N(OCH₃)(CH₃) | |
| H | CHF₂ | H | OCH₃ | N(CH₃)₂ | |

TABLE 32-continued

| R¹ | R² | R³ | X | Y | mp (°C.) |
|---|---|---|---|---|---|
| H | CH₂F | CH₃ | OCH₃ | OCH₃ | |
| H | CH₂Cl | CH₃ | OCH₃ | OCH₃ | |
| H | CH₂F | CH₃ | CH₃ | OCH₃ | |
| H | CH₂Br | CH₃ | OCH₃ | OCH₃ | |
| H | CH₂Br | CH₃ | CH₃ | OCH₃ | |
| H | CHF₂ | CH₃ | OCH₃ | OCH₃ | |
| H | CHF₂ | CH₃ | CH₃ | OCH₃ | |
| H | CH₂F | CH₃ | OC₂H₅ | NHCH₃ | |
| H | CH₂F | CH₃ | OCH₃ | N(CH₃)₂ | |
| H | CHFCH₃ | H | CH₃ | OCH₃ | |
| H | CHFCH₃ | H | OCH₃ | OCH₃ | |
| H | CHFCH₃ | H | OC₂H₅ | NHCH₃ | |
| H | CHFCH₃ | H | OCH₃ | N(OCH₃)(CH₃) | |
| H | CHFCH₃ | H | OCH₃ | N(CH₃)₂ | |
| H | CHClCH₃ | H | CH₃ | OCH₃ | |
| H | CHClCH₃ | H | OCH₃ | OCH₃ | |
| H | CHClCH₃ | H | OC₂H₅ | NHCH₃ | |
| H | CHClCH₃ | H | OCH₃ | N(OCH₃)(CH₃) | |
| H | CHClCH₃ | H | OCH₃ | N(CH₃)₂ | |
| H | CH₂CH₂F | H | CH₃ | OCH₃ | |
| H | CH₂CH₂F | H | OCH₃ | OCH₃ | |
| H | CH₂CH₂F | H | OC₂H₅ | NHCH₃ | |
| H | CH₂CH₂F | H | OCH₃ | N(OCH₃)(CH₃) | |
| H | CH₂CH₂F | H | OCH₃ | N(CH₃)₂ | |
| H | CHFCl | H | OCH₃ | OCH₃ | |
| H | CHFCl | H | CH₃ | OCH₃ | |
| H | CHFCl | H | CH₃ | CH₃ | |
| H | CHFCl | H | Cl | OCH₃ | |
| H | CHFCl | H | OCH₃ | CH₂OCH₃ | |
| H | CHFCl | H | CH₃ | OC₂H₅ | |
| H | CHFCl | H | CH₂Cl | OCH₃ | |
| H | CHFCl | H | F | OCH₃ | |
| H | CHFCl | H | OCH₃ | CH(OCH₃)₂ | |
| H | CHFCl | H | OCHF₂ | OCH₃ | |
| H | CHFCl | H | C₂H₅ | OCH₃ | |
| 5-F | CH₂F | H | CH₃ | OCH₃ | |

TABLE 33

| R¹ | R² | R³ | X | Y | mp (°C.) |
|---|---|---|---|---|---|
| H | CH₂F | H | CH₃ | OCH₃ | 168–171 |
| H | CH₂F | H | OCH₃ | OCH₃ | 145–148 |
| H | CH₂F | H | OC₂H₅ | NHCH₃ | |
| H | CH₂F | H | OCH₃ | N(OCH₃)(CH₃) | |
| H | CH₂F | H | OCH₃ | N(CH₃)₂ | |
| H | CH₂Cl | H | CH₃ | OCH₃ | |
| H | CH₂Cl | H | OCH₃ | OCH₃ | |
| H | CH₂Cl | H | OC₂H₅ | NHCH₃ | |
| H | CH₂Cl | H | OCH₃ | N(OCH₃)(CH₃) | |
| H | CH₂Cl | H | OCH₃ | N(CH₃)₂ | |

TABLE 33-continued

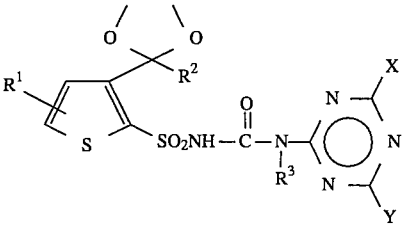

| R¹ | R² | R³ | X | Y | mp (°C.) |
|---|---|---|---|---|---|
| H | CH₂Br | H | CH₃ | OCH₃ | |
| H | CH₂Br | H | OCH₃ | OCH₃ | |
| H | CH₂Br | H | OC₂H₅ | NHCH₃ | |
| H | CH₂Br | H | OCH₃ | N(OCH₃)(CH₃) | |
| H | CH₂Br | H | OCH₃ | N(CH₃)₂ | |
| H | CHF₂ | H | CH₃ | OCH₃ | |
| H | CHF₂ | H | OCH₃ | OCH₃ | |
| H | CHF₂ | H | OC₂H₅ | NHCH₃ | |
| H | CHF₂ | H | OCH₃ | N(OCH₃)(CH₃) | |
| H | CHF₂ | H | OCH₃ | N(CH₃)₂ | |
| H | CH₂F | CH₃ | OCH₃ | OCH₃ | |
| H | CH₂Cl | CH₃ | OCH₃ | OCH₃ | |
| H | CH₂F | CH₃ | CH₃ | OCH₃ | |
| H | CH₂Br | CH₃ | OCH₃ | OCH₃ | |
| H | CH₂Cl | CH₃ | CH₃ | OCH₃ | |
| H | CH₂Br | CH₃ | CH₃ | OCH₃ | |
| H | CHF₂ | CH₃ | OCH₃ | OCH₃ | |
| H | CHF₂ | CH₃ | CH₃ | OCH₃ | |
| H | CH₂F | CH₃ | OC₂H₅ | NHCH₃ | |
| H | CH₂F | CH₃ | OCH₃ | N(CH₃)₂ | |
| H | CHFCH₃ | H | CH₃ | OCH₃ | |
| H | CHFCH₃ | H | OCH₃ | OCH₃ | |
| H | CHFCH₃ | H | OC₂H₅ | NHCH₃ | |
| H | CHFCH₃ | H | OCH₃ | N(OCH₃)(CH₃) | |

TABLE 33-continued

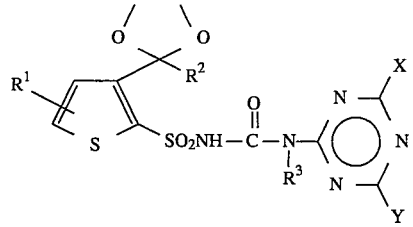

| R¹ | R² | R³ | X | Y | mp (°C.) |
|---|---|---|---|---|---|
| H | CHFCH₃ | H | OCH₃ | N(CH₃)₂ | |
| H | CHClCH₃ | H | CH₃ | OCH₃ | |
| H | CHClCH₃ | H | OCH₃ | OCH₃ | |
| H | CHClCH₃ | H | OC₂H₅ | NHCH₃ | |
| H | CHClCH₃ | H | OCH₃ | N(OCH₃)(CH₃) | |
| H | CHClCH₃ | H | OCH₃ | N(CH₃)₂ | |
| H | CH₂CH₂F | H | CH₃ | OCH₃ | |
| H | CH₂CH₂F | H | OCH₃ | OCH₃ | |
| H | CH₂CH₂F | H | OC₂H₅ | NHCH₃ | |
| H | CH₂CH₂F | H | OCH₃ | N(OCH₃)(CH₃) | |
| H | CH₂CH₂F | H | OCH₃ | N(CH₃)₂ | |
| H | CHFCl | H | OCH₃ | OCH₃ | |
| H | CHFCl | H | CH₃ | OCH₃ | |
| H | CHFCl | H | CH₃ | CH₃ | |
| H | CHFCl | H | Cl | OCH₃ | |
| H | CHFCl | H | OCH₃ | CH₂OCH₃ | |
| H | CHFCl | H | CH₃ | OC₂H₅ | |
| H | CHFCl | H | CH₂Cl | OCH₃ | |
| H | CHFCl | H | F | OCH₃ | |
| H | CHFCl | H | OCH₃ | CH(OCH₃)₂ | |
| H | CHFCl | H | OCHF₂ | OCH₃ | |
| H | CHFCl | H | C₂H₅ | OCH₃ | |
| 5-F | CH₂F | H | CH₃ | OCH₃ | |

TABLE 34

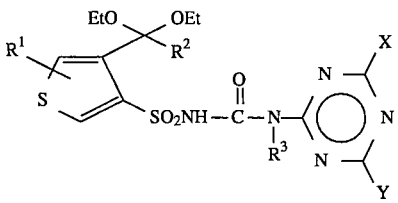

| R¹ | R² | R³ | X | Y | mp (°C.) |
|---|---|---|---|---|---|
| H | CH₂F | H | OCH₃ | OCH₃ | 146–148 |
| H | CH₂F | H | CH₃ | OCH₃ | 145–148 |
| H | CH₂F | H | CH₃ | CH₃ | 177–178 |
| H | CH₂F | H | Cl | OCH₃ | 149–150 |
| H | CH₂F | H | Br | OCH₃ | |
| H | CH₂F | H | H | CH₃ | |
| H | CH₂F | H | OCH₃ | H | |
| H | CH₂F | H | OCH₃ | CH₂OC₂H₅ | |
| H | CH₂F | H | OCF₂H | OCH₃ | |
| H | CH₂F | H | OCH₃ | CH(OCH₃)₂ | |
| H | CH₂F | H | CH₃ | OC₂H₅ | |
| H | CH₂F | H | CH₃ | CH₂OCH₃ | |
| H | CH₂F | H | OCH₃ | CH₂OCH₃ | |
| H | CH₂F | H | C₂H₅ | OCH₃ | |
| H | CH₂F | H | OC₂H₅ | OCH₃ | |
| H | CH₂F | H | OCH₂CF₃ | OCH₃ | |
| H | CH₂F | H | CF₃ | OCH₃ | |
| H | CH₂F | H | CH₂F | OCH₃ | |
| H | CH₂F | H | CH₂Cl | OCH₃ | |
| H | CH₂F | H | CH₂Br | OCH₃ | |
| H | CH₂F | H | F | OCH₃ | |
| H | CH₂F | H | I | OCH₃ | |
| H | CH₂F | H | OCH₂CH₂F | OCH₃ | |
| H | CH₂F | H | OCH₂CH₂CF₃ | OCH₃ | |

TABLE 34-continued

| R¹ | R² | R³ | X | Y | mp (°C.) |
|---|---|---|---|---|---|
| H | CH₂F | H | OCH₂CHF₂ | CH₃ | |
| H | CH₂F | H | OCH₂CF₃ | CH₃ | |
| H | CH₂F | H | Cl | OC₂H₅ | |
| H | CH₂F | H | OC₂H₅ | NHCH₃ | |
| H | CH₂F | H | OC₂H₅ | CH₂SCH₃ | |
| H | CH₂F | H | OCF₂H | CH₃ | |
| H | CH₂F | H | Cl | OCF₂H | |
| H | CH₂F | H | NH₂ | OC₂H₅ | |
| H | CH₂F | H | n-C₃H₇ | OCH₃ | |
| H | CH₂F | H | NHCH₃ | OCH₃ | |
| H | CH₂F | H | OCH₃ | SCH₃ | |
| H | CH₂F | H | OCH₃ | SCF₂H | |
| H | CH₂F | H | OCH₃ | OCH₂CCH | |
| H | CH₂F | H | OCH₃ | OCH₂CH=CH₂ | |
| H | CH₂F | H | OCH₃ | CCH | |
| H | CH₂F | H | OCH₃ | N(CH₃)₂ | |
| H | CH₂F | H | OCH₃ | cyclopropyl | |
| H | CH₂F | H | OCH₃ | NH₂ | |
| H | CH₂F | H | OCH₃ | CF₃ | |
| H | CH₂F | H | OCH₃ | OCH₂CH₂OCH₃ | |
| H | CH₂F | H | OCH₃ | CH₂SCH₃ | |
| H | CH₂F | H | OCH₃ | CHO | |
| H | CH₂F | H | OCH₃ | COCH₃ | |
| H | CH₂F | H | OCH₃ | CH(SCH₃)OC₂H₅ | |
| H | CH₂F | H | OCH₃ | C(CH₃)(SCH₃)₂ | |
| H | CH₂F | H | OCH₃ | C(SC₂H₅)₂ | |
| H | CH₂F | H | OCH₃ | 1,3-dioxolan-2-yl | |
| H | CH₂F | H | OCH₃ | 2-methyl-1,3-oxathiolan-2yl | |
| H | CH₂F | H | OCH₃ | 1,3-oxathian-2-yl | |
| H | CH₂F | H | OCH₃ | 2-methyl-1,3-dithian-2-yl | |
| H | CH₂F | H | OCH₃ | 4-methyl-1,3-dioxolan-2-yl | |
| H | CH₂F | H | OCH₃ | 2-4-dimethyl-1,3-dithiolan-2-yl | |
| H | CH₂F | H | OCH₃ | N(OCH₃)(CH₃) | |
| H | CH₂F | H | OCH₃ | CCCH₃ | |
| H | CH₂F | H | OCH₃ | C₂H₅ | |
| H | CH₂F | H | OCH₃ | OCF₂Br | |
| H | CHFCH₃ | H | OCH₃ | OC₂H₅ | |
| H | CHFCH₃ | H | CH₃ | OCH₃ | |
| H | CHFCH₃ | H | CH₃ | CH₃ | |
| H | CHFCH₃ | H | Cl | OCH₃ | |
| H | CHFCH₃ | H | Br | OCH₃ | |
| H | CHFCH₃ | H | CH₃ | H | |
| H | CHFCH₃ | H | OCH₃ | H | |
| H | CHFCH₃ | H | OCH₃ | CH₂OC₂H₅ | |
| H | CHFCH₃ | H | OCO₂H | OCH₃ | |
| H | CHFCH₃ | H | OCH₃ | CH(OCH₃)₂ | |
| H | CHFCH₃ | H | CH₃ | OC₂H₅ | |
| H | CHFCH₃ | H | CH₃ | CH₂OCH₃ | |
| H | CHFCH₃ | H | OCH₃ | CH₂OCH₃ | |
| H | CHFCH₃ | H | OCH₃ | C₂H₅ | |
| H | CHFCH₃ | H | OC₂H₅ | OCH₃ | |
| H | CHFCH₃ | H | OCH₂CF₃ | OCH₃ | |
| H | CHFCH₃ | H | CF₃ | OCH₃ | |
| H | CHFCH₃ | H | CH₂F | OCH₃ | |
| H | CHFCH₃ | H | CH₂Cl | OCH₃ | |
| H | CHFCH₃ | H | CH₂Br | OCH₃ | |
| H | CHFCH₃ | H | F | OCH₃ | |
| H | CHFCH₃ | H | I | OCH₃ | |
| H | CHFCH₃ | H | OCH₂CH₂F | OCH₃ | |
| H | CHFCH₃ | H | OCH₂CH₂CF₃ | OCH₃ | |
| H | CHFCH₃ | H | OCH₂CHF₂ | CH₃ | |
| H | CHFCH₃ | H | OCH₂CF₃ | CH₃ | |
| H | CHFCH₃ | H | Cl | OC₂H₅ | |

TABLE 34-continued

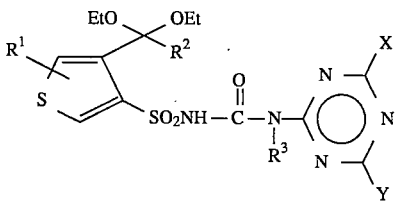

| R¹ | R² | R³ | X | Y | mp (°C.) |
|---|---|---|---|---|---|
| H | CHFCH₃ | H | OC₂H₅ | NHCH₃ | |
| H | CHFCH₃ | H | OCH₃ | CH₂SCH₃ | |
| H | CHFCH₃ | H | OCF₂H | CH₃ | |
| H | CHFCH₃ | H | Cl | OCF₂H | |
| H | CH₂CH₂F | H | OCH₃ | OCH₃ | |
| H | CH₂CH₂F | H | CH₃ | OCH₃ | |
| H | CH₂CH₂F | H | CH₃ | CH₃ | |
| H | CH₂CH₂F | H | Cl | OCH₃ | |
| H | CH₂CH₂F | H | Br | OCH₃ | |
| H | CH₂CH₂F | H | CH₃ | H | |
| H | CH₂CH₂F | H | OCH₃ | H | |
| H | CH₂CH₂F | H | OCH₃ | CH₂OC₂H₅ | |
| H | CH₂CH₂F | H | OCF₂H | OCH₃ | |
| H | CH₂CH₂F | H | OCH₃ | CH(OCH₃)₂ | |
| H | CH₂CH₂F | H | CH₃ | OC₂H₅ | |
| H | CH₂CH₂F | H | CH₃ | CH₂OCH₃ | |
| H | CH₂CH₂F | H | OCH₃ | CH₂OCH₃ | |
| H | CH₂CH₂F | H | OCH₃ | C₂H₅ | |
| H | CH₂CH₂F | H | OC₂H₅ | OCH₃ | |
| H | CH₂CH₂F | H | OCH₂CF₃ | OCH₃ | |
| H | CH₂CH₂F | H | CF₃ | OCH₃ | |
| H | CH₂CH₂F | H | CH₂F | OCH₃ | |
| H | CH₂CH₂F | H | CH₂Cl | OCH₃ | |
| H | CH₂CH₂F | H | CH₂Br | OCH₃ | |
| H | CH₂CH₂F | H | F | OCH₃ | |
| H | CH₂CH₂F | H | I | OCH₃ | |
| H | CH₂CH₂F | H | OCH₂CH₂F | OCH₃ | |
| H | CH₂CH₂F | H | OCH₂CH₂CF₃ | OCH₃ | |
| H | CH₂CH₂F | H | OCH₂CHF₂ | CH₃ | |
| H | CH₂CH₂F | H | OCH₂CF₃ | CH₃ | |
| H | CH₂CH₂F | H | Cl | OC₂H₅ | |
| H | CH₂CH₂F | H | OC₂H₅ | NHCH₃ | |
| H | CH₂CH₂F | H | OCH₃ | CH₂SCH₃ | |
| H | CH₂CH₂F | H | OCF₂H | CH₃ | |
| H | CH₂CH₂F | H | Cl | OCF₂H | |
| H | CH₂Cl | H | OCH₃ | OCH₃ | |
| H | CH₂Cl | H | CH₃ | OCH₃ | |
| H | CH₂Cl | H | CH₃ | CH₃ | |
| H | CH₂Cl | H | Cl | OCH₃ | |
| H | CH₂Cl | H | Br | OCH₃ | |
| H | CH₂Cl | H | CH₃ | H | |
| H | CH₂Cl | H | OCH₃ | H | |
| H | CH₂Cl | H | OCH₃ | CH₂OC₂H₅ | |
| H | CH₂Cl | H | OCF₂H | OCH₃ | |
| H | CH₂Cl | H | OCH₃ | CH(OCH₃)₂ | |
| H | CH₂Cl | H | CH₃ | OC₂H₅ | |
| H | CH₂Cl | H | CH₃ | CH₂OCH₃ | |
| H | CH₂Cl | H | OCH₃ | CH₂OCH₃ | |
| H | CH₂Cl | H | OCH₃ | C₂H₅ | |
| H | CH₂Cl | H | OC₂H₅ | OCH₃ | |
| H | CH₂Cl | H | OCH₂CF₃ | OCH₃ | |
| H | CH₂Cl | H | CF₃ | OCH₃ | |
| H | CH₂Cl | H | CH₂F | OCH₃ | |
| H | CH₂Cl | H | CH₂Cl | OCH₃ | |
| H | CH₂Cl | H | CH₂Br | OCH₃ | |
| H | CH₂Cl | H | F | OCH₃ | |
| H | CH₂Cl | H | I | OCH₃ | |
| H | CH₂Cl | H | OCH₂CH₂F | OCH₃ | |
| H | CH₂Cl | H | OCH₂CH₂CF₃ | OCH₃ | |
| H | CH₂Cl | H | OCH₂CHF₂ | CH₃ | |
| H | CH₂Cl | H | OCH₂CF₃ | CH₃ | |
| H | CH₂Cl | H | Cl | OC₂H₅ | |
| H | CH₂Cl | H | OC₂H₅ | NHCH₃ | |
| H | CH₂Cl | H | OCH₃ | CH₂SCH₃ | |
| H | CH₂Cl | H | OCF₂H | CH₃ | |
| H | CH₂Br | H | Cl | OCF₂H | |
| H | CH₂Br | H | OCH₃ | OCH₃ | |

TABLE 34-continued

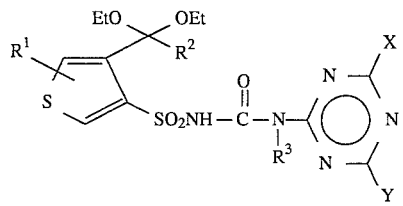

| R¹ | R² | R³ | X | Y | mp (°C.) |
|---|---|---|---|---|---|
| H | CH₂Br | H | CH₃ | OCH₃ | |
| H | CH₂Br | H | CH₃ | CH₃ | |
| H | CH₂Br | H | Cl | OCH₃ | |
| H | CH₂Br | H | Br | OCH₃ | |
| H | CH₂Br | H | CH₃ | H | |
| H | CH₂Br | H | OCH₃ | H | |
| H | CH₂Br | H | OCH₃ | CH₂OC₂H₅ | |
| H | CH₂Br | H | OCF₂H | OCH₃ | |
| H | CH₂Br | H | OCH₃ | CH(OCH₃)₂ | |
| H | CH₂Br | H | CH₃ | OC₂H₅ | |
| H | CH₂Br | H | CH₃ | CH₂OCH₃ | |
| H | CH₂Br | H | OCH₃ | CH₂OCH₃ | |
| H | CH₂Br | H | OCH₃ | C₂H₅ | |
| H | CH₂Br | H | OC₂H₅ | OCH₃ | |
| H | CH₂Br | H | OCH₂CF₃ | OCH₃ | |
| H | CH₂Br | H | CF₃ | OCH₃ | |
| H | CH₂Br | H | CH₂F | OCH₃ | |
| H | CH₂Br | H | CH₂Cl | OCH₃ | |
| H | CH₂Br | H | CH₂Br | OCH₃ | |
| H | CH₂Br | H | F | OCH₃ | |
| H | CH₂Br | H | I | OCH₃ | |
| H | CH₂Br | H | OCH₂CH₂F | OCH₃ | |
| H | CH₂Br | H | OCH₂CH₂CF₃ | OCH₃ | |
| H | CH₂Br | H | OCH₂CHF₂ | CH₃ | |
| H | CH₂Br | H | OCH₂CF₃ | CH₃ | |
| H | CH₂Br | H | Cl | OC₂H₅ | |
| H | CH₂Br | H | OC₂H₅ | NHCH₃ | |
| H | CH₂Br | H | OCH₃ | CH₂SCH₃ | |
| H | CH₂Br | H | OCF₂H | CH₃ | |
| H | CH₂Br | H | Cl | OCF₂H | |

TABLE 35

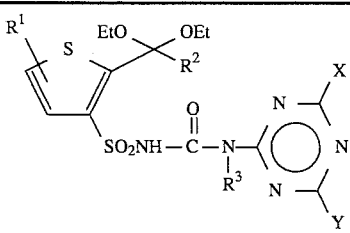

| R¹ | R² | R³ | X | Y | mp (°C.) |
|---|---|---|---|---|---|
| H | CH₂F | H | CH₃ | OCH₃ | |
| H | CH₂F | H | OCH₃ | OCH₃ | |
| H | CH₂F | H | OC₂H₅ | NHCH₃ | |
| H | CH₂F | H | OCH₃ | N(OCH₃)(CH₃) | |
| H | CH₂F | H | OCH₃ | N(CH₃)₂ | |
| H | CH₂Cl | H | CH₃ | OCH₃ | |
| H | CH₂Cl | H | OCH₃ | OCH₃ | |
| H | CH₂Cl | H | OC₂H₅ | NHCH₃ | |
| H | CH₂Cl | H | OCH₃ | N(OCH₃)(CH₃) | |
| H | CH₂Cl | H | OCH₃ | N(CH₃)₂ | |
| H | CH₂Br | H | CH₃ | OCH₃ | |
| H | CH₂Br | H | OCH₃ | OCH₃ | |
| H | CH₂Br | H | OC₂H₅ | NHCH₃ | |
| H | CH₂Br | H | OCH₃ | N(OCH₃)(CH₃) | |
| H | CH₂Br | H | OCH₃ | N(CH₃)₂ | |
| H | CHF₂ | H | CH₃ | OCH₃ | |
| H | CHF₂ | H | OCH₃ | OCH₃ | |
| H | CHF₂ | H | OC₂H₅ | NHCH₃ | |

TABLE 35-continued

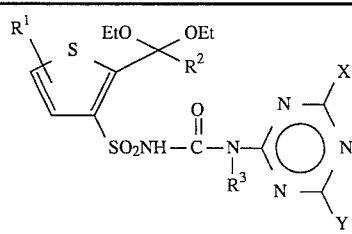

| R¹ | R² | R³ | X | Y | mp (°C.) |
|---|---|---|---|---|---|
| H | CHF₂ | H | OCH₃ | N(OCH₃)(CH₃) | |
| H | CHF₂ | H | OCH₃ | N(CH₃)₂ | |
| H | CH₂F | CH₃ | OCH₃ | OCH₃ | |
| H | CH₂Cl | CH₃ | OCH₃ | OCH₃ | |
| H | CH₂F | CH₃ | CH₃ | OCH₃ | |
| H | CH₂Br | CH₃ | OCH₃ | OCH₃ | |
| H | CH₂Cl | CH₃ | CH₃ | OCH₃ | |
| H | CH₂Br | CH₃ | CH₃ | OCH₃ | |
| H | CHF₂ | CH₃ | OCH₃ | OCH₃ | |
| H | CHF₂ | CH₃ | CH₃ | OCH₃ | |
| H | CH₂F | CH₃ | OC₂H₅ | NHCH₃ | |
| H | CH₂F | CH₃ | OCH₃ | N(CH₃)₂ | |
| H | CHFCH₃ | H | CH₃ | OCH₃ | |
| H | CHFCH₃ | H | OCH₃ | OCH₃ | |
| H | CHFCH₃ | H | OC₂H₅ | NHCH₃ | |
| H | CHFCH₃ | H | OCH₃ | N(OCH₃)(CH₃) | |
| H | CHFCH₃ | H | OCH₃ | N(CH₃)₂ | |
| H | CHClCH₃ | H | CH₃ | OCH₃ | |

TABLE 35-continued

| R¹ | R² | R³ | X | Y | mp (°C.) |
|---|---|---|---|---|---|
| H | CHClCH₃ | H | OCH₃ | OCH₃ | |
| H | CHClCH₃ | H | OC₂H₅ | NHCH₃ | |
| H | CHClCH₃ | H | OCH₃ | N(OCH₃)(CH₃) | |
| H | CHClCH₃ | H | OCH₃ | N(CH₃)₂ | |
| H | CH₂CH₂F | H | CH₃ | OCH₃ | |
| H | CH₂CH₂F | H | OCH₃ | OCH₃ | |
| H | CH₂CH₂F | H | OC₂H₅ | NHCH₃ | |
| H | CH₂CH₂F | H | OCH₃ | N(OCH₃)(CH₃) | |
| H | CH₂CH₂F | H | OCH₃ | N(CH₃)₂ | |
| H | CHFCl | H | OCH₃ | OCH₃ | |
| H | CHFCl | H | CH₃ | OCH₃ | |
| H | CHFCl | H | CH₃ | CH₃ | |
| H | CHFCl | H | Cl | OCH₃ | |
| H | CHFCl | H | OCH₃ | CH₂OCH₃ | |
| H | CHFCl | H | CH₃ | OC₂H₅ | |
| H | CHFCl | H | CH₂Cl | OCH₃ | |
| H | CHFCl | H | F | OCH₃ | |
| H | CHFCl | H | OCH₃ | CH(OCH₃)₂ | |
| H | CHFCl | H | OCHF₂ | OCH₃ | |
| H | CHFCl | H | C₂H₅ | OCH₃ | |
| 5-F | CH₂F | H | CH₃ | OCH₃ | |

TABLE 36

| R¹ | R² | R³ | X | Y | mp (°C.) |
|---|---|---|---|---|---|
| H | CH₂F | H | CH₃ | OCH₃ | |
| H | CH₂F | H | OCH₃ | OCH₃ | |
| H | CH₂F | H | OC₂H₅ | NHCH₃ | |
| H | CH₂F | H | OCH₃ | N(OCH₃)(CH₃) | |
| H | CH₂F | H | OCH₃ | N(CH₃)₂ | |
| H | CH₂Cl | H | CH₃ | OCH₃ | |
| H | CH₂Cl | H | OCH₃ | OCH₃ | |
| H | CH₂Cl | H | OC₂H₅ | NHCH₃ | |
| H | CH₂Cl | H | OCH₃ | N(OCH₃)(CH₃) | |
| H | CH₂Cl | H | OCH₃ | N(CH₃)₂ | |
| H | CH₂Br | H | CH₃ | OCH₃ | |
| H | CH₂Br | H | OCH₃ | OCH₃ | |
| H | CH₂Br | H | OC₂H₅ | NHCH₃ | |
| H | CH₂Br | H | OCH₃ | N(OCH₃)(CH₃) | |
| H | CH₂Br | H | OCH₃ | N(CH₃)₂ | |
| H | CHF₂ | H | CH₃ | OCH₃ | |
| H | CHF₂ | H | OCH₃ | OCH₃ | |
| H | CHF₂ | H | OC₂H₅ | NHCH₃ | |
| H | CHF₂ | H | OCH₃ | N(OCH₃)(CH₃) | |
| H | CHF₂ | H | OCH₃ | N(CH₃)₂ | |
| H | CH₂F | CH₃ | OCH₃ | OCH₃ | |
| H | CH₂Cl | CH₃ | OCH₃ | OCH₃ | |
| H | CH₂F | CH₃ | CH₃ | OCH₃ | |
| H | CH₂Br | CH₃ | OCH₃ | OCH₃ | |
| H | CH₂Cl | CH₃ | CH₃ | OCH₃ | |
| H | CH₂Br | CH₃ | CH₃ | OCH₃ | |
| H | CHF₂ | CH₃ | OCH₃ | OCH₃ | |
| H | CHF₂ | CH₃ | CH₃ | OCH₃ | |

TABLE 36-continued

| R¹ | R² | R³ | X | Y | mp (°C.) |
|---|---|---|---|---|---|
| H | CH₂F | CH₃ | OC₂H₅ | NHCH₃ | |
| H | CH₂F | CH₃ | OCH₃ | N(CH₃)₂ | |
| H | CHFCH₃ | H | CH₃ | OCH₃ | |
| H | CHFCH₃ | H | OCH₃ | OCH₃ | |
| H | CHFCH₃ | H | OC₂H₅ | NHCH₃ | |
| H | CHFCH₃ | H | OCH₃ | N(OCH₃)(CH₃) | |
| H | CHFCH₃ | H | OCH₃ | N(CH₃)₂ | |
| H | CHClCH₃ | H | CH₃ | OCH₃ | |
| H | CHClCH₃ | H | OCH₃ | OCH₃ | |
| H | CHClCH₃ | H | OC₂H₅ | NHCH₃ | |
| H | CHClCH₃ | H | OCH₃ | N(OCH₃)(CH₃) | |
| H | CHClCH₃ | H | OCH₃ | N(CH₃)₂ | |
| H | CH₂CH₂F | H | CH₃ | OCH₃ | |
| H | CH₂CH₂F | H | OCH₃ | OCH₃ | |
| H | CH₂CH₂F | H | OC₂H₅ | NHCH₃ | |
| H | CH₂CH₂F | H | OCH₃ | N(OCH₃)(CH₃) | |
| H | CH₂CH₂F | H | OCH₃ | N(CH₃)₂ | |
| H | CHFCl | H | OCH₃ | OCH₃ | |
| H | CHFCl | H | CH₃ | OCH₃ | |
| H | CHFCl | H | CH₃ | CH₃ | |
| H | CHFCl | H | Cl | OCH₃ | |
| H | CHFCl | H | OCH₃ | CH₂OCH₃ | |
| H | CHFCl | H | CH₃ | OC₂H₅ | |
| H | CHFCl | H | CH₂Cl | OCH₃ | |
| H | CHFCl | H | F | OCH₃ | |
| H | CHFCl | H | OCH₃ | CH(OCH₃)₂ | |
| H | CHFCl | H | OCHF₂ | OCH₃ | |
| H | CHFCl | H | C₂H₅ | OCH₃ | |
| 5-F | CH₂F | H | CH₃ | OCH₃ | |

TABLE 37

| R¹ | R² | R³ | X | Y | mp (°C.) |
|---|---|---|---|---|---|
| H | CH₂F | H | CH₃ | OCH₃ | 148–150 |
| H | CH₂F | H | OCH₃ | OHC₃ | 157–158 |
| H | CH₂F | H | OC₂H₅ | NHCH₃ | |
| H | CH₂F | H | OCH₃ | N(OCH₃)(CH₃) | |
| H | CH₂F | H | OCH₃ | N(CH₃)₂ | |
| H | CH₂Cl | H | CH₃ | OCH₃ | |
| H | CH₂Cl | H | OCH₃ | OCH₃ | |
| H | CH₂Cl | H | OC₂H₅ | NHCH₃ | |
| H | CH₂Cl | H | OCH₃ | N(OCH₃)(CH₃) | |
| H | CH₂Cl | H | OCH₃ | N(CH₃)₂ | |
| H | CH₂Br | H | CH₃ | OCH₃ | |
| H | CH₂Br | H | OCH₃ | OCH₃ | |
| H | CH₂Br | H | OC₂H₅ | NHCH₃ | |
| H | CH₂Br | H | OCH₃ | N(OCH₃)(CH₃) | |
| H | CH₂Br | H | OCH₃ | N(CH₃)₂ | |
| H | CHF₂ | H | CH₃ | OCH₃ | |
| H | CHF₂ | H | OCH₃ | OCH₃ | |
| H | CHF₂ | H | OC₂H₅ | NHCH₃ | |
| H | CHF₂ | H | OCH₃ | N(OCH₃)(CH₃) | |
| H | CHF₂ | H | OCH₃ | N(CH₃)₂ | |
| H | CH₂F | CH₃ | OCH₃ | OCH₃ | |

TABLE 37-continued

| R¹ | R² | R³ | X | Y | mp (°C.) |
|---|---|---|---|---|---|
| H | CH₂Cl | CH₃ | OCH₃ | OCH₃ | |
| H | CH₂F | CH₃ | CH₃ | OCH₃ | |
| H | CH₂Br | CH₃ | OCH₃ | OCH₃ | |
| H | CH₂Cl | CH₃ | CH₃ | OCH₃ | |
| H | CH₂Br | CH₃ | CH₃ | OCH₃ | |
| H | CHF₂ | CH₃ | OCH₃ | OCH₃ | |
| H | CHF₂ | CH₃ | CH₃ | OCH₃ | |
| H | CH₂F | CH₃ | OC₂H₅ | NHCH₃ | |
| H | CH₂F | CH₃ | OCH₃ | N(CH₃)₂ | |
| H | CHFCH₃ | H | CH₃ | OCH₃ | |
| H | CHFCH₃ | H | OCH₃ | OCH₃ | |
| H | CHFCH₃ | H | OC₂H₅ | NHCH₃ | |
| H | CHFCH₃ | H | OCH₃ | N(OCH₃)(CH₃) | |
| H | CHFCH₃ | H | OCH₃ | N(CH₃)₂ | |
| H | CHClCH₃ | H | CH₃ | OCH₃ | |
| H | CHClCH₃ | H | OCH₃ | OCH₃ | |
| H | CHClCH₃ | H | OC₂H₅ | NHCH₃ | |
| H | CHClCH₃ | H | OCH₃ | N(OCH₃)(CH₃) | |
| H | CHClCH₃ | H | OCH₃ | N(CH₃)₂ | |
| H | CH₂CH₂F | H | CH₃ | OCH₃ | |
| H | CH₂CH₂F | H | OCH₃ | OCH₃ | |
| H | CH₂CH₂F | H | OC₂H₅ | NHCH₃ | |
| H | CH₂CH₂F | H | OCH₃ | N(OCH₃)(CH₃) | |
| H | CH₂CH₂F | H | OCH₃ | N(CH₃)₂ | |
| H | CHFCl | H | OCH₃ | OCH₃ | |
| H | CHFCl | H | CH₃ | OCH₃ | |
| H | CHFCl | H | CH₃ | CH₃ | |
| H | CHFCl | H | Cl | OCH₃ | |
| H | CHFCl | H | OCH₃ | CH₂OCH₃ | |
| H | CHFCl | H | CH₃ | OC₂H₅ | |
| H | CHFCl | H | CH₂Cl | OCH₃ | |
| H | CHFCl | H | F | OCH₃ | |
| H | CHFCl | H | OCH₃ | CH(OCH₃)₂ | |
| H | CHFCl | H | OCHF₂ | OCH₃ | |
| H | CHFCl | H | C₂H₅ | OCH₃ | |
| 5-F | CH₂F | H | CH₃ | OCH₃ | |

TABLE 38

| R¹ | R² | R³ | X | Y | mp (°C.) |
|---|---|---|---|---|---|
| H | CH₂F | H | CH₃ | OCH₃ | |
| H | CH₂F | H | OCH₃ | OCH₃ | |
| H | CH₂F | H | OC₂H₅ | NHCH₃ | |
| H | CH₂F | H | OCH₃ | N(OCH₃)(CH₃) | |
| H | CH₂F | H | OCH₃ | N(CH₃)₂ | |
| H | CH₂Cl | H | CH₃ | OCH₃ | |
| H | CH₂Cl | H | OCH₃ | OCH₃ | |
| H | CH₂Cl | H | OC₂H₅ | NHCH₃ | |
| H | CH₂Cl | H | OCH₃ | N(OCH₃)(CH₃) | |
| H | CH₂Cl | H | OCH₃ | N(CH₃)₂ | |
| H | CH₂Br | H | CH₃ | OCH₃ | |
| H | CH₂Br | H | OCH₃ | OCH₃ | |
| H | CH₂Br | H | OC₂H₅ | NHCH₃ | |
| H | CH₂Br | H | OCH₃ | N(OCH₃)(CH₃) | |
| H | CH₂Br | H | OCH₃ | N(CH₃)₂ | |
| H | CHF₂ | H | CH₃ | OCH₃ | |
| H | CHF₂ | H | OCH₃ | OCH₃ | |
| H | CHF₂ | H | OC₂H₅ | NHCH₃ | |
| H | CHF₂ | H | OCH₃ | N(OCH₃)(CH₃) | |
| H | CHF₃ | H | OCH₃ | N(CH₃)₂ | |
| H | CH₂F | CH₃ | OCH₃ | OCH₃ | |
| H | CH₂Cl | CH₃ | OCH₃ | OCH₃ | |
| H | CH₂F | CH₃ | CH₃ | OCH₃ | |
| H | CH₂Br | CH₃ | OCH₃ | OCH₃ | |
| H | CH₂Cl | CH₃ | CH₃ | OCH₃ | |
| H | CH₂Br | CH₃ | CH₃ | OCH₃ | |
| H | CHF₂ | CH₃ | OCH₃ | OCH₃ | |
| H | CHF₂ | CH₃ | CH₃ | OCH₃ | |
| H | CH₂F | CH₃ | OC₂H₅ | NHCH₃ | |
| H | CH₂F | CH₃ | OCH₃ | N(CH₃)₂ | |
| H | CHFCH₃ | H | CH₃ | OCH₃ | |
| H | CHFCH₃ | H | OCH₃ | OCH₃ | |
| H | CHFCH₃ | H | OC₂H₅ | NHCH₃ | |
| H | CHFCH₃ | H | OCH₃ | N(OCH₃)(CH₃) | |
| H | CHFCH₃ | H | OCH₃ | N(CH₃)₂ | |
| H | CHClCH₃ | H | CH₃ | OCH₃ | |
| H | CHClCH₃ | H | OCH₃ | OCH₃ | |
| H | CHClCH₃ | H | OC₂H₅ | NHCH₃ | |
| H | CHClCH₃ | H | OCH₃ | N(OCH₃)(CH₃) | |
| H | CHClCH₃ | H | OCH₃ | N(CH₃)₂ | |
| H | CH₂CH₂F | H | CH₃ | OCH₃ | |
| H | CH₂CH₂F | H | OCH₃ | OCH₃ | |
| H | CH₂CH₂F | H | OC₂H₅ | NHCH₃ | |
| H | CH₂CH₂F | H | OCH₃ | N(OCH₃)(CH₃) | |
| H | CH₂CH₂F | H | OCH₃ | N(CH₃)₂ | |
| H | CHFCl | H | OCH₃ | OCH₃ | |
| H | CHFCl | H | CH₃ | OCH₃ | |
| H | CHFCl | H | CH₃ | CH₃ | |
| H | CHFCl | H | Cl | OCH₃ | |
| H | CHFCl | H | OCH₃ | CH₂OCH₃ | |
| H | CHFCl | H | CH₃ | OC₂H₅ | |
| H | CHFCl | H | CH₂Cl | OHC₃ | |
| H | CHFCl | H | F | OCH₃ | |
| H | CHFCl | H | OCH₃ | CH(OCH₃)₂ | |
| H | CHFCl | H | OCHF₂ | OCH₃ | |
| H | CHFCl | H | C₂H₅ | OCH₃ | |
| 5-F | CH₂F | H | CH₃ | OCH₃ | |

TABLE 39

| R¹ | R² | R³ | X | Y | mp (°C.) |
|---|---|---|---|---|---|
| H | CH₂F | H | CH₃ | OCH₃ | |
| H | CH₂F | H | OCH₃ | OCH₃ | |
| H | CH₂F | H | OC₂H₅ | NHCH₃ | |
| H | CH₂F | H | OCH₃ | N(OCH₃)(CH₃) | |
| H | CH₂F | H | OCH₃ | N(CH₃)₂ | |

TABLE 39-continued

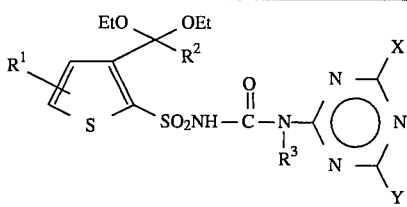

| R¹ | R² | R³ | X | Y | mp (°C.) |
|---|---|---|---|---|---|
| H | CH₂Cl | H | CH₃ | OCH₃ | |
| H | CH₂Cl | H | OCH₃ | OCH₃ | |
| H | CH₂Cl | H | OC₂H₅ | NHCH₃ | |
| H | CH₂Cl | H | OCH₃ | N(OCH₃)(CH₃) | |
| H | CH₂Cl | H | OCH₃ | N(CH₃)₂ | |
| H | CH₂Br | H | CH₃ | OCH₃ | |
| H | CH₂Br | H | OCH₃ | OCH₃ | |
| H | CH₂Br | H | OC₂H₅ | NHCH₃ | |
| H | CH₂Br | H | OCH₃ | N(OCH₃)(CH₃) | |
| H | CH₂Br | H | OCH₃ | N(CH₃)₂ | |
| H | CHF₂ | H | CH₃ | OCH₃ | |
| H | CHF₂ | H | OCH₃ | OCH₃ | |
| H | CHF₂ | H | OC₂H₅ | NHCH₃ | |
| H | CHF₂ | H | OCH₃ | N(OCH₃)(CH₃) | |
| H | CHF₂ | H | OCH₃ | N(CH₃)₂ | |
| H | CHF₂ | H | OCH₃ | OCH₃ | |
| H | CH₂Cl | CH₃ | OCH₃ | OCH₃ | |
| H | CH₂F | CH₃ | CH₃ | OCH₃ | |
| H | CH₂Br | CH₃ | OCH₃ | OCH₃ | |
| H | CH₂Cl | CH₃ | CH₃ | OCH₃ | |
| H | CH₂Br | CH₃ | CH₃ | OCH₃ | |
| H | CHF₂ | CH₃ | OCH₃ | OCH₃ | |
| H | CHF₂ | CH₃ | CH₃ | OCH₃ | |
| H | CH₂F | CH₃ | OC₂H₅ | NHCH₃ | |
| H | CH₂F | CH₃ | OCH₃ | N(CH₃)₂ | |
| H | CHFCH₃ | H | CH₃ | OCH₃ | |
| H | CHFCH₃ | H | OCH₃ | OCH₃ | |
| H | CHFCH₃ | H | OC₂H₅ | NHCH₃ | |
| H | CHFCH₃ | H | OCH₃ | N(OCH₃)(CH₃) | |
| H | CHFCH₃ | H | OCH₃ | N(CH₃)₂ | |
| H | CHClCH₃ | H | CH₃ | OCH₃ | |
| H | CHClCH₃ | H | OCH₃ | OCH₃ | |
| H | CHClCH₃ | H | OC₂H₅ | NHCH₃ | |
| H | CHClCH₃ | H | OCH₃ | N(OCH₃)(CH₃) | |
| H | CHClCH₃ | H | OCH₃ | N(CH₃)₂ | |
| H | CH₂CH₂F | H | CH₃ | OCH₃ | |
| H | CH₂CH₂F | H | OCH₃ | OCH₃ | |
| H | CH₂CH₂F | H | OC₂H₅ | NHCH₃ | |
| H | CH₂CH₂F | H | OCH₃ | N(OCH₃)(CH₃) | |
| H | CH₂CH₂F | H | OCH₃ | N(CH₃)₂ | |
| H | CHFCl | H | OCH₃ | OCH₃ | |
| H | CHFCl | H | CH₃ | OCH₃ | |
| H | CHFCl | H | CH₃ | CH₃ | |
| H | CHFCl | H | Cl | OCH₃ | |
| H | CHFCl | H | OCH₃ | CH₂OCH₃ | |
| H | CHFCl | H | CH₃ | OC₂H₅ | |
| H | CHFCl | H | CH₂Cl | OCH₃ | |
| H | CHFCl | H | F | OCH₃ | |
| H | CHFCl | H | OCH₃ | CH(OCH₃)₂ | |
| H | CHFCl | H | OCHF₂ | OCH₃ | |
| H | CHFCl | H | C₂H₅ | OCH₃ | |
| 5-F | CH₂F | H | CH₃ | OCH₃ | |

TABLE 40

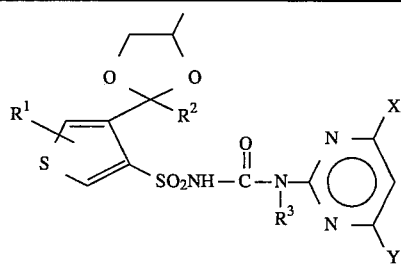

| R¹ | R² | R³ | X | Y | mp (°C.) |
|---|---|---|---|---|---|
| H | CH₂F | H | CH₃ | OCH₃ | |
| H | CH₂F | H | OCH₃ | OCH₃ | 169–172 |
| H | CH₂F | H | OC₂H₅ | NHCH₃ | |
| H | CH₂F | H | OCH₃ | N(OCH₃)(CH₃) | |
| H | CH₂F | H | OCH₃ | N(CH₃)₂ | |
| H | CH₂F | H | CH₃ | Cl | 174–178 |
| H | CH₂Cl | H | OCH₃ | OCH₃ | |
| H | CH₂F | H | OC₂H₅ | Cl | 142–148 |
| H | CH₂Cl | H | OCH₃ | N(OCH₃)(CH₃) | |
| H | CH₂Cl | H | OCH₃ | N(CH₃)₂ | |
| H | CH₂Br | H | CH₃ | OCH₃ | |
| H | CH₂Br | H | OCH₃ | OCH₃ | |
| H | CH₂Br | H | OC₂H₅ | NHCH₃ | |
| H | CH₂Br | H | OCH₃ | N(OCH₃)(CH₃) | |
| H | CH₂Br | H | OCH₃ | N(CH₃)₂ | |
| H | CH₂F | H | CH₃ | CH₃ | 162–165 |
| H | CHF₂ | H | OCH₃ | OCH₃ | |
| H | CHF₂ | H | OC₂H₅ | NHCH₃ | |
| H | CHF₂ | H | OCH₃ | N(OCH₃)(CH₃) | |
| H | CHF₂ | H | OCH₃ | N(CH₃)₂ | |
| H | CH₂F | CH₃ | OCH₃ | OCH₃ | |
| H | CH₂Cl | CH₃ | OCH₃ | OCH₃ | |
| H | CH₂F | CH₃ | CH₃ | OCH₃ | |
| H | CH₂Br | CH₃ | OCH₃ | OCH₃ | |
| H | CH₂Cl | CH₃ | CH₃ | OCH₃ | |
| H | CH₂Br | CH₃ | CH₃ | OCH₃ | |
| H | CHF₂ | CH₃ | OCH₃ | OCH₃ | |
| H | CHF₂ | CH₃ | CH₃ | OCH₃ | |
| H | CH₂F | CH₃ | OC₂H₅ | NHCH₃ | |
| H | CH₂F | CH₃ | OCH₃ | N(CH₃)₂ | |
| H | CHFCH₃ | H | CH₃ | OCH₃ | |
| H | CHFCH₃ | H | OCH₃ | OCH₃ | |
| H | CHFCH₃ | H | OC₂H₅ | NHCH₃ | |
| H | CHFCH₃ | H | OCH₃ | N(OCH₃)(CH₃) | |
| H | CHFCH₃ | H | OCH₃ | N(CH₃)₂ | |
| H | CHClCH₃ | H | CH₃ | OCH₃ | |
| H | CHClCH₃ | H | OCH₃ | OCH₃ | |
| H | CHClCH₃ | H | OC₂H₅ | NHCH₃ | |
| H | CHClCH₃ | H | OCH₃ | N(OCH₃)(CH₃) | |
| H | CHClCH₃ | H | OCH₃ | N(CH₃)₂ | |
| H | CH₂CH₂F | H | CH₃ | OCH₃ | |
| H | CH₂CH₂F | H | OCH₃ | OCH₃ | |
| H | CH₂CH₂F | H | OC₂H₅ | NHCH₃ | |
| H | CH₂CH₂F | H | OCH₃ | N(OCH₃)(CH₃) | |
| H | CH₂CH₂F | H | OCH₃ | N(CH₃)₂ | |
| H | CHFCl | H | OCH₃ | OCH₃ | OCH₃ |
| H | CHFCl | H | CH₃ | OCH₃ | |
| H | CHFCl | H | CH₃ | CH₃ | |
| H | CHFCl | H | Cl | OCH₃ | |
| H | CHFCl | H | OCH₃ | CH₂OCH₃ | |
| H | CHFCl | H | CH₃ | OC₂H₅ | |
| H | CHFCl | H | CH₂Cl | OCH₃ | |
| H | CHFCl | H | F | OCH₃ | |
| H | CHFCl | H | OCH₃ | CH(OCH₃)₂ | |
| H | CHFCl | H | OCHF₂ | OCH₃ | |
| H | CHFCl | H | C₂H₅ | OCH₃ | |
| 5-F | CH₂F | H | CH₃ | OCH₃ | |

TABLE 41

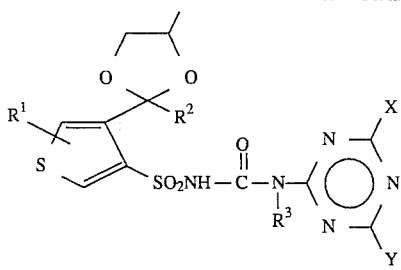

| R¹ | R² | R³ | X | Y | mp (°C.) |
|---|---|---|---|---|---|
| H | CH₂F | H | CH₃ | OCH₃ | 131–133 |
| H | CH₂F | H | OCH₃ | OCH₃ | 145–148 |
| H | CH₂F | H | OC₂H₅ | NHCH₃ | |
| H | CH₂F | H | OCH₃ | N(OCH₃)(CH₃) | |
| H | CH₂F | H | OCH₃ | N(CH₃)₂ | |
| H | CH₂Cl | H | CH₃ | OCH₃ | |
| H | CH₂Cl | H | OCH₃ | OCH₃ | |
| H | CH₂Cl | H | OC₂H₅ | NHCH₃ | |
| H | CH₂Cl | H | OCH₃ | N(OCH₃)(CH₃) | |
| H | CH₂Cl | H | OCH₃ | N(CH₃)₂ | |
| H | CH₂Br | H | CH₃ | OCH₃ | |
| H | CH₂Br | H | OCH₃ | OCH₃ | |
| H | CH₂Br | H | OC₂H₅ | NHCH₃ | |
| H | CH₂Br | H | OCH₃ | N(OCH₃)(CH₃) | |
| H | CH₂Br | H | OCH₃ | N(CH₃)₂ | |
| H | CHF₂ | H | CH₃ | OCH₃ | |
| H | CHF₂ | H | OCH₃ | OCH₃ | |
| H | CHF₂ | H | OC₂H₅ | NHCH₃ | |
| H | CHF₂ | H | OCH₃ | N(OCH₃)(CH₃) | |
| H | CHF₂ | H | OCH₃ | N(CH₃)₂ | |
| H | CH₂F | CH₃ | OCH₃ | OCH₃ | |
| H | CH₂Cl | CH₃ | OCH₃ | OCH₃ | |
| H | CH₂F | CH₃ | CH₃ | OCH₃ | |
| H | CH₂Br | CH₃ | OCH₃ | OCH₃ | |
| H | CH₂Cl | CH₃ | CH₃ | OCH₃ | |
| H | CH₂Br | CH₃ | CH₃ | OCH₃ | |
| H | CHF₂ | CH₃ | OCH₃ | OCH₃ | |
| H | CHF₂ | CH₃ | CH₃ | OCH₃ | |
| H | CH₂F | CH₃ | OC₂H₅ | NHCH₃ | |
| H | CH₂F | CH₃ | OCH₃ | N(CH₃)₂ | |
| H | CHFCH₃ | H | CH₃ | OCH₃ | |
| H | CHFCH₃ | H | OCH₃ | OCH₃ | |
| H | CHFCH₃ | H | OC₂H₅ | NHCH₃ | |
| H | CHFCH₃ | H | OCH₃ | N(OCH₃)(CH₃) | |
| H | CHFCH₃ | H | OCH₃ | N(CH₃)₂ | |
| H | CHClCH₃ | H | CH₃ | OCH₃ | |
| H | CHClCH₃ | H | OCH₃ | OCH₃ | |
| H | CHClCH₃ | H | OC₂H₅ | NHCH₃ | |
| H | CHClCH₃ | H | OCH₃ | N(OCH₃)(CH₃) | |
| H | CHClCH₃ | H | OCH₃ | N(CH₃)₂ | |
| H | CH₂CH₂F | H | CH₃ | OCH₃ | |
| H | CH₂CH₂F | H | OCH₃ | OCH₃ | |
| H | CH₂CH₂F | H | OC₂H₅ | NHCH₃ | |
| H | CH₂CH₂F | H | OCH₃ | N(OCH₃)(CH₃) | |
| H | CH₂CH₂F | H | OCH₃ | N(CH₃)₂ | |
| H | CHFCl | H | OCH₃ | OCH₃ | |
| H | CHFCl | H | CH₃ | OCH₃ | |
| H | CHFCl | H | CH₃ | CH₃ | |
| H | CHFCl | H | Cl | OCH₃ | |
| H | CHFCl | H | OCH₃ | CH₂OCH₃ | |
| H | CHFCl | H | CH₃ | OC₂H₅ | |
| H | CHFCl | H | CH₂Cl | OCH₃ | |
| H | CHFCl | H | F | OCH₃ | |
| H | CHFCl | H | OCH₃ | CH(OCH₃)₂ | |
| H | CHFCl | H | OCHF₂ | OCH₃ | |
| H | CHFCl | H | C₂H₅ | OCH₃ | |
| 5-F | CH₂F | H | CH₃ | OCH₃ | |

TABLE 42

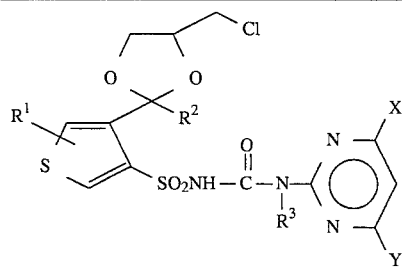

| R¹ | R² | R³ | X | Y | mp (°C.) |
|---|---|---|---|---|---|
| H | CH₂F | H | CH₃ | OCH₃ | |
| H | CH₂F | H | OCH₃ | OCH₃ | 168–171 |
| H | CH₂F | H | OC₂H₅ | Cl | 153–156 |
| H | CH₂F | H | OCH₃ | N(OCH₃)(CH₃) | |
| H | CH₂F | H | OCH₃ | N(CH₃)₂ | |
| H | CH₂F | H | CH₃ | CH₃ | 94–96 |
| H | CH₂Cl | H | OCH₃ | OCH₃ | |
| H | CH₂F | H | OC₂H₅ | NHCH₃ | |
| H | CH₂Cl | H | OCH₃ | N(OCH₃)(CH₃) | |
| H | CH₂Cl | H | OCH₃ | N(CH₃)₂ | |
| H | CH₂Br | H | CH₃ | OCH₃ | |
| H | CH₂Br | H | OCH₃ | OCH₃ | |
| H | CH₂Br | H | OC₂H₅ | NHCH₃ | |
| H | CH₂Br | H | OCH₃ | N(OCH₃)(CH₃) | |
| H | CH₂Br | H | OCH₃ | N(CH₃)₂ | |
| H | CHF₂ | H | CH₃ | OCH₃ | |
| H | CHF₂ | H | OCH₃ | OCH₃ | |
| H | CHF₂ | H | OC₂H₅ | NHCH₃ | |
| H | CHF₂ | H | OCH₃ | N(OCH₃)(CH₃) | |
| H | CHF₂ | H | OCH₃ | N(CH₃)₂ | |
| H | CH₂F | CH₃ | OCH₃ | OCH₃ | |
| H | CH₂Cl | CH₃ | OCH₃ | OCH₃ | |
| H | CH₂F | CH₃ | CH₃ | OCH₃ | |
| H | CH₂Br | CH₃ | OCH₃ | OCH₃ | |
| H | CH₂Cl | CH₃ | CH₃ | OCH₃ | |
| H | CH₂Br | CH₃ | CH₃ | OCH₃ | |
| H | CHF₂ | CH₃ | OCH₃ | OCH₃ | |
| H | CHF₂ | CH₃ | CH₃ | OCH₃ | |
| H | CH₂F | CH₃ | OC₂H₅ | NHCH₃ | |
| H | CH₂F | CH₃ | OCH₃ | N(CH₃)₂ | |
| H | CHFCH₃ | H | CH₃ | OCH₃ | |
| H | CHFCH₃ | H | OCH₃ | OCH₃ | |
| H | CHFCH₃ | H | OC₂H₅ | NHCH₃ | |
| H | CHFCH₃ | H | OCH₃ | N(OCH₃)(CH₃) | |
| H | CHFCH₃ | H | OCH₃ | N(CH₃)₂ | |
| H | CHClCH₃ | H | CH₃ | OCH₃ | |
| H | CHClCH₃ | H | OCH₃ | OCH₃ | |
| H | CHClCH₃ | H | OC₂H₅ | NHCH₃ | |
| H | CHClCH₃ | H | OCH₃ | N(OCH₃)(CH₃) | |
| H | CHClCH₃ | H | OCH₃ | N(CH₃)₂ | |
| H | CH₂CH₂F | H | CH₃ | OCH₃ | |
| H | CH₂CH₂F | H | OCH₃ | OCH₃ | |
| H | CH₂CH₂F | H | OC₂H₅ | NHCH₃ | |
| H | CH₂CH₂F | H | OCH₃ | N(OCH₃)(CH₃) | |
| H | CH₂CH₂F | H | OCH₃ | N(CH₃)₂ | |
| H | CHFCl | H | OCH₃ | OCH₃ | |
| H | CHFCl | H | CH₃ | OCH₃ | |
| H | CHFCl | H | CH₃ | CH₃ | |
| H | CHFCl | H | Cl | OCH₃ | |
| H | CHFCl | H | OCH₃ | CH₂OCH₃ | |
| H | CHFCl | H | CH₃ | OC₂H₅ | |
| H | CHFCl | H | CH₂Cl | OCH₃ | |
| H | CHFCl | H | F | OCH₃ | |
| H | CHFCl | H | OCH₃ | CH(OCH₃)₂ | |
| H | CHFCl | H | OCHF₂ | OCH₃ | |
| H | CHFCl | H | C₂H₅ | OCH₃ | |
| 5-F | CH₂F | H | CH₃ | OCH₃ | |

TABLE 43

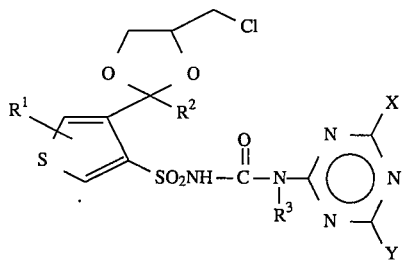

| R¹ | R² | R³ | X | Y | mp (°C.) |
|---|---|---|---|---|---|
| H | CH₂F | H | CH₃ | OCH₃ | 164–167 |
| H | CH₂F | H | OCH₃ | OCH₃ | 145–149 |
| H | CH₂F | H | OC₂H₅ | NHCH₃ | |
| H | CH₂F | H | OCH₃ | N(OCH₃)(CH₃) | |
| H | CH₂F | H | OCH₃ | N(CH₃)₂ | |
| H | CH₂Cl | H | CH₃ | OCH₃ | |
| H | CH₂Cl | H | OCH₃ | OCH₃ | |
| H | CH₂Cl | H | OC₂H₅ | NHCH₃ | |
| H | CH₂Cl | H | OCH₃ | N(OCH₃)(CH₃) | |
| H | CH₂Cl | H | OCH₃ | N(CH₃)₂ | |
| H | CH₂Br | H | CH₃ | OCH₃ | |
| H | CH₂Br | H | OCH₃ | OCH₃ | |
| H | CH₂Br | H | OC₂H₅ | NHCH₃ | |
| H | CH₂Br | H | OCH₃ | N(OCH₃)(CH₃) | |
| H | CH₂Br | H | OCH₃ | N(CH₃)₂ | |
| H | CHF₂ | H | CH₃ | OCH₃ | |
| H | CHF₂ | H | OCH₃ | OCH₃ | |
| H | CHF₂ | H | OC₂H₅ | NHCH₃ | |
| H | CHF₂ | H | OCH₃ | N(OCH₃)(CH₃) | |
| H | CHF₂ | H | OCH₃ | N(CH₃)₂ | |
| H | CHF₂ | CH₃ | OCH₃ | OCH₃ | |
| H | CH₂Cl | CH₃ | OCH₃ | OCH₃ | |
| H | CH₂F | CH₃ | CH₃ | OCH₃ | |
| H | CH₂Br | CH₃ | OCH₃ | OCH₃ | |
| H | CH₂Cl | CH₃ | CH₃ | OCH₃ | |
| H | CH₂Br | CH₃ | CH₃ | OCH₃ | |
| H | CHF₂ | CH₃ | OCH₃ | OCH₃ | |
| H | CHF₂ | CH₃ | CH₃ | OCH₃ | |
| H | CH₂F | CH₃ | OC₂H₅ | NHCH₃ | |
| H | CH₂F | CH₃ | OCH₃ | N(CH₃)₂ | |
| H | CHFCH₃ | H | CH₃ | OCH₃ | |
| H | CHFCH₃ | H | OCH₃ | OCH₃ | |
| H | CHFCH₃ | H | OC₂H₅ | NHCH₃ | |
| H | CHFCH₃ | H | OCH₃ | N(OCH₃)(CH₃) | |
| H | CHFCH₃ | H | OCH₃ | N(CH₃)₂ | |
| H | CHClCH₃ | H | CH₃ | OCH₃ | |
| H | CHClCH₃ | H | OCH₃ | OCH₃ | |
| H | CHClCH₃ | H | OC₂H₅ | NHCH₃ | |
| H | CHClCH₃ | H | OCH₃ | N(OCH₃)(CH₃) | |
| H | CHClCH₃ | H | OCH₃ | N(CH₃)₂ | |
| H | CH₂CH₂F | H | CH₃ | OCH₃ | |
| H | CH₂CH₂F | H | OCH₃ | OCH₃ | |
| H | CH₂CH₂F | H | OC₂H₅ | NHCH₃ | |
| H | CH₂CH₂F | H | OCH₃ | N(OCH₃)(CH₃) | |
| H | CH₂CH₂F | H | OCH₃ | N(CH₃)₂ | |
| H | CHFCl | H | OCH₃ | OCH₃ | |
| H | CHFCl | H | CH₃ | OCH₃ | |
| H | CHFCl | H | CH₃ | CH₃ | |
| H | CHFCl | H | Cl | OCH₃ | |
| H | CHFCl | H | OCH₃ | CH₂OCH₃ | |
| H | CHFCl | H | CH₃ | OC₂H₅ | |
| H | CHFCl | H | CH₂Cl | OCH₃ | |
| H | CHFCl | H | F | OCH₃ | |
| H | CHFCl | H | OCH₃ | CH(OCH₃)₂ | |
| H | CHFCl | H | OCHF₂ | OCH₃ | |
| H | CHFCl | H | C₂H₅ | OCH₃ | |
| 5-F | CH₂F | H | CH₃ | OCH₃ | |

TABLE 44

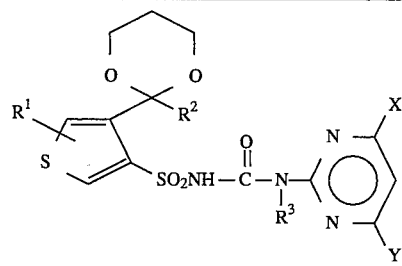

| R¹ | R² | R³ | X | Y | mp (°C.) |
|---|---|---|---|---|---|
| H | CH₂F | H | CH₃ | OCH₃ | 167–172 |
| H | CH₂F | H | OCH₃ | OCH₃ | 150–158 |
| H | CH₂F | H | OC₂H₅ | NHCH₃ | |
| H | CH₂F | H | OCH₃ | N(OCH₃)(CH₃) | |
| H | CH₂F | H | OCH₃ | N(CH₃)₂ | |
| H | CH₂F | H | CH₃ | CH₃ | 182–184 |
| H | CH₂Cl | H | OCH₃ | OCH₃ | |
| H | CH₂Cl | H | OC₂H₅ | NHCH₃ | |
| H | CH₂Cl | H | OCH₃ | N(OCH₃)(CH₃) | |
| H | CH₂Cl | H | OCH₃ | N(CH₃)₂ | |
| H | CH₂Br | H | CH₃ | OCH₃ | |
| H | CH₂Br | H | OCH₃ | OCH₃ | |
| H | CH₂Br | H | OC₂H₅ | NHCH₃ | |
| H | CH₂Br | H | OCH₃ | N(OCH₃)(CH₃) | |
| H | CH₂Br | H | OCH₃ | N(CH₃)₂ | |
| H | CHF₂ | H | CH₃ | OCH₃ | |
| H | CHF₂ | H | OCH₃ | OCH₃ | |
| H | CHF₂ | H | OC₂H₅ | NHCH₃ | |
| H | CHF₂ | H | OCH₃ | N(OCH₃)(CH₃) | |
| H | CHF₂ | H | OCH₃ | N(CH₃)₂ | |
| H | CH₂F | CH₃ | OCH₃ | OCH₃ | |
| H | CH₂Cl | CH₃ | OCH₃ | OCH₃ | |
| H | CH₂F | CH₃ | CH₃ | OCH₃ | |
| H | CH₂Br | CH₃ | OCH₃ | OCH₃ | |
| H | CH₂Cl | CH₃ | CH₃ | OCH₃ | |
| H | CH₂Br | CH₃ | CH₃ | OCH₃ | |
| H | CHF₂ | CH₃ | OCH₃ | OCH₃ | |
| H | CHF₂ | CH₃ | CH₃ | OCH₃ | |
| H | CH₂F | CH₃ | OC₂H₅ | NHCH₃ | |
| H | CH₂F | CH₃ | OCH₃ | N(CH₃)₂ | |
| H | CHFCH₃ | H | CH₃ | OCH₃ | |
| H | CHFCH₃ | H | OCH₃ | OCH₃ | |
| H | CHFCH₃ | H | OC₂H₅ | NHCH₃ | |
| H | CHFCH₃ | H | OCH₃ | N(OCH₃)(CH₃) | |
| H | CHFCH₃ | H | OCH₃ | N(CH₃)₂ | |
| H | CHClCH₃ | H | CH₃ | OCH₃ | |
| H | CHClCH₃ | H | OCH₃ | OCH₃ | |
| H | CHClCH₃ | H | OC₂H₅ | NHCH₃ | |
| H | CHClCH₃ | H | OCH₃ | N(OCH₃)(CH₃) | |
| H | CHClCH₃ | H | OCH₃ | N(CH₃)₂ | |
| H | CH₂CH₂F | H | CH₃ | OCH₃ | |
| H | CH₂CH₂F | H | OCH₃ | OCH₃ | |
| H | CH₂CH₂F | H | OC₂H₅ | NHCH₃ | |
| H | CH₂CH₂F | H | OCH₃ | N(OCH₃)(CH₃) | |
| H | CH₂CH₂F | H | OCH₃ | N(CH₃)₂ | |
| H | CHFCl | H | OCH₃ | OCH₃ | |
| H | CHFCl | H | CH₃ | OCH₃ | |
| H | CHFCl | H | CH₃ | CH₃ | |
| H | CH₂F | H | Cl | OCH₃ | 181–183 |
| H | CHFCl | H | OCH₃ | CH₂OCH₃ | |
| H | CHFCl | H | CH₃ | OC₂H₅ | |
| H | CHFCl | H | CH₂Cl | OCH₃ | |
| H | CHFCl | H | F | OCH₃ | |
| H | CHFCl | H | OCH₃ | CH(OCH₃)₂ | |
| H | CHFCl | H | OCHF₂ | OCH₃ | |
| H | CHFCl | H | C₂H₅ | OCH₃ | |
| 5-F | CH₂F | H | CH₃ | OCH₃ | |

TABLE 45

[Structure: Chemical structure showing R¹ and R² substituents on a ring with S, connected via SO₂NH—C(=O)—N(R³)— to a pyrimidine ring with X and Y substituents]

| R¹  | R²        | R³  | X      | Y              | mp (°C.) |
|-----|-----------|-----|--------|----------------|----------|
| H   | CH₂F      | H   | CH₃    | OCH₃           | 88–90    |
| H   | CH₂F      | H   | OCH₃   | OCH₃           | 93–95    |
| H   | CH₂F      | H   | OC₂H₅  | NHCH₃          |          |
| H   | CH₂F      | H   | OCH₃   | N(OCH₃)(CH₃)   |          |
| H   | CH₂F      | H   | OCH₃   | N(CH₃)₂        |          |
| H   | CH₂Cl     | H   | CH₃    | OCH₃           |          |
| H   | CH₂Cl     | H   | OCH₃   | OCH₃           |          |
| H   | CH₂Cl     | H   | OC₂H₅  | NHCH₃          |          |
| H   | CH₂Cl     | H   | OCH₃   | N(OCH₃)(CH₃)   |          |
| H   | CH₂Cl     | H   | OCH₃   | N(CH₃)₂        |          |
| H   | CH₂Br     | H   | CH₃    | OCH₃           |          |
| H   | CH₂Br     | H   | OCH₃   | OCH₃           |          |
| H   | CH₂Br     | H   | OC₂H₅  | NHCH₃          |          |
| H   | CH₂Br     | H   | OCH₃   | N(OCH₃)(CH₃)   |          |
| H   | CH₂Br     | H   | OCH₃   | N(CH₃)₂        |          |
| H   | CHF₂      | H   | CH₃    | OCH₃           |          |
| H   | CHF₂      | H   | OCH₃   | OCH₃           |          |
| H   | CHF₂      | H   | OC₂H₅  | NHCH₃          |          |
| H   | CHF₂      | H   | OCH₃   | N(OCH₃)(CH₃)   |          |
| H   | CHF₂      | H   | OCH₃   | N(CH₃)₂        |          |
| H   | CH₂F      | CH₃ | OCH₃   | OCH₃           |          |
| H   | CH₂Cl     | CH₃ | OCH₃   | OCH₃           |          |
| H   | CH₂F      | CH₃ | CH₃    | OCH₃           |          |
| H   | CH₂Br     | CH₃ | OCH₃   | OCH₃           |          |
| H   | CH₂Cl     | CH₃ | CH₃    | OCH₃           |          |
| H   | CH₂Br     | CH₃ | CH₃    | OCH₃           |          |
| H   | CHF₂      | CH₃ | OCH₃   | OCH₃           |          |
| H   | CHF₂      | CH₃ | CH₃    | OCH₃           |          |
| H   | CH₂F      | CH₃ | OC₂H₅  | NHCH₃          |          |
| H   | CH₂F      | CH₃ | OCH₃   | N(CH₃)₂        |          |
| H   | CHFCH₃    | H   | CH₃    | OCH₃           |          |
| H   | CHFCH₃    | H   | OCH₃   | OCH₃           |          |
| H   | CHFCH₃    | H   | OC₂H₅  | NHCH₃          |          |
| H   | CHFCH₃    | H   | OCH₃   | N(OCH₃)(CH₃)   |          |
| H   | CHFCH₃    | H   | OCH₃   | N(CH₃)₂        |          |
| H   | CHClCH₃   | H   | CH₃    | OCH₃           |          |
| H   | CHClCH₃   | H   | OCH₃   | OCH₃           |          |
| H   | CHClCH₃   | H   | OC₂H₅  | NHCH₃          |          |
| H   | CHClCH₃   | H   | OCH₃   | N(OCH₃)(CH₃)   |          |
| H   | CHClCH₃   | H   | OCH₃   | N(CH₃)₂        |          |
| H   | CH₂CH₂F   | H   | CH₃    | OCH₃           |          |
| H   | CH₂CH₂F   | H   | OCH₃   | OCH₃           |          |
| H   | CH₂CH₂F   | H   | OC₂H₅  | NHCH₃          |          |
| H   | CH₂CH₂F   | H   | OCH₃   | N(OCH₃)(CH₃)   |          |
| H   | CH₂CH₂F   | H   | OCH₃   | N(CH₃)₂        |          |
| H   | CHFCl     | H   | OCH₃   | OCH₃           |          |
| H   | CHFCl     | H   | CH₃    | OCH₃           |          |
| H   | CHFCl     | H   | CH₃    | CH₃            |          |
| H   | CHFCl     | H   | Cl     | OCH₃           |          |
| H   | CHFCl     | H   | OCH₃   | CH₂OCH₃        |          |
| H   | CHFCl     | H   | CH₃    | OC₂H₅          |          |
| H   | CHFCl     | H   | CH₂Cl  | OCH₃           |          |
| H   | CHFCl     | H   | F      | OCH₃           |          |
| H   | CHFCl     | H   | OCH₃   | CH(OCH₃)₂      |          |
| H   | CHFCl     | H   | OCHF₂  | OCH₃           |          |
| H   | CHFCl     | H   | C₂H₅   | OCH₃           |          |
| 5-F | CH₂F      | H   | CH₂    | OCH₃           |          |

Test results indicate that the compounds of the present invention are highly active pre-emergent or post-emergent herbicides or plant growth regulants. Many of them have utility for broad-spectrum pre- and/or post-emergency weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as wheat and barley. Alternatively, the subject compounds are useful to modify plant growth.

The rates of application for the compounds of the present invention are determined by a number of factors, including their use as plant growth modifiers or as herbicides, the crop species involved, the types of weeds to be controlled, weather and climate, formulations selected, mode of application, amount of foliage present, etc.

In general tens, the subject compounds should be applied at levels of around 0.05 to 10 kg/ha, the lower rates being suggested for use on lighter soils and/or those having a low organic matter content, for plant growth modifications or for situations where only short-term persistence is required.

Formulations

Useful formulations of the compounds of formula(I) can be prepared in conventional ways. They include dusts, granules, pellets, solutions, suspensions, emulsions, wettable powders, emulsifiable concentrates and the like. Many of these may be applied directly.

Sprayable formulations can be extented in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (1) about 0.1% to 20% surfactant(s) and (2) about 1% to 99.9% solid or liquid inert diluent(s). More specially, they will contain these ingredients in the following approximate proportions:

|                                                                           | Weight Percent*      |            |               |
|---------------------------------------------------------------------------|----------------------|------------|---------------|
| Formulations                                                              | Active Ingredient    | Diluent(s) | Surfactant(s) |
| Wettable Powders                                                          | 20–90                | 0–74       | 1–10          |
| Oil Suspensions, Emulsions, Solutions (including Emulsifiable concentrates) | 3–50                 | 40–95      | 0–15          |
| Aqueous Suspension                                                        | 10–50                | 40–84      | 1–20          |
| Dusts                                                                     | 1–25                 | 70–99      | 0–5           |
| Granules and Pellets                                                      | 0.1–95               | 5–99.9     | 0–15          |
| High Strength Compositions                                                | 90–99                | 0–10       | 0–2           |

*Active ingredient plus at least one of a surfactant or a diluent equals 100 weight percent.

Lower or higher levels of active ingredient can, of course, be present depending on the intended use and the physical properties of the compound. Higher ratios of surfactants to activate ingredient are sometimes desirable, and are achieved by incorporation into the formation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts.

Typical liquid diluents and solvents are described in Marsden, "Solvent Guide", 2nd Ed., Interscience, New York, 1950. Solubility under 0.1% is preferred for suspension concentrates; Solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses.

All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Patent No. 3,060,084). Granules and pellets may be made by spraying the active material upon preformed granular carriers or by agglomeration techniques.

See J. E. Browning, "Agglomeration", Chemical Engineering, Dec. 4, 1967, pp, 147ff. and "Perry's chemical Engineer's Handbook", 5th Ed., McGraw-Hill, New York, 1973, pp. 8–57ff.

For further information regarding the an of formulation, see for example:

H. M. Loux, U.S. Pat. No. 3,235,361, Feb. 15, 1966, Col. 6, line 16 through Col. 7, line 19 and Examples 10 through 41; R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182; H. Gysin and E. Knusli, U.S. Pat. No. 2,891,855, June 23, 1959, Col. 3, line 66 through Col. 5, line 17 and Examples 1–4; G. C. Klingman, "Weed Control as a Science", John Wiley and S. A. Evans, "Weed control Handbook", 5th Ed., Blackwell Scientific Publications, Oxford, 1968, pp. 101–103.

The compounds of the present invention can be used independently and may be used in combination with any other commercial herbicide. A summary of the possible combination herbicides is given below

| Common Name | | |
|---|---|---|
| acetochlor | acifluorfen | AC 252,214 |
| AC 263,499 | acrolein | alachlor |
| ametryn | amitrole | AMS |
| asulam | assure | atrazine |
| BAS-514 | barban | benefin |
| bensulfuron methyl | bensulide | bentazon |
| benzofluor | benzoylprop | bifenox |
| bromacil | bromoxynil | butachlor |
| buthidazole | butralin | butylate |
| cacodylic acid | CDAA | CDEC |
| CGA 82725 | CH-83 | chloramben |
| chlorbromuron | chlorimuron ethyl | chloroxuron |
| chlorpropham | chlorsulfuron | chlortoluron |
| cinmethylin | clethodim | clomazone |
| cloproxydim | clopyralid | CMA |
| cyanzine | cycloate | cycluron |
| cyperquat | cyprazine | cyprazole |
| cypromid | dalapon | dazomet |
| DCPA | desmediphan | desmetryn |
| diallate | dicamba | dichlorbenil |
| dichlorprop | dichlofop | diethatyl |
| difenzoquat | dinitramine | dinoseb |
| diphenamid | dipropetryn | diquat |
| diuron | DNOC | DOWCO453ME |
| DPX-M6316 | DSMA | endothall |
| EPTC | ethalfluralin | ethoxfumesate |
| Express | fenac | fenoxaprop ethyl |
| fenuron | fenuron TCA | flamprop |

-continued

| Common Name | | |
|---|---|---|
| fluazifop | fluazifop-butyl | fluazifop-P |
| fluchloralin | fluometuron | fluorochloridone |
| fluorodifen | fluoroglycofen | fluridone |
| fomesafen | fosamine | glyphosate |
| haloxyfop | harmoney | hexaflurate |
| hexazinone | HW-52 | imazamethabenz |
| imazapyr | imazaquin | imazethapyr |
| ioxynil | isopropalin | isoproturon |
| isouron | isoxaben | karbutilate |
| lactofen | lenacil | linuron |
| MAA | MAMA | MCPA |
| MCPB | mecoprop | mefluidide |
| methalpropalin | methabenzthiazuron | metham |
| methazole | methoxuron | metolachlor |
| metribuzin | metsulfuron methyl | MH |
| molinate | monolinuron | monuron |
| monuron TCA | MSMA | My-93 |
| napropamide | naproanilide | naptalam |
| neburon | nitralin | nitrofen |
| nitrofluorfen | norea | norfluazon |
| NTN-801 | oryzalin | oxadiazon |
| oxyfluorfen | paraquat | pebulate |
| pendimethalin | perfluidone | phenmedipham |
| picloram | PPG-1013 | pretilachlor |
| procyazine | profluralin | prometon |
| prometryn | pronamide | propachlor |
| propanil | propazine | propham |
| prosulfalin | prynachlor | pyrazon |
| pyrazolate | quizalofop ethyl | quizalofop |
| SC-2957 | secbumeton | sethoxydim |
| siduron | simazine | SL-49 |
| sulfometuron methyl | TCA | tebuthiuron |
| terbacil | terbuchlor | terbuthylazine |
| terbutol | terbutryn | thiameturon methyl |
| thiobencarb | triallate | triclopyr |
| tridiphane | trifluralin | trimeturon |
| 2,4-D | 2,4-DB | vernolate |
| X-52 | xylachlor | |

EXAMPLE 1

3-Bromo-4-fluoroacetylthiophene 3,4-Dibromothiophene(10 g, 0.041 mol)was dissolved in anhydrous ether and the solution was cooled to −78° C. under nitrogen atmosphere, and herein 17 ml of 2.5N n-butyl lithium was added dropwise.

The solution stirred for 10 min at −78° C. was cooled to −100° C., and herein ethyl fluoroacetate(4.8 ml, 0.05 mol) was added dropwise.

After stirring for 40 min, an excess of saturated solution of ammonium chloride was added and stirred.

The temperature of the reaction mixture was raised to room temperature, and herein an excess of ether was added to separate organic layer.

The organic layer was dried with magnesium sulfate, filtered and concentrated, and then the obtained residue was chromatographed through silica gel using 2:1 solution of methylene chloride/hexane to afford 6 g of the desired product. (white solid, yield:65%)

m.p.: 76°~77° C.

$^1$H NMR (CDCl$_3$) δ 5.40(d, 2H, J=48 Hz), 7.42(d, 1H, J=4 Hz), 8.37(d, 1H, J=4 Hz)

EXAMPLE 2

3-Bromo-4-(2-fluoromethyl-1,3-dioxalan-2-yl)thiophene

3-Bromo-4-fluoracetylthiolphene(10 g, 0.045 mol) was added in ethylene glycol, and herein trimethyl silyl chloride (22.7 ml, 0.18 mol) was added under stirring.

After stirring for 12 hr, the solution was poured in an excess of saturated solution of sodium bicarbonate and stirred, and then an excess of ether was added and shaked to separate ether layer.

The ether layer was dried with magnesium sulfate, filtered and concentrated to afford 10.4 g of the desired product. (light brown liquid, yield: 87%)

$^1$H NMR (CDCl$_3$) δ4.1 (m, 4H), 4.7 (d, 2H, J=48Hz), 7.4 (d, 1H, J=4 Hz), 7.6(d, 1H, J=4 Hz)

EXAMPLE 3

3-(2-Fluoromethyl-1,3-dioxalan-2-yl)-4-thiophene-sulfonamide

3-Bromo-4-(2-fluoromethyl- 1,3-dioxalan-2-yl)thiophene ( 19 g, 0.07 mol) was dissolved in anhydrous ether and the solution was cooled to −78° C. under nitrogen atmosphere, and herein n-butyl lithium (31 ml, 0.08 mol) was added dropwise.

After stirring for 10 min at −78° C., an excess of sulfur dioxide gas was added, and then the solution was stirred for 30 min at −78° C. The temperature of the reaction mixture was raised to room temperature, and the solution was filtered.

The obtained white solid was washed with ether, dried and dissolved in solution mixed 40 ml of water with 40 ml of isopropyl alcohol, and then the solution was cooled to 0° C.

After adding portion wise N-chlorosuccinimide (11.4 g, 0.085 mol), the solution was stirred for 2 hr at room temperature, and filtered to obtain a white solid.

The white solid was washed with water and dissolved in ethylacetate solution, and herein an excess of aqueous ammonia was added.

After stirring for 1 hr, the reacting solution was concentrated, and then the obtained solid was washed with a small quantity of ether to afford 13 g of the desired product (light yellow solid, yield: 68%).

m.p.: 126°~30° C.

$^1$H NMR (CDCl$_3$+DMSO-d$_6$) δ 4.2(m, 4H), 4.86(d, 2H, J=48Hz), 6.6 (brs, 2H), 7.85(d, 2H, J=4 Hz), 8.3(d, 2H, J=4 Hz)

IR(KBr): ν 3350, 3250 cm$^{-1}$

EXAMPLE 4

3-(2-Fluoromethyl-1,3-dioxalan-2-yl)-N-[(4-methoxy-6-methyltriazin- 2-yl)aminocarbonyl]-4-thiophenesulfonamide 3-(2-fluoromethyl- 1,3-dioxalan-2-yl)-4-thiophene-sulfonamide (1 g, 0.0037 mol) was dissolved in 20 ml of acetonitrile and phenyl (4-methoxy-6-methyltriazin- 2-yl) carbamate (0.86 g, 0.0037 mol) was added at room temperature, and herein 0.8 ml of DBU was added dropwise.

After stirring for 1 hr, the reacting solution was diluted with 100 ml of methylene chloride, and was washed with hydrochloric acid solution.

The organic layer was dried with magnesium sulfate, filtered and concentrated. The obtained solid was washed with a small quantity of ether to afford 1.3 g of the desired product (yield: 84%).

m.p. :212°~214° C.

$^1$H NMR (DMSO-d$_6$) δ 2.51(s, 3H), 3.7–4.1(m, 4H), 4.05(s, 3H), 4.7(d, 2H, J=48Hz), 7.8(d, 2H, J=4 Hz), 8.5(d, 2H, J=4 Hz), 11.1(brs, 1H), 12.5(brs, 1H)

IR(KBr): ν (C=O) 1720 cm$^{-1}$

EXAMPLE 5

3-Bromo-2-fluoroacetylthiophene 2,3-dibromothiophene (10 g, 0.041 mol) was dissolved in anhydrous ether and cooled to −78° C. under nitrogen atmosphere, and herein 17 ml of 2.5N n-butyl lithium was added dropwise.

After stirring for 10 min at −78° C., the temperature of the reacting solution was cooled to −100° C., and herein ethylfluoro acetate(4.8 ml, 0.5 mol) was added dropwise.

After stirring for 40 min, an excess of saturated solution of ammonium chloride was added and stirred, and after raising the temperature to room temperature, an excess of ether was added to separate organic layer.

The obtained organic layer was dried with magnesium sulfate, filtered and concentrated. The residue was chromatographed through silica gel using 2:1 solution of methylene chloride and hexane to afford 6 g of the desired product (white solid, yield: 65%).

$^1$H NMR (CDCl$_3$) δ 5.6(d, 2H, J=48 Hz), 7.25(d, 1H, J=5Hz), 7.75 (d, 1H, J=5 Hz)

EXAMPLE 6

3-Bromo-2-(2-fluoromethyl-1,3-dioxalan-2-yl)thiophene

3-Bromo-2-fluoroacetylthiophene (10 g, 0.045 mol) was dissolved in ethylene glycol, anti trimethylsilyl chloride (22.7 ml, 0.18 mol) was added under stirring.

After stirring for 12 hr, the solution was poured in an excess of saturated solution of sodium bicarbonate and stirred, and herein an excess of ether was added and stirred to separate ether layer.

The obtained ether layer was dried with magnesium sulfate, filtered and concentrated to afford 11 g of the desired product (light brown liquid, yield: 92%).

$^1$H NMR (CDCl$_3$) δ4.1(m, 4H), 4.7(d, 2H, J=48 Hz), 6.95 (d, 1H, J=5 Hz), 7.2(d, 1H, J=5 Hz)

EXAMPLE 7

2-(2-Fluoromethyl-1,3-dioxalan-2-yl)-3-thiophene-sulfonamide

3-Bromo-2-(2-fluoromethyl-1,3-dioxalan-2-yl)thiophene (19 g, 0.07 mol) was dissolved in anhydrous ether anti the solution was cooled to −78° C., and herein n-butyl lithium (31 ml, 0.08 mol) was added dropwise under nitrogen atmosphere.

After stirring for 10 min at −78° C., an excess of sulfur dioxide gas was added, and after stirring 30 min at −78° C., the temperature of the reacting solution to filter the solid material.

The solid was dried and dissolved in solution mixed 40 ml of water with 40 ml of isopropyl alcohol, and after cooling to 0° C., herein N-chlorosuccinimide (11.4 g, 0.085 mol) was added portionwise.

After stirring for 2 hr at room temperature and filtering, the obtained solid was washed with water and dissolved in ethyl acetate solution, and herein an excess of aqueous ammonia was added while stirring for 1 hr at room temperature.

The reacted solution was concentrated, and then the obtained solid was washed with a small quantity of ether to afford 14 g of the desired product (yield: 74%).

m.p.: 120°~121° C.

$^1$H NMR (CDCl$_3$+DMSO-d$_6$) δ 4.1(m, 4H), 4.75(d, 2H, J=48 Hz), 6.7 (brs, 2H), 7.4(s, 2H)

IR(KBr): ν (NH$_2$) 3380, 3270 cm$^{-1}$

EXAMPLE 8

2-(2-Fluoro-methyl-1,3-dioxalan-2-yl)-N-[(4-methoxy-6-methyltriazin- 2-yl) aminocarbonyl]-3-thiophenesulfonamide 2-(2-fluoromethyl-1,3-dioxalan-2-yl)-3-thiophenesulfonamide (1 g, 0.0037 mol) was dissolved in 20 ml of acetonitrile and phenyl(4-methoxy-6-methyltriazin-2-yl) carbamate (0.86 g, 0.0037 mol) was added at room temperature, and herein 0.80 ml of DBU was added dropwise.

After stirring for 1hr, the solution was diluted with 100 ml of methylene chloride, and was washed with 5% hydrochloric acid solution.

The separated organic layer was dried with magnesium sulfate, filtered and concentrated, and then the obtained solid was washed with hexane or a small quantity of ether to afford 1.34 g of the desired product (yield: 87%).

m.p.: 186°~189° C.

$^1$H NMR (DMSO-d$_6$) δ 2.55(s, 3H), 4.0(m, 4H), 4.85 (d, 2H, J=48 Hz), 7.6(q, 2H), 10.9(brs, 1H)

IR(KBr): ν (C=O) 1700 cm$^{-1}$

EXAMPLE 9

3-Fluoroacetylthiophene

3-Bromothiophene(10 g, 0.061 mol) was dissolved in anhydrous ether and the solution was cooled to −78° C. under nitrogen atmosphere, and herein 27 ml of 2.5N n-butyl lithium was added dropwise.

After stirring for 10 min at −78° C., the temperature of the solution was cooled to 100° C., and herein ethylfluoroacetate (7.1 ml, 0.074 mol) was added dropwise.

The solution was stirred for 40 min, and an excess of saturated solution of ammonium chloride was added.

After raising to room temperature, the reaction mixture was extracted with an excess of ether.

The obtained residue was dried with magnesium sulfate, filtered and concentrated, and then chromatographed through silica gel using 2:1 solution of methylenechloride/hexane to afford 6.4 g of the desired product (yield: 72%).

$^1$H NMR (CDCl$_3$) δ 5.48(d, 2H, J=48 Hz), 7.35~8.4 (m, 3H)

EXAMPLE 10

3-(2-Fluoromethyl- 1,3-dioxalan-2-yl)thiophene

3-Fluoroacetylthiophene (10 g, 0.069 mol) was dissolved in ethylene glycol, and herein trimethylsilyl chloride (35 ml, 0.275 mol) was added under stirring.

After stirring for 12 hr, the solution is poured in saturated solution of sodium bicarbonate and stirred.

The reaction mixture was extracted with an excess of ether, and then the obtained residue was dried with magnesium sulfate, filtered and concentrated to afford 11 g of the desired product(yield: 85%).

$^1$H NMR (CDCl$_3$) δ 4.0(m, 4H), 4.44(d, 2H, J=48 Hz), 7.0–7.5 (m, 3H)

EXAMPLE 11

3-(2-Fluoromethyl-1,3-dioxalan-2-yl)-2-thiophenesulfonamide 3-(2-Fluoromethyl-1,3-dioxalan-2-yl)thiophene(5 g, 0.026 mol) was dissolved in anhydrous ether, and herein 12 ml of n-butyl lithium was added dropwise under nitrogen atmosphere.

After stirring for 1 hr at room temperature, the temperature of the solution was raised in order to reflux for 30 min, and the solution was cooled to −78° C. and sulfur dioxide gas was added.

The reacting solution was stirred for 30 min at −78° C., and the temperature was raised to room temperature. The obtained solid was filtered, dried and dissolved ill solution mixed 20 ml of water with 20 ml of isopropyl alcohol, and after cooling to 0° C., N-chlorosuccinimide (3.9 g, 0.029 mol) was added portionwise.

After stirring for 2 hr at room temperature, the obtained solid was filtered, washed with water and was dissolved in ethyl acetate, and herein an excess of aqueous ammonia was added.

After stirring for 1hr at room temperature, the reaction mixture was concentrated, and then the obtained solid was washed with a small quantity of ether to afford 2 g of the desired product (yield: 92%).

$^1$H NMR (CDCl$_3$+DMSO-d$_6$)δ 4.1(m, 4H), 4.65(d, 2H, J=48 Hz), 6.7 (brs, 2H), 7.1 (d, 1H, J=5 Hz), 7.4(d, 1H, J=5 Hz)

EXAMPLE 12

3-(2-Fluoromethyl- 1,3-dioxalan-2-yl)-N-[(4-methoxy-6-methyltriazin-2- yl)aminocarbonyl]-2-thiophenesulfonamide 3-(2-Fluoromethyl-1,3-dioxalan-2-yl)-2-thiophenesulfonamide (1 g, 0.0037 mol) was dissolved in 20 ml of acetonitrile and phenyl(4-methoxy-6-methyltriazin- 2-yl)-carbamate (0.86 g, 0.0037 mol) was added at room temperature, and herein 0.8 ml of DBU was added dropwise.

After stirring for 1 hr, the solution was diluted with methylene chloride, and was washed with 5% hydrochloric acid solution. The separated organic layer was dried with magnesium sulfate filtered and concentrated, and then the obtained solid was washed with hexane and ether to afford 1.3 g of the desired product (yield: 84%).

mp.: 167°~170° C.

$^1$H NMR (DMSO-d$_6$) δ 2.55(s, 3H), 4.0(m, 4H), 4.7(d,

2H, J=48 Hz), 7.3(d, 1H, J=5 Hz), 7.8(d, 1H, J=5 Hz), 10.9(brs, 1H)

IR(KBr): ν (C=O) 1700 cm$^{-1}$

EXAMPLE 13

4-(1,1-Diethoxy-2-fluoroethyl)-N-[(4-methoxy-6-methyl- pyrimidin-2-yl)aminocarbonyl-3-thiophenesulfonamide 4-(1,1-Diethoxy-2-fluoroethyl)-3-thiophenesulfonamide (1 g, 0.0034 mol) was dissolved in 20 ml of acetonitrile, and phenyl(4-methoxy-6-methylpyrimidin-2-yl) carbamate(0.87 g, 0.0034 mol) was added at room temperature, and herein 0.8 ml of DBU was added dropwise.

After stirring for 1 hr, the solution was diluted with 100 ml of methylene chloride, and washed with 5% hydrochloric acid solution. The residue was dried with magnesium sulfate, filtered and concentrated, and then the obtained solid was washed with hexane and ether to afford 1.2 g of the desired product.

m.p.: 145°~148° C.

IR(KBr): ν (C=O) 1710cm$^{-1}$

EXAMPLE 14

3-(2-Fluoromethyl-1,3-dioxalan-2-yl)-N-[(4-methoxy-6-methylpyrimidin-2-yl)aminocarbonyl]-4-thiophenesulfonamide 3-(2-Fluoromethyl-1,3-dioxalan-2-yl)-4-thiophenesulfonamide (1 g, 0.0037 mol) was dissolved in 20 ml of acetonitrile and phenyl (4-methoxy-6- methylpyrimidin-2-yl)carbamate (0.86 g, 0.0037 mol) was added at room temperature, and herein 0.8 ml of DBU was added dropwise.

After stirring for 1 hr, the solution was diluted with 100 ml of methylene chloride, and was washed with 5% hydrochloric acid solution. The separated organic layer was dried with magnesium sulfite, filtered and concentrated, and then the obtained solid was washed with hexane and ether to afford 1.3 g of the desired product (yield: 84%).

m.p.: 185°~189° C.

IR(KBr): ν (C=O) 1709 cm$^{-1}$

EXAMPLE 15

Wettable Powder

| | |
|---|---|
| 3-(2-Fluoromethyl-1,3-dioxalan-2-yl)-N-[(4-methoxy-6-methyltriazin-2-yl)aminocarbonyl]-4-thiophenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 16

Wettable Powder

| | |
|---|---|
| 3-(2-Fluoromethyl-1,3-dioxalan-2-yl)-N-[(4-methoxy-6-methyltriazin-2-yl)aminocarbonyl]-4-thiophenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 17

Granule

| | |
|---|---|
| wettable powder of Example 16 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender.

The granules are dried and packaged.

EXAMPLE 18

Extruded Pellet

| | |
|---|---|
| 3-(2-Fluoromethyl-1,3-dioxalan-2-yl)-N-[(4-methoxy-6-methyltriazin-2-yl)aminocarbonyl]-4-thiophenesulfonamide | 25% |
| anhydrous sodium sulfate | 10% |
| crude calcium lignisulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. They may be used directly after drying, or the dried pellets may be crushed to pass a U.S.S. No. 20 sieve(0.84 mm openings). The granules held on a U.S.S. No. 40 sieve(0.42 mm openings) may be packaged for use and the fines recycled.

EXAMPLE 19

Oil Suspension

| | |
|---|---|
| 3-(2-Fluoromethyl-1,3-dioxalan-2-yl)-N-[(4-methoxy-6-methyltriazin-2-yl)aminocarbonyl]-4-thiophenesulfonamide | 25% |
| polyoxyethylene sorbitol hexaoleate | 5% |
| highly aliphatic hydrocarbon oil | 70% |

The ingredients are ground together in sand mill until the solid particles have been reduced to under about 5 microns. The resulting thick suspension may be applied directly, but preferably after being extended with oils or emulsified in water.

EXAMPLE 20

Wetting Powder

| | |
|---|---|
| 3-(2-Fluoromethyl-1,3-dioxalan-2-yl)-N-[(4-methoxy-6-methyltriazin-2-yl)aminocarbonyl]-4-thiophenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve(0.3 mm openings) and packaged.

EXAMPLE 21

Low Strength Granule

| | |
|---|---|
| 3-(2-Fluoromethyl-1,3-dioxalan-2-yl)-N-[(4-methoxy-6-methyltriazin-2-yl)aminocarbonyl]-4-thiophenesulfonamide | 1% |
| N,N-dimethylformamide | 9% |
| attapulgite granule (U.S.S. 20–40 sieve) | 90% |

The active ingredient is dissolved in the solvent and the solution is sprayed upon dedusted granules in a double cone blender.

After spraying of the solution has been completed, the blender is allowed to run for a short period and then the granules are packaged.

EXAMPLE 22

Aqueous Suspension

| | |
|---|---|
| 3-(2-Fluoromethyl-1,3-dioxalan-2-yl)-N-[(4-methoxy-6-methyltriazin-2-yl)aminocarbonyl]-4-thiophenesulfonamide | 40% |
| polyacrylic acid thickener | 0.3% |
| dodecylphenol polyethylen glycol ether | 0.5% |
| disodium phosphate | 1% |
| monosodium phosphate | 0.5% |
| polyvinyl alcohol | 1% |
| water | 56.7% |

The ingredients are blended and ground together in a sand mill to produce particles essentially all under 5 microns in size.

EXAMPLE 23

Solution

| | |
|---|---|
| ammonium salt of N-[(4,6-dimethoxytriazin-2-yl)aminocarbonyl]-3-(2-fluoromethyl-1,3-dioxalan-2-yl)-4-thiophensulfonamide | 5% |
| water | 95% |

The salt is added directly to the water with stirring to produce the solution, which may then be packaged for use.

EXAMPLE 24

Low Strength Granule

| | |
|---|---|
| 3-(2-Fluoromethyl-1,3-dioxalan-2-yl)-N-[(4-methoxy-6-methyltriazin-2-yl)aminocarbonyl]-4-thiophene-sulfonamide | 0.1% |
| attapulgite granules (U.S.S. No. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and packaged.

EXAMPLE 25

Wettable Powder

| | |
|---|---|
| 3-(2-Fluoromethyl-1,3-dioxalan-2-yl)-N-[(4-methoxy-6-methyltriazin-2-yl)aminocarbonyl]-4-thiophenesulfonamide | 40% |
| dioctyl sodium sulfosuccinate | 1.5% |
| sodium ligninsulfonate | 3% |
| low viscosity methyl cellulose | 1.5% |
| attapulgite | 54% |

The ingredient are throughly blended, passed through an air mill, to produce an average particle size under 15 microns, reblended, and sifted through a U.S.S. No. 50 sieve(0.3 mm opening) before packaging. All compounds of the invention may be formulated in the same manner.

EXAMPLE 26

Granule

| | |
|---|---|
| wettable powder of Example 25 | 15% |
| gypsum | 69% |
| potassium sulfate | 16% |

The ingredients are blended in rotating mixer and water sprayed on to accomplish granulation. When most of the material has reached the desired range of 1.0 to 0.42 cm (U.S.S. #18 to 40 sieves), the granules are removed, dried, and screened. Oversized material is crushed additional material in the desired range. These granules contain % active ingredient.

EXAMPLE 27

High Strength Concentrate

| | |
|---|---|
| 3-(2-Fluoromethyl-1,3-dioxalan-2-yl)-N-[(4-methoxy-6-methyltriazin-2-yl)aminocarbonyl]-4-thiophenesulfonamide | 99% |
| silica aerogel | 0.5% |
| synthetic amorphous silica | 0.5% |

The ingredient are blended and ground in a hammer-mill to produce a material essentially all passing a U.S.S. No. 50 screen (0.3 mm opening). The concentrate may be formulated further if necessary.

EXAMPLE 28

Wettable Powder

| | |
|---|---|
| 3-(2-Fluoromethyl-1,3-dioxalan-2-yl)-N-[(4-methoxy-6-methyltriazin-2-yl)aminocarbonyl]-4-thiophenesulfonamide | 90% |
| dioctyl sodium sulfosuccinate | 0.1% |
| synthetic fine silica | 9.9% |

The ingredient are blended and ground in a hammer-mill to produce particles essentially all below 100 microns. The material is sifted through a U.S.S. No. 50 screen and the packaged.

EXAMPLE 29

Wettable Powder

| | |
|---|---|
| 3-(2-Fluoromethyl-1,3-dioxalan-2-yl)-N-[(4-methoxy-6-methyltriazin-2-yl)aminocarbonyl]-4-thiophenesulfonamide | 40% |
| sodium ligninsulfonate | 20% |
| montmorillonite clay | 40% |

The ingredients are throughly blended, coarsely hammer-milled and then air-milled to produce particles essentially all below 10 microns in size. The material is reblended and the packaged.

EXAMPLE 30

Oil Suspension

| | |
|---|---|
| 3-(2-Fluoromethyl-1,3-dioxalan-2-yl)-N-[(4-methoxy-6-methyltriazin-2-yl)aminocarbonyl]-4-thiophenesulfonamide | 35% |
| blended of polyalcohol carboxylic ester and oil soluble petroleum sulfonate | 6% |
| xylene | 59% |

The ingredients are combined and ground together in a sand mill to produce particle essentially all below 5 microns. The product can be used directly, extended with oil, or emulsified in water.

EXAMPLE 31

Dust

| | |
|---|---|
| 3-(2-Fluoromethyl-1,3-dioxalan-2-yl)-N-[(4-methoxy-6-methyltriazin-2-yl)aminocarbonyl]-4-thiophenesulfonamide | 10% |
| attapulgite | 10% |
| pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 32

Emulsifiable Concentrate

| | |
|---|---|
| 3-(2-Fluoromethyl-1,3-dioxalan-2-yl)-N-[(4-methoxy-6-methyltriazin-2-yl)aminocarbonyl]-4-thiophenesulfonamide | 10% |
| chlorobenzene | 84% |
| sorbitan monostearate and polyoxyethylene condensates thereof | 6% |

The ingredients are combined and stirred to produce a solution which can be emulsified in water for application.

EXAMPLE 33

Pre-emergence test

To produce a suitable preparation of active compound, 1 pan by weight of active compound is mixed with 5 parts by weight of acetone, 1 pan by weight of alkylaryl polyglycol ether of emulsifier is added and the concentrate is diluted with water to the desired concentration Seeds of the test plants are shown in normal soil and, after 24 hours, watered with the preparation of the active compound.

It is expedient to keep constant the amount of water per unit area. The concentration of the active compound in the preparation is of no importance, only the amount of active compound applied per unit area being desicive.

After three weeks, the degree of damage to the plants is rated in % damage in comparison to the development of the untreated control.

The figures denote:

0%=no action (like untreated control)

20% =slight effect

70% =herbicidal effect

100% =total destruction.

In this test, the active compounds(I) according to the preparation Examples exhibit a better herbicidal activity against nomo- and dicotyledon weeds.

EXAMPLE 34

Post-emergence test

To produce a suitable preparation of active compound, 1 part by weight of active compound is mixed with 5 parts by weight of acetone, 1 part by weight of alkylaryl polyglycol ether of emulsifier is added and the concentrate is diluted with water to the desired concentration.

Test plants which have a height of 5~15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparasion to the development of the untreated control.

The figures denote:

0%=no action (like untreated control)

20%=slight effect

70%=herbicidal effect

100% =total destruction.

In this test, the active compounds(I) according to the preparation Examples exhibit a better herbicidal activity against mono- and dicotyledon weeds.

It is understood that the specification and examples are illustrative but not limitative of the present invention and that other embodiments within the spirit and scope of the invention will suggest themselves to those skilled in the art.

The herbicidal proficiency of the active ingredients of the present invention is evident from the test results which are recorded in following Tables.

The following Tables are represented pre- and post-emergence herbicidal evaluation of following "test compounds".

| Structure | X | Y | Z | Comp. No. |
|---|---|---|---|---|
| (structure 1: thiophene-SO₂NHCONH-pyrimidine with dioxolane-CH₂F group) | CH₃ | OEt | CH | 1 |
|  | OCH₃ | OCH₃ | CH | 2 |
|  | Cl | OEt | CH | 3 |
|  | CH₃ | OCH₃ | CH | 4 |
|  | CH₃ | CH₃ | CH | 5 |
|  | Cl | CH₃ | CH | 6 |
|  | CH₃ | OCH₃ | N | 7 |
|  | OCH₃ | OCH₃ | N | 8 |
| (structure 2: thiophene-SO₂NHCONH-pyrimidine with dioxolane-CH₂Cl group) | CH₃ | CH₃ | CH | 9 |
|  | CH₃ | OCH₃ | CH | 10 |
|  | CH₃ | OEt | CH | 11 |
|  | OCH₃ | OCH₃ | CH | 12 |
|  | Cl | OCH₃ | CH | 13 |
|  | Cl | OEt | CH | 14 |
|  | Cl | CH₃ | CH | 15 |
|  | CH₃ | OCH₃ | N | 16 |
|  | Cl | OCH₃ | N | 17 |
|  | Cl | OEt | N | 18 |
| (structure 3: thiophene with dioxolane-CH₂F, SO₂NHCONH-pyrimidine) | CH₃ | CH₃ | CH | 19 |
|  | Cl | OCH₃ | CH | 20 |
|  | Cl | OEt | CH | 21 |
|  | Cl | CH₃ | CH | 22 |
|  | CH₃ | OCH₃ | N | 23 |
|  | OCH₃ | OCH₃ | N | 24 |
| (structure 4: thiophene with dioxolane-CH₂F, SO₂NHCONH-pyrimidine) | CH₃ | CH₃ | CH | 25 |
|  | CH₃ | OCH₃ | CH | 26 |
|  | OCH₃ | OCH₃ | CH | 27 |
|  | Cl | OCH₃ | CH | 28 |
|  | CH₃ | OCH₃ | N | 29 |
|  | OCH₃ | OCH₃ | N | 30 |
| (structure 5: thiophene with dioxolane-CH₂Cl, SO₂NHCONH-pyrimidine) | CH₃ | OCH₃ | CH |  |
|  | CH₃ | OEt | CH |  |
|  | OCH₃ | OCH₃ | CH |  |
|  | Cl | OCH₃ | CH |  |
|  | Cl | OEt | CH |  |
|  | Cl | CH₃ | CH |  |
|  | CH₃ | OCH₃ | N |  |
|  | OCH₃ | OCH₃ | N |  |
|  | Cl | OCH₃ | N |  |

-continued

| Structure | X | Y | Z | Comp. No. |
|---|---|---|---|---|
| 31 | | | | |
| 32 | | | | |
| 33 | | | | |
| 34 | | | | |
| 35 | | | | |
| 36 | | | | |
| 37 | | | | |
| 38 | | | | |
| 39 | | | | |
| (structure with CF$_3$, dioxolane, thiophene, SO$_2$NHCONH-pyrimidine) | CH$_3$ | CH$_3$ | CH | 40 |
| | CH$_3$ | OCH$_3$ | CH | 41 |
| | OCH$_3$ | OCH$_3$ | CH | 42 |
| | CH$_3$ | OCH$_3$ | N | 43 |
| (structure with F, dioxane, thiophene, SO$_2$NHCONH-pyrimidine) | CH$_3$ | CH$_3$ | CH | 44 |
| | CH$_3$ | OCH$_3$ | CH | 45 |
| | OCH$_3$ | OCH$_3$ | CH | 46 |
| | Cl | OEt | CH | 47 |
| | CH$_3$ | OCH$_3$ | N | 48 |
| | OCH$_3$ | OCH$_3$ | N | 49 |
| (structure with F, branched dioxane, thiophene) | CH$_3$ | CH$_3$ | CH | 50 |
| | OCH$_3$ | OCH$_3$ | CH | 51 |
| | Cl | OCH$_3$ | CH | 52 |
| | Cl | OEt | CH | 53 |
| | CH$_3$ | OCH$_3$ | N | 54 |
| | OCH$_3$ | OCH$_3$ | N | 55 |
| (structure with Cl, F, dioxane, thiophene) | CH$_3$ | CH$_3$ | CH | 56 |
| | OCH$_3$ | OCH$_3$ | CH | 57 |
| | Cl | OCH$_3$ | CH | 58 |
| | CH$_3$ | OCH$_3$ | N | 59 |
| | OCH$_3$ | OCH$_3$ | N | 60 |
| (thiophene with F-dioxolane) | CH$_3$ | CH$_3$ | CH | 61 |
| | CH$_3$ | OCH$_3$ | CH | 62 |
| | CH$_3$ | OEt | CH | 63 |
| | OCH$_3$ | OCH$_3$ | CH | 64 |
| | CH$_3$ | OCH$_3$ | N | 65 |
| | OCH$_3$ | OCH$_3$ | N | 66 |
| (thiophene with Cl-dioxolane) | CH$_3$ | CH$_3$ | CH | 67 |
| | CH$_3$ | OCH$_3$ | CH | 68 |
| | CH$_3$ | OEt | CH | 69 |
| | Cl | OCH$_3$ | CH | 70 |
| | CH$_3$ | OCH$_3$ | N | 71 |
| | OCH$_3$ | OCH$_3$ | N | 72 |

-continued

| Structure | X | Y | Z | Comp. No. |
|---|---|---|---|---|
| Cl-CH2-C(O-)(O-)-[thiophene]-SO2NHCONH-C(=N-X)(N=Y)Z | CH3 | CH3 | CH | 73 |
| | CH3 | OCH3 | N | 74 |
| | OCH3 | OCH3 | N | 75 |
| F-CH2-C(O-)(O-)-[thiophene]-SO2NHCONH- | CH3 | CH3 | CH | 76 |
| | OCH3 | OCH3 | CH | 77 |
| | CH3 | OCH3 | N | 78 |
| | OCH3 | OCH3 | N | 79 |
| F-CH2-C(OEt)(OEt)-[thiophene]-SO2NHCONH- | CH3 | CH3 | CH | 80 |
| | CH3 | OCH3 | CH | 81 |
| | OCH3 | OCH3 | CH | 82 |
| | Cl | OCH3 | CH | 83 |
| | CH3 | OCH3 | N | 84 |
| | OCH3 | OCH3 | N | 85 |
| CF3-C(O-)(O-)-[thiophene]-SO2NHCONH- | CH3 | CH3 | CH | 86 |
| | CH3 | OCH3 | CH | 87 |
| | CH3 | OCH3 | N | 88 |
| | OCH3 | OCH3 | N | 89 |

PLANT RESPONSE SCREENING (Herbicide)

| Comp. No. | TYPE | kg/ha | SORBI | ECHOR | BROJA (SETVI) [AGRSM] | DIGSA | PANDI | SOLNI | AESIN | ABUTH | XANSI | CAGHE |
|---|---|---|---|---|---|---|---|---|---|---|---|---|
| 1 | PRE | .05 | 90 | 90 | 90 | 70 | 90 | 20 | 40 | 65 | 80 | 100 |
|  | POST | .05 | 70 | 90 | 100 | 20 | 0 | 0 | 60 | 25 | 70 | 100 |
| 2 | PRE | .05 | 100 | 100 | 100 | 90 | 100 | 20 | 40 | 50 | 90 | 100 |
|  | POST | .05 | 90 | 100 | 100 | 40 | 10 |  | 90 | 100 | 60 | 60 |
| 3 | PRE | .05 | 65 | 30 | 40 | 15 | 10 | 20 | 0 | 50 | 0 | 25 |
|  | POST | .05 | 10 | 20 | 30 | 20 | 0 | 0 | 0 | 0 | 0 | 0 |
| 20 | PRE | .1 | 100 | 100 | 100 | 60 | 65 | 90 | 40 | 90 | 90 | 100 |
|  | POST | .1 | 80 | 100 | 90 | 50 | 30 | 75 | 90 | 100 | 100 | 90 |
| 21 | PRE | .05 | 40 | 60 | 0 | 10 | 0 | 0 | 0 | 10 |  | 0 |
|  | POST | .05 | 50 | 60 | 30 | 0 | 0 | 0 | 0 | 0 | 0 | 0 |
| 22 | PRE | .05 | 15 | 0 | 0 | 30 | 0 | 20 | 10 | 10 | 60 | 0 |
|  | POST | .05 | 20 | 20 | 0 | 20 | 0 | 0 | 0 | 0 | 0 | 0 |
| 25 | PRE | .05 | 100 | 100 | 100 | 100 | 100 | 80 | 90 | 90 | 90 | 100 |
|  | POST | .05 | 100 | 100 | 100 | 100 | 90 | 80 | 90 | 100 | 100 | 100 |
| 26 | PRE | .05 | 100 | 100 | 100 | 100 | 100 | 60 | 100 | 90 | 100 | 100 |
|  | POST | .05 | 100 | 100 | 100 | 100 | 90 | 50 | 90 | 100 | 100 | 100 |
| 27 | PRE | .05 | 100 | 100 | 100 | 100 | 100 | 60 | 80 | 90 | 90 | 60 |
|  | POST | .05 | 90 | 100 | 80 | 100 | 100 | 50 | 100 | 100 | 100 | 100 |
| 28 | PRE | .05 | 90 | 100 | 80 | 90 | 100 | 90 | 60 | 40 | 80 | 30 |
|  | POST | .05 | 30 | 100 | 100 | 70 |  | 80 | 90 | 70 | 100 | 100 |
| 29 | PRE | .05 | 100 | 100 | 90 | 100 | 90 | 60 | 100 | 100 | 90 | 100 |
|  | POST | .05 | 100 | 100 | 100 | 100 | 90 | 60 | 100 | 100 | 100 | 100 |
| 30 | PRE | .05 | 90 | 100 | 80 | 100 | 90 | 50 | 100 | 100 | 95 | 100 |
|  | POST | .05 | 100 | 100 | 100 | 100 | 60 | 70 | 100 | 100 | 100 | 100 |
| 40 | PRE | .05 | 60 | 40 | 60 | 50 | 70 | 0 | 0 | 0 | 0 | 20 |
|  | POST | .05 | 50 | 30 | 80 | 10 |  | 40 | 0 | 0 | 40 | 0 |

-continued

PLANT RESPONSE SCREENING (Herbicide)

| Comp. No. | TYPE | kg/ha | SORBI | ECHOR | BROJA (SETVI) [AGRSM] | DIGSA | PANDI | SOLNI | AESIN | ABUTH | XANSI | CAGHE |
|---|---|---|---|---|---|---|---|---|---|---|---|---|
| 41 | PRE | .05 | 30 | 80 | 80 | 30 | | 20 | 0 | 0 | 60 | 80 |
| | POST | .05 | 30 | 60 | 50 | 0 | | 30 | 20 | 0 | 70 | 0 |
| 42 | PRE | .05 | 40 | 10 | 60 | 0 | 40 | 0 | 0 | 0 | 0 | 35 |
| | POST | .05 | 20 | 0 | 20 | 0 | | 60 | 0 | 0 | 100 | 20 |
| 43 | PRE | .05 | 50 | 60 | | 20 | 70 | 20 | 0 | 20 | 0 | 20 |
| | POST | .05 | 70 | 60 | 0 | 0 | | 30 | 0 | 0 | 30 | 60 |
| 44 | PRE | .05 | 0 | 0 | 0 | 0 | 0 | 20 | 0 | 0 | 30 | 30 |
| | POST | .05 | 60 | 0 | 80 | 0 | | 0 | 20 | 0 | 90 | 50 |
| 45 | PRE | .05 | 100 | 100 | 100 | 100 | 100 | 30 | 90 | 90 | 75 | 100 |
| | POST | .05 | 100 | 100 | 100 | 100 | 100 | 60 | 100 | 100 | 100 | 100 |
| 46 | PRE | .05 | 100 | 90 | 100 | 60 | 100 | 20 | 50 | 65 | 100 | 100 |
| | POST | .05 | 90 | 100 | 100 | 50 | 100 | 0 | 80 | 50 | 100 | 30 |
| 47 | PRE | .05 | 20 | 70 | 0 | 0 | 0 | 70 | 0 | 0 | 0 | 0 |
| | POST | .05 | 40 | 35 | 0 | 0 | 0 | 70 | 15 | 0 | 30 | 0 |
| 48 | PRE | .05 | 100 | 60 | 0 | 40 | | 0 | 20 | 20 | 0 | 20 |
| | POST | .05 | 100 | 90 | 80 | 0 | 0 | 0 | 40 | 0 | 65 | 40 |
| 49 | PRE | .05 | 70 | 70 | 40 | 50 | | 0 | 20 | 20 | 0 | 0 |
| | POST | .05 | 100 | 70 | 100 | 20 | 0 | 0 | 50 | 0 | 70 | 30 |
| 50 | PRE | .06 | 100 | 100 | 90 | 100 | 100 | 50 | 70 | 20 | 80 | 100 |
| | POST | .05 | 100 | 100 | 90 | 80 | 90 | 50 | 90 | 70 | | 100 |
| 51 | PRE | .06 | 100 | 100 | 85 | 90 | 100 | 20 | 70 | 65 | 80 | 100 |
| | POST | .05 | 100 | 100 | 100 | 100 | 100 | 30 | 100 | 90 | | 100 |
| 52 | PRE | .06 | 90 | 90 | 60 | 70 | 85 | 25 | 60 | 70 | 70 | 60 |
| | POST | .05 | 90 | 100 | 90 | 60 | 70 | 50 | 90 | 60 | | 70 |
| 53 | PRE | .06 | 20 | 30 | 0 | 20 | 20 | 0 | 0 | 0 | 0 | 60 |
| | POST | .05 | 60 | 25 | 20 | 20 | 40 | 20 | 30 | 0 | | 0 |
| 54 | PRE | .06 | 90 | 90 | 40 | 90 | 50 | 20 | 90 | 80 | 90 | 100 |
| | POST | .05 | 100 | 90 | 90 | 90 | 40 | 40 | 100 | 90 | | 90 |
| 55 | PRE | .06 | 90 | 80 | 60 | 80 | 90 | 20 | 80 | 80 | 90 | 100 |
| | POST | .05 | 100 | 90 | 80 | 70 | 65 | 40 | 100 | 90 | | 90 |
| 56 | PRE | .05 | 90 | 30 | | 25 | 65 | 0 | 0 | 0 | 0 | 30 |
| | POST | .05 | 70 | 60 | 90 | 35 | 90 | 0 | 50 | 15 | 100 | 85 |
| 57 | PRE | .05 | 90 | 90 | 70 | 90 | 85 | 20 | 0 | 20 | 70 | 80 |
| | POST | .05 | 70 | 100 | 60 | 25 | 100 | 30 | 65 | 10 | 100 | 20 |
| 58 | PRE | .05 | 25 | 60 | 20 | 35 | 65 | 50 | 0 | 0 | 0 | 0 |
| | POST | .05 | 70 | 70 | 50 | 30 | 65 | 25 | 30 | 0 | 25 | 30 |
| 59 | PRE | .05 | 80 | 25 | 30 | 35 | 50 | 0 | 35 | 20 | 75 | 90 |
| | POST | .05 | 100 | 80 | 30 | 50 | 90 | 25 | 100 | 60 | 70 | 65 |
| 60 | PRE | .05 | 35 | 0 | 0 | 0 | 0 | 0 | 20 | 0 | 60 | 60 |
| | POST | .05 | 80 | 60 | 25 | 20 | 30 | 20 | 65 | 50 | 30 | 65 |
| 61 | PRE | .1 | 65 | 20 | 70 | 0 | 70 | 0 | 0 | 0 | | 80 |
| | POST | .1 | 70 | 55 | 80 | 0 | 0 | 20 | 0 | 0 | 0 | 80 |
| 62 | PRE | .1 | 100 | 100 | 100 | 100 | 100 | 50 | 90 | 90 | 90 | 100 |
| | POST | .1 | 100 | 100 | 100 | 70 | 100 | 25 | 70 | 25 | 100 | 100 |
| 63 | PRE | .05 | 50 | 20 | 0 | 0 | 20 | 0 | 0 | 0 | 50 | 90 |
| | POST | .05 | 60 | 50 | 20 | 40 | 40 | 20 | 0 | 0 | 10 | 100 |
| 64 | PRE | .1 | 100 | 80 | 100 | 70 | 70 | 60 | 50 | 90 | | 95 |
| | POST | .1 | 90 | 80 | 90 | 40 | 20 | 0 | 80 | 90 | 100 | 100 |
| 65 | PRE | .1 | 100 | 90 | 90 | 65 | 65 | 60 | 80 | 80 | 90 | 100 |
| | POST | .1 | 100 | 90 | 70 | 30 | 10 | 0 | 80 | 50 | 20 | 80 |
| 66 | PRE | .1 | 100 | 80 | 60 | 40 | 30 | 20 | 40 | 70 | 60 | 60 |
| | POST | .1 | 90 | 80 | 60 | 10 | 20 | 20 | 70 | 30 | 85 | 70 |
| 68 | PRE | .1 | 100 | 100 | 100 | 90 | 100 | 20 | 15 | 40 | | 100 |
| | POST | .1 | 80 | 90 | 90 | 80 | 95 | 30 | 20 | 30 | 90 | 100 |
| 76 | PRE | .05 | 100 | 100 | 100 | 100 | 100 | 60 | 0 | 0 | 10 | 20 |
| | POST | .05 | 90 | 65 | 95 | 65 | 100 | 40 | 0 | 0 | 0 | 50 |
| 77 | PRE | .05 | 100 | 100 | 100 | 100 | 100 | 20 | 0 | 30 | 90 | 60 |
| | POST | .05 | 80 | 100 | 100 | 100 | 100 | 30 | 100 | 30 | 100 | 100 |
| 78 | PRE | .05 | 100 | 80 | 10 | 60 | | 20 | 0 | 0 | 0 | 50 |
| | POST | .05 | 90 | 80 | 50 | 20 | 100 | 0 | 50 | 0 | 55 | 50 |
| 79 | PRE | .05 | 60 | 70 | 10 | 50 | 100 | 0 | 0 | 0 | 0 | 0 |
| | POST | .05 | 70 | 70 | 0 | 20 | | 20 | 60 | 0 | 40 | 60 |
| 80 | PRE | .05 | 100 | 100 | 100 | 90 | 100 | 90 | 10 | 50 | 50 | 100 |
| | POST | .05 | 90 | 100 | 100 | 80 | 100 | 50 | 60 | 50 | 100 | 100 |
| 81 | PRE | .05 | 100 | 100 | 100 | 100 | 100 | 90 | 90 | 90 | 90 | 100 |
| | POST | .05 | 100 | 100 | 100 | 100 | 100 | 90 | 100 | 60 | 100 | 100 |
| 82 | PRE | .05 | 100 | 100 | 70 | 100 | 100 | 30 | 60 | 60 | 80 | 100 |
| | POST | .05 | 90 | 100 | 90 | 90 | 100 | 0 | 100 | 60 | 100 | 100 |
| 83 | PRE | .05 | 60 | 100 | 100 | 20 | 80 | 60 | 0 | 0 | 0 | 90 |
| | POST | .05 | 60 | 90 | 0 | 0 | 100 | 40 | 30 | 0 | 40 | 60 |
| 84 | PRE | .05 | 40 | 100 | 70 | 60 | 100 | 20 | 0 | 0 | 50 | 65 |
| | POST | .05 | 80 | 100 | 70 | 30 | 100 | 30 | 60 | 20 | 70 | 90 |
| 85 | PRE | .05 | 10 | 100 | 20 | 30 | 80 | 70 | 0 | 0 | 0 | 60 |

-continued

| | | | | | BROJA | | | | | | | |
| Comp. | | | | | (SETVI) | | | | | | | |
| No. | TYPE | kg/ha | SORBI | ECHOR | [AGRSM] | DIGSA | PANDI | SOLNI | AESIN | ABUTH | XANSI | CAGHE |
|---|---|---|---|---|---|---|---|---|---|---|---|---|
| | POST | .05 | 30 | 70 | 0 | 20 | 0 | 40 | 40 | 0 | 20 | 40 |
| 86 | PRE | .05 | 100 | 100 | 100 | 100 | 100 | 80 | 90 | 90 | 100 | 100 |
| | POST | .05 | 100 | 100 | 100 | 100 | 100 | 100 | 100 | 100 | 100 | 100 |
| 87 | PRE | .05 | 90 | 70 | 70 | 40 | | 30 | 0 | 20 | 20 | 100 |
| | POST | .05 | 30 | 45 | 80 | 20 | | 20 | 20 | 0 | 60 | 20 |
| 88 | PRE | .05 | 65 | 100 | 60 | 90 | 100 | 0 | 0 | 0 | 20 | 55 |
| | POST | .05 | 50 | 70 | 100 | 20 | 100 | 20 | 0 | 0 | 60 | 50 |
| 89 | PRE | .05 | 30 | 40 | 30 | 30 | | 0 | 0 | 0 | 20 | 0 |
| | POST | .05 | 0 | 0 | 20 | 0 | | 30 | 0 | 0 | 0 | 50 |

PLANT RESPONSE SCREENING (Herbicide)

| Comp. No. | TYPE | kg/ha | UPLAND WEED SPECIES | | | | | | | | | | | | PADDY WEED SPECIES | | |
|---|---|---|---|---|---|---|---|---|---|---|---|---|---|---|---|---|---|
| | | | LYPES | TRZAW | GLXMX | ZEAMX | DACGL | AMAVI | SETVI (SETVI) | RUMJA | POLHY (COMCO) | AESIN | CAGHE | ORYSA | ECHOR | CYPDI | ANEKE |
| 4 | PRE | .1 | 90 | 100 | 100 | 100 | 90 | 100 | (100) | 85 | 100 | 100 | 100 | 100 | 100 | 100 | 60 |
| 4 | POST | .1 | 60 | 80 | 100 | 90 | 100 | 100 | (100) | 100 | 100 | 100 | 100 | 100 | 100 | 100 | 65 |
| 5 | PRE | .1 | 100 | 60 | 90 | 100 | 90 | 100 | (80) | 90 | 100 | 100 | 90 | 90 | 95 | 100 | 50 |
| 5 | POST | .1 | 90 | 35 | 85 | 90 | 100 | 100 | (60) | 90 | 85 | 100 | 100 | 100 | 90 | 100 | 10 |
| 6 | PRE | .1 | 90 | 100 | 90 | 90 | 100 | 100 | (100) | 90 | 100 | 90 | 100 | 90 | 90 | 90 | 20 |
| 6 | POST | .1 | 90 | 70 | 100 | 90 | 100 | 100 | (70) | 90 | 80 | 100 | 100 | 90 | 100 | 100 | 10 |
| 7 | PRE | .1 | 90 | 50 | 100 | 100 | 100 | 100 | (100) | 100 | 100 | 100 | 100 | 100 | 100 | 100 | 90 |
| 7 | POST | .1 | 70 | 45 | 100 | 100 | 100 | 100 | (100) | 100 | 100 | 100 | 100 | 100 | 100 | 100 | 70 |
| 8 | PRE | .1 | 90 | 60 | 100 | 100 | 90 | 100 | (100) | 90 | 100 | 100 | 100 | 90 | 100 | 100 | 80 |
| 8 | POST | .1 | 100 | 25 | 100 | 100 | 100 | 100 | (100) | 100 | 100 | 100 | 100 | 60 | 100 | 100 | 70 |
| 9 | PRE | .1 | 15 | 0 | 0 | 0 | 20 | 20 | (25) | 10 | 90 | 0 | 0 | 60 | 90 | 60 | 0 |
| 9 | POST | .1 | 30 | 10 | 15 | 0 | 60 | 60 | (25) | 30 | 95 | 0 | 25 | 60 | 10 | 30 | 0 |
| 10 | PRE | .1 | 40 | 65 | 15 | 90 | 70 | 90 | (90) | 70 | 100 | 100 | 90 | 90 | 90 | 100 | 20 |
| 10 | POST | .1 | 60 | 70 | 90 | 60 | 90 | 100 | (90) | 100 | 95 | 40 | 100 | 65 | 70 | 100 | 0 |
| 11 | PRE | .1 | 10 | 40 | 10 | 30 | 90 | 100 | (40) | 80 | 80 | 15 | 100 | 70 | 60 | 80 | 0 |
| 11 | POST | .1 | 85 | 10 | 80 | 30 | 65 | 100 | (95) | 65 | 95 | 10 | 95 | 60 | 60 | 100 | 0 |
| 12 | PRE | .1 | 70 | 10 | 65 | 20 | 75 | 100 | (60) | 40 | 100 | 65 | 100 | 100 | 80 | 100 | 80 |
| 12 | POST | .1 | 80 | 20 | 100 | 35 | 30 | 100 | (0) | 70 | 95 | 100 | 95 | 65 | 75 | 100 | 10 |
| 13 | PRE | .1 | 60 | 0 | 0 | 0 | 50 | 70 | (10) | 10 | 100 | 20 | 50 | 90 | 80 | 60 | 90 |
| 13 | POST | .1 | 20 | 10 | 45 | 0 | 0 | 0 | (0) | 20 | 100 | 0 | 20 | 35 | 25 | 60 | 0 |
| 14 | PRE | .1 | 50 | 0 | 0 | 0 | 0 | 0 | (0) | 15 | 90 | 0 | 15 | 0 | 0 | 0 | 0 |
| 14 | POST | .1 | 15 | 0 | 0 | 0 | 15 | 15 | (0) | 0 | 90 | 20 | 0 | 10 | 10 | 0 | 0 |
| 15 | PRE | .1 | 50 | 0 | 0 | 0 | 15 | 40 | (25) | 0 | 50 | 0 | 0 | 70 | 0 | 0 | 0 |
| 15 | POST | .1 | 20 | 10 | 0 | 0 | 70 | 40 | (20) | 0 | 60 | 20 | 0 | 10 | 0 | 0 | 0 |
| 16 | PRE | .1 | 90 | 15 | 100 | 100 | 90 | 90 | (70) | 85 | 95 | 80 | 80 | 90 | 80 | 70 | 50 |
| 16 | POST | .1 | 65 | 10 | 90 | 90 | 70 | 90 | (60) | 90 | 100 | 100 | 60 | 60 | 100 | 90 | 10 |
| 17 | PRE | .1 | 70 | 0 | 70 | 70 | 90 | 90 | (60) | 80 | 95 | 65 | 85 | 40 | 50 | 60 | 10 |
| 17 | POST | .1 | 50 | 10 | 90 | 90 | 20 | 90 | (20) | 95 | 100 | 90 | 60 | 35 | 30 | 0 | 0 |
| 18 | PRE | .1 | 95 | 10 | 100 | 90 | 65 | 100 | (90) | 70 | 100 | 65 | 85 | 80 | 40 | 0 | 10 |
| 18 | POST | .1 | 70 | 10 | 90 | 65 | 35 | 90 | (40) | 80 | 80 | 100 | 60 | 20 | 65 | 0 | 70 |
| 19 | PRE | .1 | 90 | 90 | 100 | 100 | 80 | 90 | (100) | 75 | 100 | 100 | 95 | 100 | 100 | 100 | 90 |
| 19 | POST | .1 | 70 | 40 | 100 | 90 | 100 | 90 | (80) | 80 | 100 | 90 | 90 | 100 | 100 | 95 | 30 |
| 23 | PRE | .1 | 100 | 10 | 100 | 100 | 80 | 90 | (100) | 75 | 100 | 100 | 90 | 70 | 95 | 65 | 70 |
| 23 | POST | .1 | 30 | 0 | 100 | 100 | 70 | 90 | (70) | 100 | 100 | 100 | 90 | 100 | 90 | 100 | 30 |
| 24 | PRE | .1 | 100 | 0 | 100 | 100 | 80 | 100 | (60) | 80 | 100 | 100 | 100 | 80 | 95 | 100 | 60 |
| 24 | POST | .1 | 85 | 0 | 100 | 100 | 70 | 90 | (100) | 80 | 100 | 70 | 100 | 100 | 90 | 100 | 40 |
| 31 | PRE | .1 | 90 | 90 | 70 | 100 | 80 | 90 | (100) | 100 | 100 | 90 | 90 | 70 | 90 | 100 | 0 |
| 31 | POST | .1 | 70 | 80 | 90 | 90 | 70 | 90 | (60) | 80 | 100 | 25 | 40 | 60 | 60 | 100 | 0 |
| 32 | PRE | .1 | 70 | 25 | 20 | 100 | 75 | 80 | (70) | 60 | 90 | 65 | 30 | 65 | 70 | 100 | 60 |
| 32 | POST | .1 | 70 | 35 | 70 | 90 | 70 | 90 | (100) | 60 | 100 | 25 | 90 | 100 | 100 | 100 | 0 |
| 33 | PRE | .1 | 30 | 20 | 30 | 90 | 70 | 90 | (100) | 70 | 100 | 100 | 100 | 90 | 100 | 100 | 60 |
| 33 | POST | .1 | 100 | 60 | 100 | 100 | 100 | 100 | (100) | 100 | 90 | 100 | 100 | 100 | 100 | 100 | 0 |
| 34 | PRE | .1 | 70 | 40 | 10 | 20 | 70 | 100 | (100) | 50 | 90 | 10 | 60 | 100 | 100 | 100 | 60 |

-continued

PLANT RESPONSE SCREENING (Herbicide)

| | | | UPLAND WEED SPECIES | | | | | | SETVI | | POLHY | | | PADDY WEED SPECIES | | | |
|---|---|---|---|---|---|---|---|---|---|---|---|---|---|---|---|---|---|---|
| Comp. No. | TYPE | kg/ha | LYPES | TRZAW | GLXMX | ZEAMX | DACGL | AMAVI | (SETVI) | RUMJA | (COMCO) | AESIN | CAGHE | ORYSA | ECHOR | CYPDI | ANEKE |
| 35 | POST | .1 | 100 | 40 | 70 | 90 | 100 | 100 | (100) | 100 | 90 | 90 | 30 | 100 | 100 | 100 | 30 |
|  | PRE | .1 | 70 | 10 | 20 | 10 | 20 | 90 | (90) | 40 | 80 | 0 | 10 | 90 | 70 | 100 | 0 |
| 36 | POST | .1 | 100 | 10 | 60 | 60 | 80 | 70 | (60) | 40 | 60 | 10 | 20 | 85 | 80 | 100 | 0 |
|  | PRE | .1 | 30 | 0 | 10 | 0 | 0 | 0 | (0) | 0 | 60 | 0 | 0 | 60 | 0 | 100 | 15 |
| 37 | POST | .1 | 65 | 0 | 55 | 0 | 15 | 50 | (55) | 60 | 50 | 30 | 0 | 60 | 0 | 100 | 0 |
|  | PRE | .1 | 100 | 10 | 100 | 100 | 100 | 90 | (100) | 70 | 100 | 100 | 100 | 80 | 90 | 100 | 90 |
| 38 | POST | .1 | 100 | 25 | 100 | 65 | 70 | 100 | (100) | 90 | 90 | 100 | 100 | 90 | 100 | 70 | 30 |
|  | PRE | .1 | 100 | 10 | 100 | 100 | 100 | 90 | (100) | 70 | 100 | 100 | 60 | 90 | 25 | 100 | 60 |
| 39 | POST | .1 | 100 | 20 | 90 | 90 | 10 | 100 | (100) | 100 | 90 | 70 | 60 | 30 | 70 | 100 | 0 |
|  | PRE | .1 | 100 | 20 | 100 | 100 | 70 | 100 | (100) | 90 | 100 | 100 | 100 | 90 | 60 | 100 | 0 |
| 67 | POST | .1 | 30 | 0 | 0 | 0 | 60 | 70 | (65) | 0 | 20 | 0 | 40 | 35 | 80 | 0 | 0 |
|  | PRE | .1 | 40 | 35 | 30 | 0 | 70 | 100 | (40) | 20 | | 10 | 80 | 80 | 65 | 100 | 0 |
| 69 | POST | .1 | 10 | 20 | 20 | 85 | 70 | 90 | (65) | 10 | 80 | 0 | 80 | 70 | 90 | 70 | 0 |
|  | PRE | .1 | 40 | 15 | 80 | 65 | 80 | 70 | (40) | 70 | 90 | 50 | 100 | 100 | 80 | 80 | 0 |
| 70 | POST | .1 | 55 | 0 | 0 | 0 | 20 | 40 | (60) | 0 | 0 | 0 | 0 | 60 | 20 | 100 | 0 |
|  | PRE | .1 | 65 | 10 | 70 | 90 | 55 | 60 | (0) | 10 | | 50 | 40 | 20 | 0 | 0 | 0 |
| 71 | POST | .1 | 90 | 20 | 85 | 100 | 80 | 90 | (80) | 20 | 90 | 30 | 80 | 20 | 40 | 100 | 10 |
|  | PRE | .1 | 70 | 10 | 60 | 40 | 100 | 100 | (60) | 70 | | 70 | 70 | 100 | 70 | 80 | 0 |
| 72 | POST | .1 | 70 | 10 | 90 | 20 | 30 | 70 | (65) | 25 | | 20 | 55 | 70 | 0 | 0 | 0 |
|  | PRE | .1 | 70 | 90 | 30 | 100 | 60 | 90 | (60) | 60 | | 65 | 65 | 25 | 90 | 100 | 40 |
| 73 | POST | .1 | 80 | 70 | 60 | 100 | 100 | 90 | (100) | 65 | 90 | 20 | 90 | 55 | 100 | 80 | 0 |
|  | PRE | .1 | 100 | 10 | 25 | 100 | 70 | 100 | (100) | 70 | | 65 | 100 | 100 | 65 | 0 | 15 |
| 74 | POST | .1 | 100 | 20 | 90 | 100 | 100 | 100 | (100) | 70 | 90 | 20 | 90 | 90 | 100 | 50 | 40 |
|  | PRE | .1 | 100 | 10 | 15 | 70 | 50 | 90 | (100) | 90 | 90 | 90 | 100 | 100 | 70 | 100 | 20 |
| 75 | POST | .1 | 90 | 10 | 85 | 100 | 65 | 100 | (100) | 90 | 100 | 20 | 65 | 60 | 90 | 100 | 0 |
|  | PRE | .1 | 100 | | | | | | (100) | | 100 | 65 | 65 | 60 | | 100 | 10 |

PRIMARY SCREENING (Herbicide)

| Comp. No. | TYPE | kg/ha | ZEAMX | GLXMX | GOSHI | TRZAW | ORYSA | SORBI | ECHOR | BROJA (SETVI) [AGRSM] | DIGSA | PANDI | SOLNI | AESIN | ABUTH | XANSI | CAGHE |
|---|---|---|---|---|---|---|---|---|---|---|---|---|---|---|---|---|---|
| 2 | PRE | .1 | 80 | 70 | 60 | 50 | 100 | 70 | 80 | 70 | 90 | 100 | 60 | 70 | 90 | 80 | 100 |
|  |  | .05 | 70 | 65 | 50 | 30 | 100 | 80 | 90 | 90 | 80 | 90 | 50 | 70 | 80 | 80 | 100 |
|  |  | .025 | 50 | 50 | 20 | 10 | 80 | 70 | 60 | 65 | 65 | 80 | 40 | 30 | 65 | 70 | 90 |
|  |  | .012 | 10 | 40 | 10 | 0 | 60 | 45 | 50 | 50 | 10 | 65 | 20 | 20 | 50 | 40 | 70 |
|  |  | .006 | 0 | 20 | 0 | 0 | 20 | 10 | 0 | 30 | 0 | 30 | 20 | 10 | 10 | 10 | 70 |
|  | POST | .1 | 70 | 100 | 50 | 60 | 100 | 90 | 90 | 80 | 30 | 100 | 20 | 100 | 90 | 100 | 100 |
|  |  | .05 | 70 | 100 | 30 | 30 | 80 | 80 | 65 | 70 | 20 | 20 | 20 | 100 | 40 | 100 | 100 |
|  |  | .025 | 20 | 100 | 20 | 20 | 50 | 70 | 50 | 65 | 10 | 20 | 10 | 80 | 30 | 100 | 100 |
|  |  | .012 | 10 | 100 | 20 | 10 | 30 | 70 | 40 | 50 | 10 | 20 | 10 | 65 | 20 | 100 | 40 |
|  |  | .006 | 0 | 100 | 0 | 0 | 30 | 30 | 10 | 40 | 10 | 20 | 0 | 40 | 20 | 60 | 0 |
| 20 | PRE | 1 | 70 | 60 | 100 | 30 | 100 | 100 | 100 | 70 | 80 | 90 | 90 | 30 | 90 | 70 | 100 |
|  |  | .05 | 40 | 50 | 60 | 0 | 70 | 90 | 100 | 60 | 70 | 90 | 90 | 30 | 70 | 90 | 100 |
|  |  | .025 | 20 | 45 | 40 | 0 | 50 | 70 | 70 | 30 | 40 | 70 | 70 | 10 | 60 | 70 | 50 |
|  |  | .012 | 0 | 20 | 40 | 0 | 40 | 30 | 50 | 0 | 20 | 50 | 50 | 0 | 0 | 60 | 0 |
|  |  | .006 | 0 | 0 | 0 | 0 | 0 | 20 | 30 | 0 | 0 | 30 | 30 | 0 | 0 | 0 | 0 |
|  | POST | .1 | 60 | 80 | 50 | 10 | 65 | 100 | 95 | 100 | 50 | 100 | 75 | 100 | 100 | 100 | 100 |
|  |  | .05 | 20 | 80 | 30 | 10 | 60 | 100 | 90 | 100 | 40 | 100 | 70 | 100 | 100 | 100 | 100 |
|  |  | .025 | 10 | 60 | 20 | 10 | 50 | 100 | 65 | 90 | 40 | 90 | 65 | 80 | 65 | 95 | 100 |
|  |  | .012 | 0 | 50 | 20 | 0 | 50 | 70 | 65 | 80 | 10 | 60 | 50 | 60 | 20 | 65 | 50 |
|  |  | .006 | 0 | 40 | 10 | 0 | 10 | 70 | 40 | 50 | 0 | 30 | 50 | 40 | 20 | 30 | 20 |
| 25 | PRE | .1 | 100 | 80 | 90 | 60 | 100 | 100 | 90 | 90 | 100 | 100 | 90 | 65 | 90 | 90 | 100 |
|  |  | .05 | 100 | 70 | 90 | 50 | 100 | 100 | 90 | 70 | 100 | 100 | 90 | 60 | 80 | 100 | 100 |
|  |  | .025 | 90 | 50 | 70 | 35 | 100 | 90 | 70 | 70 | 70 | 100 | 70 | 40 | 60 | 90 | 50 |
|  |  | .012 | 50 | 30 | 50 | 0 | 70 | 90 | 60 | 70 | 40 | 80 | 60 | 30 | 20 | 70 | 50 |
|  |  | .006 | 50 | 0 | 40 | 0 | 50 | 60 | 30 | 50 | 0 | 60 | 50 | 0 | 20 | 20 | 20 |
|  | POST | .1 | 100 | 100 | 60 | 95 | 100 | 100 | 80 | 100 | 100 | 100 | 85 | 100 | 100 | 100 | 100 |
|  |  | .05 | 100 | 100 | 50 | 90 | 100 | 100 | 85 | 100 | 100 | 100 | 80 | 60 | 100 | 100 | 100 |
|  |  | .025 | 90 | 70 | 40 | 65 | 100 | 100 | 65 | 100 | 90 | 100 | 70 | 40 | 85 | 90 | 50 |
|  |  | .012 | 65 | 65 | 30 | 30 | 100 | 100 | 60 | 100 | 90 | 100 | 50 | 30 | 70 | 65 | 50 |
|  |  | .006 | 10 | 50 | 10 | 20 | 100 | 80 | 60 | 95 | 30 | 80 | 50 | 0 | 50 | 40 | 20 |
| 26 | PRE | .1 | 100 | 100 | 100 | 100 | 100 | 100 | 100 | 100 | 100 | 100 | 90 | 100 | 100 | 100 | 100 |
|  |  | .05 | 100 | 100 | 100 | 90 | 100 | 100 | 90 | 100 | 100 | 100 | 70 | 80 | 90 | 100 | 100 |
|  |  | .025 | 100 | 80 | 100 | 80 | 100 | 80 | 90 | 100 | 100 | 100 | 60 | 70 | 80 | 80 | 100 |
|  |  | .012 | 90 | 70 | 60 | 60 | 100 | 90 | 90 | 90 | 90 | 100 | 50 | 40 | 80 | 80 | 100 |
|  |  | .006 | 0 | 60 | 65 | 100 | 100 | 80 | 100 | 100 | 90 | 100 | 20 | 100 | 90 | 100 | 100 |
|  | POST | .1 | 100 | 100 | 65 | 100 | 100 | 100 | 100 | 100 | 100 | 100 | 70 | 100 | 100 | 100 | 100 |
|  |  | .05 | 100 | 100 | 65 | 100 | 100 | 100 | 100 | 100 | 100 | 100 | 60 | 100 | 90 | 100 | 100 |
|  |  | .025 | 100 | 80 | 60 | 65 | 100 | 100 | 100 | 100 | 90 | 100 | 50 | 90 | 70 | 80 | 100 |
|  |  | .012 | 100 | 50 | 50 | 50 | 100 | 100 | 100 | 70 | 60 | 100 | 30 | 80 | 50 | 65 | 60 |
|  |  | .006 | 100 | 100 | 100 | 90 | 100 | 50 | 95 | 70 | 100 | 100 | 70 | 60 | 40 | 100 | 50 |
| 27 | PRE | .1 | 100 | 70 | 40 | 20 | 90 | 50 | 90 | (100) | 80 | 90 | 30 | 40 | 65 | 65 | 60 |
|  |  | .025 | 60 | 30 | 0 | 0 | 30 | 30 | 50 | (65) | 40 | 100 | 30 | 0 | 0 | 40 | 40 |
|  |  | .00625 | 0 | 0 | 0 | 0 | 0 | 0 | 30 | (30) | 0 | 90 | 0 | 0 | 0 | 0 | 0 |
|  |  | .00156 | 0 | 0 | 0 | 0 | 0 | 0 | 0 | (0) | 0 | 0 | 0 | 0 | 0 | 0 | 0 |
|  | POST | .1 | 100 | 100 | 100 | 70 | 100 | 100 | 100 | (100) | 100 | 100 | 50 | 100 | 100 | 100 | 100 |

-continued

PRIMARY SCREENING (Herbicide)

| Comp. No. | TYPE | kg/ha | ZEAMX | GLXMX | GOSHI | TRZAW | ORYSA | SORBI | ECHOR | BROJA (SETVI) [AGRSM] | DIGSA | PANDI | SOLNI | AESIN | ABUTH | XANSI | CAGHE |
|---|---|---|---|---|---|---|---|---|---|---|---|---|---|---|---|---|---|
| 28 | PRE | .025 | 70 | 100 | 50 | 50 | 100 | 100 | 65 | (100) | 100 | 100 | 50 | 100 | 100 | 100 | 100 |
| | | .00625 | 40 | 100 | 0 | 0 | 90 | 80 | 40 | (20) | 20 | 100 | 0 | 70 | 50 | 40 | 0 |
| | | .00156 | 0 | 40 | 0 | 40 | 40 | 30 | 0 | (0) | 0 | 60 | 0 | 40 | 0 | 0 | 0 |
| | POST | 1 | 100 | 80 | 90 | 0 | 100 | 90 | 100 | (30) | 100 | 100 | 100 | 60 | 80 | 100 | 100 |
| | | .025 | 50 | 30 | 20 | 0 | 80 | 30 | 60 | (0) | 40 | 100 | 60 | 0 | 40 | 40 | 100 |
| | | .00625 | 0 | 0 | 0 | 0 | 40 | 0 | 0 | (0) | 0 | 40 | 0 | 0 | 0 | 0 | 0 |
| | | .00156 | 0 | 0 | 0 | 0 | 0 | 0 | 0 | (0) | 0 | 0 | 0 | 0 | 0 | 0 | 0 |
| 29 | PRE | .1 | 80 | 100 | 50 | 40 | 90 | 100 | 100 | (65) | 40 | 100 | 100 | 100 | 100 | 100 | 65 |
| | | .025 | 70 | 50 | 0 | 0 | 90 | 30 | 30 | (20) | 0 | 50 | 90 | 65 | 70 | 80 | 30 |
| | | .00625 | 20 | 30 | 0 | 0 | 70 | 0 | 0 | (0) | 0 | 10 | 0 | 20 | 65 | 60 | 0 |
| | | .00156 | 0 | 0 | 0 | 0 | 20 | 0 | 0 | (0) | 0 | 0 | 0 | 0 | 0 | 0 | 0 |
| | POST | .1 | 100 | 100 | 100 | 50 | 100 | 100 | 100 | 100 | 100 | 100 | 90 | 90 | 100 | 100 | 100 |
| | | .05 | 100 | 100 | 90 | 10 | 100 | 100 | 100 | 100 | 100 | 90 | 80 | 90 | 100 | 100 | 100 |
| | | .025 | 100 | 100 | 90 | 0 | 100 | 100 | 100 | 100 | 90 | 80 | 60 | 90 | 100 | 100 | 100 |
| | | .012 | 100 | 100 | 90 | 0 | 100 | 100 | 80 | 80 | 90 | 70 | 0 | 50 | 70 | 90 | 100 |
| | | .006 | 100 | 90 | 80 | 0 | 90 | 90 | 100 | 65 | 100 | 65 | 70 | 80 | 80 | 90 | 65 |
| 30 | PRE | .1 | 100 | 90 | 90 | 90 | 100 | 90 | 90 | 70 | 100 | 90 | 70 | 80 | 80 | 90 | 70 |
| | | .05 | 100 | 90 | 90 | 50 | 100 | 90 | 80 | 60 | 100 | 90 | 70 | 70 | 70 | 90 | 60 |
| | | .025 | 90 | 90 | 90 | 60 | 100 | 80 | 70 | 60 | 90 | 90 | 60 | 70 | 70 | 90 | 50 |
| | | .012 | 40 | 70 | 0 | 25 | 100 | 60 | 50 | 30 | 40 | 50 | 60 | 50 | 50 | 70 | 40 |
| | | .006 | 0 | 0 | 0 | 0 | 60 | 0 | 30 | 20 | 0 | 30 | 60 | 30 | 30 | 70 | 40 |
| | POST | .1 | 100 | 0 | 90 | 0 | 100 | 100 | 100 | 100 | 100 | 100 | 60 | 100 | 100 | 100 | 100 |
| | | .05 | 100 | 0 | 90 | 40 | 100 | 100 | 80 | 100 | 100 | 100 | 60 | 100 | 100 | 100 | 100 |
| | | .025 | 90 | 0 | 50 | 40 | 100 | 90 | 60 | 100 | 100 | 90 | 50 | 100 | 100 | 100 | 100 |
| | | .012 | 80 | 0 | 30 | 10 | 50 | 90 | 50 | 100 | 90 | 95 | 40 | 100 | 90 | 10 | 60 |
| | | .006 | 10 | 90 | 10 | 30 | 30 | 90 | 20 | 70 | 70 | 100 | 40 | 100 | 65 | 100 | 40 |
| 40 | PRE | .1 | 0 | 0 | 0 | 0 | 100 | 10 | 60 | (40) | 60 | 60 | 0 | 0 | 0 | 40 | 10 |
| | | .05 | 0 | 0 | 0 | 0 | 90 | 0 | 20 | (0) | 40 | 40 | 0 | 0 | 0 | 20 | 0 |
| | | .025 | 0 | 0 | 0 | 0 | 60 | 0 | 0 | (0) | 30 | 30 | 0 | 0 | 0 | 0 | 0 |
| | | .0125 | 0 | 0 | 0 | 0 | 30 | 0 | 0 | (0) | 0 | 0 | 0 | 0 | 0 | 0 | 0 |
| | | .006 | 0 | 0 | 0 | 0 | 0 | 60 | 30 | (0) | 0 | 0 | 0 | 0 | 0 | 0 | 0 |
| | POST | .1 | 0 | 0 | 0 | 50 | 50 | 50 | 0 | (40) | 30 | 40 | 0 | 20 | 0 | 50 | 40 |
| | | .05 | 0 | 0 | 0 | 30 | 40 | 0 | 0 | (20) | 10 | 20 | 0 | 0 | 0 | 0 | 0 |
| | | .025 | 0 | 0 | 0 | 0 | 0 | 0 | 0 | (0) | 0 | 0 | 0 | 0 | 0 | 0 | 0 |
| | | .0125 | 0 | 0 | 0 | 0 | 0 | 0 | 0 | (0) | 0 | 0 | 0 | 0 | 0 | 0 | 0 |
| | | .006 | 0 | 0 | 0 | 0 | 0 | 0 | 0 | (0) | 0 | 0 | 0 | 0 | 0 | 0 | 0 |
| 41 | PRE | 1 | 100 | 20 | 40 | 50 | 100 | 90 | 60 | (50) | 50 | 70 | 70 | 20 | 0 | 80 | 100 |
| | | .05 | 50 | 0 | 0 | 20 | 70 | 40 | 40 | (40) | 20 | 40 | 40 | 0 | 0 | 70 | 60 |
| | | .025 | 20 | 0 | 0 | 0 | 50 | 20 | 20 | (0) | 0 | 40 | 30 | 0 | 0 | 0 | 0 |
| | | .0125 | 0 | 0 | 0 | 0 | 20 | 0 | 0 | (0) | 0 | 20 | 0 | 0 | 0 | 0 | 0 |
| | | .006 | 0 | 0 | 0 | 0 | 0 | 0 | 0 | (0) | 0 | 0 | 0 | 0 | 0 | 0 | 0 |

-continued

PRIMARY SCREENING (Herbicide)

| Comp. No. | TYPE | kg/ha | ZEAMX | GLXMX | GOSHI | TRZAW | ORYSA | SORBI | ECHOR | BROJA (SETVI) [AGRSM] | DIGSA | PANDI | SOLNI | AESIN | ABUTH | XANSI | CAGHE |
|---|---|---|---|---|---|---|---|---|---|---|---|---|---|---|---|---|---|
| 45 | POST | .1 | 70 | 40 | 20 | 20 | 60 | 40 | 40 | (20) | 0 | 30 | 0 | 20 | 0 | 80 | 100 |
| | | .05 | 40 | 10 | 0 | 0 | 40 | 30 | 20 | (0) | 0 | 20 | 0 | 0 | 0 | 50 | 100 |
| | | .0125 | 20 | 0 | 0 | 0 | 0 | 20 | 0 | (0) | 0 | 0 | 0 | 0 | 0 | 0 | 70 |
| | | .012 | 0 | 0 | 0 | 0 | 0 | 0 | 0 | (0) | 0 | 0 | 0 | 0 | 0 | 0 | 40 |
| | | .006 | 0 | 0 | 0 | 0 | 0 | 0 | 0 | (0) | 0 | 0 | 0 | 0 | 0 | 0 | 40 |
| | PRE | .1 | 0 | 0 | 0 | 0 | 40 | 40 | 30 | (0) | 20 | 40 | 50 | 0 | 0 | 20 | 40 |
| | | .05 | 0 | 0 | 0 | 0 | 40 | 0 | 0 | (0) | 0 | 0 | 0 | 0 | 0 | 0 | 20 |
| | | .025 | 0 | 0 | 0 | 0 | 0 | 0 | 0 | (0) | 0 | 0 | 0 | 0 | 0 | 0 | 0 |
| | | .0125 | 0 | 0 | 0 | 0 | 0 | 0 | 0 | (0) | 0 | 0 | 0 | 0 | 0 | 0 | 0 |
| | | .006 | 0 | 0 | 0 | 0 | 0 | 10 | 0 | (0) | 0 | 0 | 0 | 0 | 0 | 0 | 0 |
| | POST | .1 | 0 | 20 | 0 | 20 | 30 | 0 | 0 | (0) | 0 | 20 | 0 | 20 | 20 | 60 | 20 |
| | | .05 | 0 | 0 | 0 | 0 | 0 | 0 | 0 | (0) | 0 | 0 | 0 | 0 | 0 | 40 | 0 |
| | | .025 | 0 | 0 | 0 | 0 | 0 | 0 | 0 | (0) | 0 | 0 | 0 | 0 | 0 | 0 | 0 |
| | | .0125 | 0 | 0 | 0 | 0 | 0 | 0 | 0 | (0) | 0 | 0 | 0 | 0 | 0 | 0 | 0 |
| | | .006 | 0 | 0 | 0 | 0 | 0 | 0 | 0 | (0) | 0 | 0 | 0 | 0 | 0 | 0 | 0 |
| 50 | PRE | .1 | 100 | 50 | 40 | 60 | 100 | 100 | 100 | 100 | 100 | 100 | 90 | 30 | 60 | 90 | 100 |
| | | .05 | 100 | 40 | 20 | 40 | 100 | 100 | 60 | 100 | 100 | 100 | 80 | 10 | 20 | 90 | 90 |
| | | .025 | 50 | 20 | 0 | 30 | 90 | 100 | 30 | 90 | 80 | 60 | 80 | 0 | 0 | 50 | 60 |
| | | .0125 | 30 | 0 | 0 | 0 | 50 | 70 | 0 | 65 | 50 | 40 | 60 | 0 | 0 | 20 | 30 |
| | | .006 | 20 | 0 | 0 | 0 | 20 | 20 | 0 | 30 | 50 | 20 | 10 | 0 | 0 | 0 | 20 |
| | POST | .1 | 100 | 90 | 40 | 100 | 100 | 100 | 100 | 100 | 100 | 100 | 70 | 60 | 40 | 80 | 100 |
| | | .05 | 100 | 65 | 30 | 80 | 90 | 100 | 60 | 80 | 90 | 100 | 60 | 50 | 30 | 80 | 60 |
| | | .025 | 90 | 50 | 20 | 40 | 90 | 90 | 55 | 80 | 90 | 100 | 50 | 20 | 20 | 70 | 60 |
| | | .012 | 20 | 20 | 0 | 20 | 70 | 90 | 30 | 60 | 40 | 100 | 40 | 0 | 0 | 40 | 60 |
| | | .006 | 10 | 0 | 0 | 0 | 40 | 65 | 0 | 50 | 0 | 60 | 30 | 0 | 0 | 30 | 40 |
| 51 | PRE | .1 | 100 | 100 | 70 | 100 | 100 | 100 | 100 | 100 | 100 | 100 | 70 | 60 | 80 | 100 | 100 |
| | | .05 | 80 | 90 | 60 | 100 | 100 | 90 | 100 | 80 | 100 | 100 | 40 | 40 | 20 | 100 | 90 |
| | | .025 | 50 | 70 | 30 | 60 | 90 | 90 | 100 | 80 | 100 | 90 | 30 | 20 | 20 | 90 | 70 |
| | | .012 | 30 | 50 | 0 | 40 | 90 | 90 | 40 | 50 | 90 | 70 | 30 | 0 | 20 | 70 | 50 |
| | | .006 | 0 | 30 | 0 | 30 | 50 | 80 | 20 | 40 | 70 | 50 | 0 | 0 | 0 | 70 | 20 |
| | POST | .1 | 100 | 100 | 60 | 100 | 100 | 100 | 100 | 100 | 100 | 100 | 60 | 70 | 100 | 100 | 100 |
| | | .05 | 80 | 100 | 40 | 100 | 100 | 100 | 100 | 80 | 100 | 100 | 50 | 80 | 70 | 100 | 90 |
| | | .025 | 60 | 90 | 30 | 65 | 100 | 90 | 100 | 90 | 65 | 100 | 50 | 65 | 60 | 60 | 60 |
| | | .012 | 40 | 90 | 0 | 50 | 70 | 70 | 100 | 50 | 40 | 100 | 40 | 40 | 20 | 50 | 50 |
| | | .006 | 0 | 90 | 0 | 0 | 60 | 70 | 70 | 50 | 0 | 100 | 65 | 70 | 0 | 40 | 30 |
| 54 | PRE | .1 | 100 | 100 | 90 | 30 | 100 | 100 | 100 | 100 | 100 | 100 | 60 | 70 | 80 | 90 | 100 |
| | | .05 | 100 | 90 | 70 | 20 | 70 | 90 | 70 | 70 | 100 | 100 | 50 | 65 | 65 | 90 | 90 |
| | | .025 | 100 | 70 | 60 | 0 | 50 | 80 | 50 | 50 | 100 | 90 | 50 | 50 | 50 | 90 | 70 |
| | | .012 | 40 | 40 | 0 | 0 | 30 | 60 | 20 | 30 | 70 | 90 | 40 | 0 | 0 | 80 | 50 |
| | | .006 | 0 | 0 | 0 | 0 | 0 | 0 | 0 | 0 | 40 | 20 | 0 | 0 | 0 | 0 | 20 |
| | POST | .1 | 100 | 100 | 70 | 50 | 100 | 100 | 100 | 100 | 100 | 100 | 60 | 90 | 80 | 100 | 100 |
| | | .05 | 100 | 100 | 60 | 20 | 100 | 100 | 90 | 90 | 85 | 100 | 40 | 90 | 70 | 100 | 90 |
| | | .025 | 100 | 75 | 50 | 0 | 90 | 90 | 80 | 70 | 60 | 80 | 30 | 90 | 50 | 70 | 50 |
| | | .012 | 90 | 65 | 40 | 0 | 65 | 90 | 70 | 50 | 60 | 80 | 30 | 50 | 40 | 30 | 60 |
| | | .006 | 60 | 40 | 20 | 0 | 30 | 90 | 50 | 30 | 10 | 50 | 30 | 50 | 20 | 30 | 50 |
| 55 | PRE | .1 | 100 | 100 | 100 | 40 | 100 | 100 | 100 | 65 | 100 | 100 | 70 | 70 | 70 | 100 | 100 |

-continued

PRIMARY SCREENING (Herbicide)

| Comp. No. | TYPE | kg/ha | ZEAMX | GLXMX | GOSHI | TRZAW | ORYSA | SORBI | ECHOR | BROJA (SETVI) [AGRSM] | DIGSA | PANDI | SOLNI | AESIN | ABUTH | XANSI | CAGHE |
|---|---|---|---|---|---|---|---|---|---|---|---|---|---|---|---|---|---|
| | POST | .05 | 100 | 90 | 80 | 30 | 100 | 90 | 100 | 30 | 100 | 90 | 60 | 65 | 70 | 100 | 80 |
| | | .025 | 60 | 80 | 0 | 0 | 100 | 80 | 70 | 30 | 90 | 50 | 60 | 50 | 60 | 90 | 90 |
| | | .012 | 50 | 50 | 0 | 0 | 60 | 50 | 30 | 0 | 30 | 30 | 20 | 20 | 0 | 90 | 60 |
| | | .006 | 30 | 40 | 50 | 10 | 20 | 20 | 0 | 0 | 0 | 10 | 0 | 0 | 0 | 90 | 0 |
| | PRE | .1 | 100 | 100 | 50 | 0 | 100 | 90 | 100 | 80 | 100 | 100 | 50 | 100 | 100 | 100 | 100 |
| | | .05 | 90 | 90 | 40 | 0 | 100 | 90 | 70 | 70 | 30 | 80 | 40 | 90 | 70 | 100 | 100 |
| | | .025 | 90 | 80 | 20 | 0 | 100 | 70 | 50 | 30 | 0 | 80 | 30 | 65 | 60 | 100 | 100 |
| | | .012 | 40 | 70 | 20 | 0 | 50 | 70 | 50 | 0 | 0 | 80 | 20 | 40 | 20 | 60 | 80 |
| 62 | | .006 | 30 | 65 | 20 | 0 | 30 | 60 | 40 | 0 | 0 | 80 | 60 | 30 | 0 | 50 | 60 |
| | | 1 | 50 | 65 | 90 | 50 | 100 | 100 | 80 | 80 | 80 | 100 | 60 | 30 | 80 | 80 | 100 |
| | | .05 | 40 | 50 | 60 | 40 | 100 | 90 | 70 | 70 | 60 | 100 | 40 | 30 | 70 | 80 | 100 |
| | | .025 | 0 | 30 | 50 | 0 | 80 | 80 | 70 | 50 | 40 | 100 | 20 | 30 | 30 | 70 | 100 |
| | | .012 | 0 | 20 | 20 | 0 | 60 | 50 | 40 | 40 | 30 | 80 | 20 | 10 | 20 | 65 | 80 |
| | | .006 | 0 | 0 | 0 | 0 | 50 | 0 | 20 | 30 | 10 | 100 | 10 | 0 | 0 | 30 | 60 |
| | POST | .1 | 40 | 80 | 70 | 60 | 95 | 70 | 90 | 70 | 90 | 100 | 40 | 100 | 30 | 75 | 100 |
| | | .05 | 30 | 75 | 40 | 40 | 80 | 65 | 60 | 70 | 40 | 100 | 30 | 60 | 20 | 0 | 80 |
| | | .025 | 10 | 70 | 30 | 20 | 60 | 60 | 40 | 40 | 40 | 100 | 20 | 40 | 10 | 0 | 65 |
| | | .012 | 10 | 60 | 10 | 10 | 50 | 45 | 20 | 30 | 20 | 100 | 10 | 20 | 0 | 0 | 60 |
| | | .006 | 0 | 40 | 0 | 0 | 40 | 20 | 0 | 10 | 0 | 80 | 0 | 0 | 0 | 0 | 20 |
| 64 | PRE | .1 | 10 | 40 | 50 | 0 | 65 | 60 | 40 | 60 | 50 | 100 | 40 | 65 | 40 | 90 | 90 |
| | | .05 | 0 | 20 | 0 | 0 | 60 | 60 | 30 | 30 | 40 | 80 | 30 | 20 | 20 | 65 | 90 |
| | | .025 | 0 | 0 | 0 | 0 | 30 | 30 | 10 | 0 | 0 | 20 | 20 | 0 | 0 | 0 | 80 |
| | | .012 | 0 | 0 | 0 | 0 | 0 | 0 | 0 | 0 | 0 | 0 | 10 | 0 | 0 | 0 | 60 |
| | | .006 | 0 | 0 | 0 | 0 | 0 | 0 | 0 | 0 | 0 | 0 | 0 | 0 | 0 | 0 | 40 |
| | POST | .1 | 10 | 80 | 10 | 0 | 50 | 70 | 60 | 70 | 30 | 100 | 40 | 100 | 30 | 80 | 90 |
| | | .05 | 0 | 80 | 10 | 0 | 40 | 60 | 40 | 65 | 30 | 100 | 40 | 90 | 20 | 100 | 100 |
| | | .025 | 0 | 70 | 0 | 0 | 30 | 40 | 10 | 40 | 10 | 100 | 30 | 40 | 0 | 0 | 40 |
| | | .012 | 0 | 65 | 0 | 0 | 20 | 30 | 0 | 30 | 0 | 80 | 10 | 10 | 0 | 0 | 90 |
| | | .006 | 0 | 50 | 0 | 0 | 10 | 30 | 0 | 10 | 0 | 20 | 50 | 0 | 0 | 30 | 100 |
| 68 | PRE | 1 | 70 | 50 | 50 | 30 | 100 | 80 | 70 | 65 | 80 | 100 | 50 | 40 | 50 | 80 | 40 |
| | | .05 | 50 | 40 | 50 | 0 | 70 | 50 | 60 | 50 | 65 | 100 | 50 | 30 | 30 | 50 | 20 |
| | POST | .05 | 80 | 70 | 40 | 40 | 60 | 70 | 90 | 75 | 90 | 100 | 30 | 0 | 30 | 0 | 100 |
| 76 | PRE | 1 | 100 | 50 | 20 | 10 | 100 | 60 | 65 | (90) | 80 | 20 | 60 | 0 | 10 | 60 | 100 |
| | | .05 | 50 | 0 | 30 | 30 | 100 | 100 | 100 | (90) | 100 | 0 | 40 | 0 | 0 | 20 | 100 |
| | | .025 | 10 | 0 | 10 | 0 | 90 | 80 | 70 | (50) | 70 | 0 | 30 | 0 | 0 | 0 | 40 |
| | | .0125 | 50 | 0 | 0 | 0 | 40 | 50 | 50 | (20) | 40 | 0 | 60 | 0 | 0 | 0 | 10 |
| | | .006 | 0 | 0 | 0 | 0 | 0 | 30 | 0 | (0) | 0 | 0 | 0 | 0 | 0 | 0 | 0 |
| | POST | .1 | 100 | 40 | 70 | 30 | 70 | 100 | 100 | (100) | 100 | 100 | 60 | 20 | 0 | 20 | 100 |
| | | .05 | 100 | 30 | 60 | 10 | 40 | 60 | 40 | (80) | 100 | 80 | 60 | 0 | 0 | 0 | 50 |
| | | .025 | 80 | 0 | 30 | 0 | 0 | 40 | 40 | (40) | 80 | 20 | 60 | 0 | 0 | 0 | 40 |
| | | .0125 | 0 | 0 | 0 | 0 | 0 | 0 | 0 | (0) | 20 | 0 | 30 | 0 | 65 | 0 | 10 |
| | | .006 | 0 | 0 | 0 | 0 | 0 | 0 | 0 | (0) | 0 | 0 | 0 | 0 | 0 | 0 | 0 |
| 77 | PRE | .1 | 100 | 70 | 70 | 30 | 100 | 100 | 100 | (100) | 100 | 100 | 40 | 40 | 0 | 80 | 100 |
| | | .05 | 100 | 50 | 60 | 10 | 100 | 80 | 100 | (100) | 100 | 100 | 30 | 10 | 0 | 40 | 70 |
| | | .025 | 20 | 20 | 30 | 0 | 80 | 80 | 100 | (65) | 100 | 100 | 0 | 0 | 0 | 0 | 60 |

5,461,024

-continued

PRIMARY SCREENING (Herbicide)

| Comp. No. | TYPE | kg/ha | ZEAMX | GLXMX | GOSHI | TRZAW | ORYSA | SORBI | ECHOR | BROJA (SETVI) [AGRSM] | DIGSA | PANDI | SOLNI | AESIN | ABUTH | XANSI | CAGHE |
|---|---|---|---|---|---|---|---|---|---|---|---|---|---|---|---|---|---|
|  | POST | .1 | 100 | 100 | 40 | 0 | 60 | 100 | 100 | (100) | 100 | 100 | 60 | 100 | 60 | 100 | 100 |
|  |  | .05 | 100 | 100 | 30 | 0 | 50 | 100 | 100 | (100) | 100 | 100 | 50 | 80 | 40 | 100 | 100 |
|  |  | .025 | 40 | 100 | 20 | 0 | 50 | 40 | 100 | (100) | 50 | 100 | 30 | 65 | 0 | 0 | 100 |
| 80 | PRE | .1 | 100 | 40 | 50 | 70 | 100 | 100 | 100 | (100) | 100 | 100 | 50 | 0 | 40 | 100 | 100 |
|  |  | .05 | 60 | 30 | 30 | 40 | 80 | 90 | 70 | (50) | 100 | 100 | 30 | 0 | 0 | 50 | 100 |
|  |  | .025 | 40 | 0 | 0 | 40 | 90 | 100 | 70 | (40) | 60 | 100 | 0 | 0 | 0 | 30 | 100 |
|  | POST | .1 | 100 | 40 | 0 | 70 | 100 | 100 | 100 | (70) | 100 | 100 | 0 | 65 | 20 | 40 | 100 |
|  |  | .05 | 100 | 20 | 0 | 40 | 90 | 100 | 60 | (60) | 60 | 100 | 0 | 40 | 0 | 10 | 60 |
|  |  | .025 | 40 | 0 | 0 | 0 | 60 | 40 | 60 | (50) | 50 | 60 | 0 | 20 | 0 | 0 | 60 |
| 81 | PRE | .1 | 100 | 100 | 100 | 100 | 100 | 100 | 100 | (100) | 100 | 100 | 60 | 90 | 100 | 80 | 100 |
|  |  | .05 | 100 | 100 | 100 | 100 | 100 | 100 | 100 | (100) | 100 | 100 | 50 | 80 | 100 | 80 | 100 |
|  |  | .025 | 100 | 90 | 90 | 70 | 100 | 100 | 100 | (100) | 100 | 100 | 50 | 50 | 90 | 70 | 100 |
|  |  | .0125 | 100 | 70 | 65 | 40 | 100 | 90 | 100 | (100) | 100 | 100 | 0 | 40 | 50 | 50 | 100 |
|  |  | .006 | 90 | 60 | 50 | 0 | 100 | 100 | 100 | (70) | 100 | 80 | 0 | 0 | 30 | 30 | 60 |
|  | POST | .1 | 100 | 100 | 70 | 100 | 100 | 100 | 100 | (100) | 100 | 100 | 0 | 100 | 60 | 100 | 100 |
|  |  | .05 | 100 | 90 | 70 | 60 | 100 | 100 | 100 | (100) | 100 | 100 | 0 | 100 | 40 | 60 | 100 |
|  |  | .025 | 100 | 70 | 50 | 50 | 100 | 100 | 100 | (70) | 100 | 100 | 0 | 90 | 30 | 30 | 100 |
|  |  | .0125 | 100 | 50 | 20 | 40 | 100 | 50 | 100 | (60) | 100 | 80 | 0 | 70 | 0 | 0 | 100 |
|  |  | .006 | 100 | 40 | 0 | 0 | 80 | 30 | 60 | (60) | 60 | 80 | 0 | 50 | 0 | 0 | 60 |
| 82 | PRE | 1 | 100 | 100 | 100 | 50 | 100 | 100 | 100 | (100) | 100 | 100 | 0 | 70 | 90 | 90 | 100 |
|  |  | .05 | 100 | 100 | 90 | 10 | 100 | 100 | 100 | (100) | 100 | 100 | 0 | 40 | 50 | 80 | 100 |
|  |  | .025 | 70 | 80 | 70 | 0 | 100 | 70 | 100 | (90) | 100 | 100 | 0 | 20 | 20 | 80 | 80 |
|  |  | .0125 | 60 | 70 | 50 | 0 | 100 | 50 | 60 | (60) | 100 | 100 | 0 | 0 | 0 | 60 | 80 |
|  |  | .006 | 30 | 50 | 40 | 0 | 50 | 30 | 40 | (60) | 100 | 100 | 0 | 0 | 0 | 40 | 40 |
|  | POST | .1 | 60 | 100 | 70 | 20 | 70 | 100 | 100 | (100) | 100 | 100 |  | 100 | 80 | 80 | 100 |
|  |  | .05 | 50 | 100 | 50 | 0 | 60 | 50 | 100 | (80) | 100 | 100 | 0 | 100 | 70 | 30 | 30 |
|  |  | .025 | 40 | 70 | 40 | 0 | 50 | 50 | 100 | (50) | 50 | 100 | 0 | 80 | 0 | 20 | 0 |
|  |  | .0125 | 30 | 50 | 20 | 0 | 40 | 40 | 70 | (50) | 50 | 90 | 0 | 70 | 0 | 0 | 0 |
|  |  | .006 | 0 | 0 | 0 | 0 | 40 | 40 | 70 | (40) | 40 | 80 | 0 | 60 | 0 | 0 | 0 |
| 86 | PRE | 1 | 0 | 0 | 0 | 0 | 0 | 100 | 30 | (0) | 80 | 65 | 50 | 0 | 40 | 30 | 0 |
|  | PRE | .05 | 0 | 0 | 0 | 0 | 50 | 50 | 65 | (40) | 0 | 40 | 30 | 0 | 0 | 0 | 0 |
| 87 | PRE | 1 | 40 | 30 | 20 | 0 | 50 | 60 | 40 | (40) | 50 | 70 | 40 | 0 | 0 | 80 | 40 |
|  |  | .05 | 10 | 0 | 0 | 20 | 20 | 30 | 65 | (20) | 20 | 60 | 0 | 0 | 0 | 60 | 20 |
|  | POST | .1 | 50 | 20 | 10 | 20 | 50 | 30 | 40 | (40) | 10 | 40 | 50 | 40 | 0 | 70 | 50 |
|  |  | .05 | 20 | 10 | 0 | 0 | 20 | 20 | 70 | (0) | 0 | 0 | 0 | 0 | 0 | 40 | 0 |

| | | | PRIMARY SCREENING (PADDY SUBMERGED)- Herbicide | | | | | | |
|---|---|---|---|---|---|---|---|---|---|
| Comp. No. | DAT | kg/ha | ORYSA (3 Leaf) | ORYSA (seed) | ECHOR | SCPJU | MOOVA | CYPSE | SAGPY |
| 1 | 2 | .05 | 60 | 60 | 50 | 80 | 70 | 100 | 80 |
| 2 | 2 | .05 | 60 | 70 | 60 | 100 | 90 | 90 | 90 |
| 3 | 3 | .05 | 40 | 70 | 40 | 40 | 70 | 70 | 70 |
| 20 | 2 | .1 | 90 | 80 | 80 | 100 | 90 | 100 | 80 |
| | | .1 | 100 | 90 | 100 | 100 | 100 | 100 | 100 |
| | | .05 | 90 | 90 | 80 | 100 | 100 | 100 | 100 |
| | | .025 | 80 | 90 | 80 | 100 | 100 | 100 | 90 |
| | | .012 | 70 | 60 | 70 | 90 | 100 | 100 | 80 |
| | | .006 | 50 | 40 | 50 | 80 | 90 | 80 | 60 |
| 21 | 2 | .05 | 30 | 50 | 50 | 70 | 70 | 90 | 80 |
| 22 | 2 | .05 | 60 | 60 | 50 | 80 | 70 | 70 | 70 |
| 25 | 2 | .05 | 50 | 70 | 60 | 100 | 90 | 80 | 90 |
| | 3 | .1 | 80 | 100 | 100 | 100 | 100 | 100 | 100 |
| | | .05 | 80 | 100 | 90 | 100 | 100 | 100 | 10 |
| | | .025 | 80 | 100 | 70 | 100 | 90 | 100 | 100 |
| | | .012 | 80 | 100 | 60 | 100 | 90 | 90 | 90 |
| | | .006 | 80 | 100 | 50 | 90 | 90 | 70 | 90 |
| 26 | 2 | .05 | 60 | 90 | 100 | 100 | 90 | 70 | 70 |
| | 3 | .1 | 80 | 100 | 100 | 100 | 100 | 100 | 100 |
| | | .05 | 80 | 100 | 100 | 100 | 100 | 100 | 90 |
| | | .025 | 80 | 100 | 90 | 100 | 100 | 100 | 90 |
| | | .012 | 80 | 100 | 80 | 100 | 100 | 90 | 90 |
| | | .006 | 80 | 100 | 70 | 100 | 100 | 90 | 90 |
| 27 | 2 | .05 | 90 | 100 | 100 | 100 | 100 | 100 | 100 |
| | | .1 | 100 | 100 | 100 | 100 | 100 | | 100 |
| | | .025 | 100 | 100 | 100 | 100 | 100 | | 90 |
| | | .006 | 100 | 100 | 80 | 70 | 100 | 100 | 90 |
| | | .0015 | 50 | 50 | 0 | 40 | 100 | | 50 |
| | | .0004 | 30 | 20 | 0 | 0 | 0 | | 0 |
| 28 | 2 | .05 | 90 | 100 | 100 | 100 | 100 | 100 | 100 |
| | | .1 | 100 | 100 | 100 | 100 | 100 | | 90 |
| | | .025 | 100 | 90 | 100 | 100 | 100 | | 70 |
| | | .006 | 70 | 80 | 50 | 60 | 80 | | 40 |
| | | .0015 | 60 | 40 | 0 | 30 | 40 | | 20 |
| 29 | 2 | .05 | 60 | 80 | 70 | 100 | 90 | 40 | 90 |
| | 3 | .1 | 80 | 100 | 100 | 100 | 100 | 70 | 100 |
| | | .05 | 80 | 100 | 80 | 100 | 100 | 60 | 100 |
| | | .025 | 80 | 100 | 50 | 100 | 70 | 30 | 100 |
| | | .012 | 50 | 30 | 0 | 50 | 50 | 0 | 80 |
| | | .006 | 30 | 0 | 0 | 30 | 30 | 0 | 60 |
| 30 | 2 | .05 | 60 | 80 | 70 | 90 | 90 | 40 | 90 |
| | 3 | .1 | 80 | 100 | 100 | 100 | 100 | 90 | 100 |
| | | .05 | 80 | 100 | 100 | 100 | 100 | 80 | 100 |
| | | .025 | 70 | 100 | 90 | 100 | 100 | 50 | 100 |
| | | .012 | 60 | 100 | 10 | 100 | 100 | 40 | 90 |
| | | .006 | 50 | 100 | 0 | 90 | 90 | 20 | 70 |
| 40 | 2 | .05 | 50 | 40 | 0 | 20 | 0 | 30 | 0 |
| 42 | 2 | .05 | 30 | 0 | 10 | 60 | 30 | 90 | 50 |
| 43 | 2 | .05 | 0 | 0 | 0 | 0 | 30 | 0 | 0 |
| 44 | 2 | .05 | 40 | 30 | 0 | 0 | 60 | 40 | 0 |
| 45 | 2 | .05 | 60 | 60 | 40 | 50 | 60 | 80 | 60 |
| 46 | 2 | .05 | 60 | 60 | 60 | 90 | 90 | 90 | 70 |
| | 3 | .1 | 90 | 100 | 100 | 100 | 100 | 100 | 90 |
| | | .025 | 90 | 90 | 60 | 100 | 90 | 100 | 80 |
| | | .006 | 40 | 70 | 50 | 60 | 50 | 100 | 60 |
| 47 | 2 | .05 | 60 | 50 | 0 | 10 | 50 | 70 | 0 |
| 48 | 2 | .05 | 60 | 50 | 20 | 50 | 60 | 40 | 0 |
| 49 | 2 | .05 | 50 | 60 | | 100 | 70 | 60 | 0 |
| | 3 | .1 | 80 | 90 | 80 | 80 | 70 | 80 | 70 |
| | | .025 | 30 | 40 | 50 | 30 | 20 | 0 | 0 |
| | | .006 | 0 | 0 | 10 | 0 | 0 | 0 | 0 |
| 50 | 1 | .05 | 80 | 70 | 40 | 90 | 90 | 70 | 60 |
| 51 | 1 | .05 | 70 | 80 | 100 | 100 | 100 | 100 | 90 |
| | 2 | .1 | 100 | 100 | 100 | 100 | 100 | 100 | 100 |
| | | .025 | 100 | 100 | 90 | 100 | 100 | 100 | 90 |
| | | .006 | 80 | 80 | 70 | 60 | 100 | 80 | 90 | 90 |
| | | .0015 | 40 | 20 | 60 | 70 | 30 | 40 | 40 |
| 52 | 1 | .05 | 70 | 80 | 70 | 100 | 100 | 90 | 70 |
| | 3 | .1 | 90 | 100 | 100 | 100 | 100 | 100 | 90 |
| | | .025 | 80 | 90 | 80 | 100 | 80 | 100 | 80 |
| | | .006 | 60 | 30 | 10 | 30 | 20 | 90 | 50 |
| 53 | 1 | .05 | 60 | 70 | 50 | 90 | 100 | 100 | 40 |
| | 2 | .1 | 80 | 90 | 90 | 100 | 90 | 100 | 60 |
| | | .025 | 50 | 30 | 40 | 60 | 70 | 80 | 20 |

-continued

| | | | PRIMARY SCREENING (PADDY SUBMERGED)- Herbicide | | | | | | |
|---|---|---|---|---|---|---|---|---|---|
| Comp. No. | DAT | kg/ha | ORYSA (3 Leaf) | ORYSA (seed) | ECHOR | SCPJU | MOOVA | CYPSE | SAGPY |
| | | .006 | 10 | 0 | 20 | 10 | 0 | 0 | 0 |
| 54 | 1 | .05 | 80 | 90 | 60 | 100 | 100 | 50 | 90 |
| | 2 | .1 | 90 | 100 | 80 | 100 | 100 | 70 | 90 |
| | | .025 | 80 | 70 | 50 | 100 | 100 | 50 | 80 |
| | | .006 | 50 | 10 | 0 | 0 | 90 | 0 | 20 |
| 55 | 1 | .05 | 70 | 70 | 50 | 100 | 100 | 60 | 60 |
| 56 | 2 | .05 | 0 | 0 | 0 | 0 | 0 | 40 | 0 |
| 57 | 2 | .05 | 60 | 60 | 80 | 100 | 80 | 100 | 90 |
| 58 | 2 | .05 | 0 | 30 | 50 | 70 | 50 | 70 | 40 |
| | 3 | .5 | 100 | 100 | 100 | | 100 | 100 | 100 |
| | | .25 | 60 | 90 | 100 | | 100 | 100 | 100 |
| | | .125 | 40 | 65 | 100 | | 90 | 100 | 85 |
| | | .0625 | 30 | 30 | 100 | | 90 | 90 | 80 |
| | | .0312 | 0 | 0 | 90 | | 90 | 90 | 75 |
| 59 | 2 | .05 | 20 | 50 | 30 | 70 | 70 | 0 | 40 |
| 60 | 2 | .05 | 0 | 0 | 40 | 20 | 40 | 0 | 0 |
| 61 | 2 | .1 | 60 | 50 | 20 | 30 | 0 | 40 | 40 |
| 62 | 2 | .1 | 70 | 60 | 70 | 90 | 80 | 100 | 80 |
| | | .1 | 70 | 70 | 80 | 100 | 100 | 100 | 100 |
| | | .05 | 70 | 60 | 50 | 100 | 20 | 70 | 100 |
| | | .025 | 70 | 50 | 30 | 80 | 0 | 60 | 80 |
| | | .012 | 40 | 30 | 0 | 60 | 0 | 30 | 60 |
| | | .006 | 0 | 20 | 0 | 20 | 0 | 20 | 20 |
| 63 | 1 | .05 | 70 | 70 | 20 | 70 | 40 | 40 | 80 |
| 64 | 2 | .1 | 50 | 60 | 60 | 90 | 90 | 90 | 80 |
| | | .1 | 70 | 80 | 70 | 100 | 100 | 100 | 100 |
| | | .05 | 70 | 80 | 50 | 100 | 100 | 100 | 100 |
| | | .025 | 70 | 70 | 10 | 90 | 60 | 60 | 90 |
| | | .012 | 60 | 30 | 0 | 80 | 40 | 20 | 30 |
| | | .006 | 30 | 20 | 0 | 80 | 0 | 0 | 30 |
| 65 | 2 | .1 | 60 | 90 | 40 | 40 | 60 | 30 | 50 |
| 66 | 2 | .1 | 50 | 60 | 30 | 40 | 50 | 30 | 50 |
| 68 | 2 | .1 | 60 | 60 | 80 | 90 | 60 | 70 | 90 |
| 76 | 2 | .05 | 60 | 50 | 20 | 40 | 40 | 50 | 0 |
| 77 | 2 | .05 | 60 | 70 | 70 | 90 | 90 | 90 | 60 |
| | 3 | .1 | 90 | 100 | 100 | 100 | 100 | 100 | 90 |
| | | .025 | 90 | 90 | 50 | 100 | 100 | 100 | 90 |
| | | .006 | 60 | 80 | 20 | 80 | 60 | 100 | 90 |
| 78 | 2 | .05 | 50 | 50 | 40 | 50 | 70 | 0 | 0 |
| 79 | 2 | .05 | 40 | 50 | 10 | 30 | 40 | 30 | 0 |
| 80 | 2 | .05 | 70 | 20 | 0 | 10 | 30 | 0 | 40 |
| 81 | 2 | .05 | 60 | 50 | 100 | 100 | 100 | 60 | 100 |
| | | .1 | 90 | 100 | 100 | | 100 | | 90 |
| | | .025 | 90 | 70 | 90 | | 100 | | 90 |
| | | .006 | 20 | 10 | 0 | | 0 | | 20 |
| 82 | 2 | .05 | 80 | 90 | 90 | 100 | 100 | 100 | 100 |
| | | .1 | 100 | 100 | 100 | | 100 | | 100 |
| | | .025 | 100 | 90 | 100 | | 100 | | 80 |
| | | .006 | 90 | 50 | 30 | | 0 | | 40 |
| 83 | 2 | .05 | 60 | 50 | 60 | 30 | 40 | 70 | 50 |
| 84 | 2 | .05 | 30 | 20 | 0 | 0 | 0 | 0 | 20 |
| 85 | 2 | .05 | 10 | 10 | 20 | 40 | 70 | 0 | 0 |
| 86 | 2 | .05 | 0 | 0 | 20 | 20 | 30 | 0 | 0 |
| 87 | 2 | .05 | 0 | 0 | 0 | 0 | 0 | 0 | 0 |
| 88 | 2 | .05 | 0 | 0 | 0 | 0 | 0 | 0 | 0 |
| 89 | 2 | .05 | 0 | 0 | 0 | 0 | 0 | 0 | 0 |

| | | PRIMARY SCREENING (PADDY SUBMERGED)- Herbicide | | | | | | |
|---|---|---|---|---|---|---|---|---|
| Comp. No. | DAT | kg/ha | ORYSA | ECHOR | SCPJU | BR.s | CYPSE | SAGPY |
| 4 | 2 | .125 | 80 | 90 | 90 | 90 | 100 | 90 |
| | | .05 | 90 | 100 | 100 | 100 | 100 | 100 |
| | | .01 | 80 | 90 | 100 | 80 | 100 | 100 |
| | | .005 | 70 | 90 | 100 | 50 | 100 | 100 |
| 5 | 2 | .125 | 70 | 80 | 100 | 100 | 100 | 90 |
| 6 | 2 | .125 | 70 | 80 | 90 | 80 | 70 | 80 |
| 7 | 2 | .125 | 80 | 90 | 100 | 90 | 50 | 70 |
| 8 | 2 | .125 | 70 | 80 | 100 | 90 | 70 | 100 |

-continued

| | | | PRIMARY SCREENING (PADDY SUBMERGED)- Herbicide | | | | | |
|---|---|---|---|---|---|---|---|---|
| Comp. No. | DAT | kg/ha | ORYSA | ECHOR | SCPJU | BR.s | CYPSE | SAGPY |
| 9 | 2 | .125 | 40 | 40 | 40 | 50 | 20 | 40 |
| 10 | 2 | .1 | 60 | 60 | 100 | 60 | 60 | 50 |
| 11 | 2 | .1 | 40 | 40 | 0 | 70 | 60 | 60 |
| 12 | 2 | .1 | 50 | 60 | 20 | 80 | 100 | 70 |
| 13 | 2 | .125 | 40 | 50 | 30 | 30 | 70 | 50 |
| 14 | 2 | .1 | 10 | 0 | 30 | 60 | 60 | 40 |
| 15 | 2 | .1 | 30 | 0 | 20 | 60 | 40 | 30 |
| 16 | 2 | .125 | 60 | 50 | 80 | 80 | 30 | 70 |
| 17 | 2 | .125 | 0 | 30 | 70 | 50 | 40 | 60 |
| 18 | 2 | .1 | 10 | 20 | 0 | 70 | 50 | 70 |
| 19 | 2 | .1 | 90 | 90 | 90 | 90 | 100 | 100 |
| 23 | 2 | .1 | 60 | 90 | 100 | 100 | 100 | 100 |
| 24 | 2 | .1 | 50 | 100 | 100 | 100 | 100 | 100 |
| 31 | 2 | .125 | 60 | 80 | 90 | 90 | 80 | 60 |
| 32 | 2 | .125 | 10 | 60 | 70 | 70 | 40 | 50 |
| 33 | 2 | .125 | 70 | 100 | 100 | 100 | 100 | 90 |
| 34 | 2 | .125 | 90 | 100 | 100 | 100 | 100 | 80 |
| 35 | 2 | .125 | 60 | 60 | 60 | 50 | 60 | 30 |
| 36 | 2 | .125 | 40 | 30 | 50 | 60 | 60 | 30 |
| 37 | 2 | .125 | 60 | 100 | 100 | 100 | 30 | 80 |
| 38 | 2 | .125 | 50 | 60 | 90 | 80 | 60 | 70 |
| 39 | 2 | .125 | 50 | 60 | 100 | 90 | 60 | 100 |
| 67 | 2 | .1 | 40 | 50 | 40 | 40 | 70 | 60 |
| 68 | 2 | .1 | 30 | 60 | 60 | 30 | 60 | 60 |
| 69 | 2 | .1 | 70 | 60 | 50 | 50 | 60 | 70 |
| 71 | 2 | .1 | 60 | 30 | 0 | 10 | 30 | 40 |
| 72 | 2 | .1 | 50 | 20 | 50 | 40 | 40 | 40 |
| 73 | 2 | .125 | 70 | 100 | 80 | 40 | 90 | 50 |
| 74 | 2 | .125 | 70 | 90 | 60 | 50 | 0 | 80 |
| 75 | 2 | .125 | 60 | 60 | 60 | 70 | 0 | 50 |

What is claimed is:

1. A compound of formula (I):

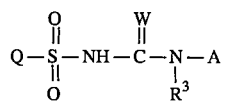

wherein

Q is Q-1, Q-2 or Q-3 are:

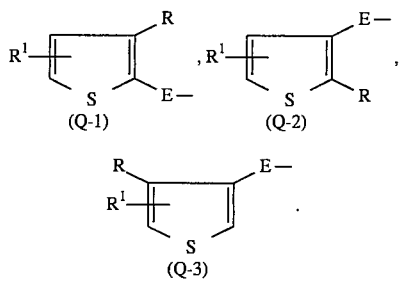

wherein $R^1$ is H, $C_1$-$C_3$ alkyl, $C_1$-$C_3$ haloalkyl, halogen, CN, $NO_2$, $C_1$-$C_3$ alkoxy, $C_1$-$C_3$ haloalkoxy, $SO_2NR'R''$, $C_1$-$C_3$ alkylthio, $C_1$-$C_3$ alkylsulfinyl, $C_1$-$C_3$ alkylsulfonyl, $SCHF_2$, $NH_2$, $NHCH_3$, $N(Me)_2$, $C_1$-$C_2$ alkyl substituted with $C_1$-$C_2$ alkoxy, $C_1$-$C_2$ haloalkoxy, SH, $SCH_3$, CN or OH; or $CO_2R'''$; wherein $R'$ is H, $C_1$-$C_4$ alkyl, $C_2$-$C_3$ cyanoalkyl, methoxy or ethoxy; $R''$ is H, $C_1$-$C_4$ alkyl, $C_3$-$C_4$ alkenyl, or when taken together connecting $R'$ and $R''$, —$(CH_2)_3$—, $(CH_2)_4$—, —$(CH_2)_5$— or $CH_2CH_2OCH_2CH_2$—, may be formed; $R_{III}$ is $C_1$-$C_4$ alkyl, $C_3$-$C_4$ alkenyl, $C_3$-$C_4$ alkynyl, $C_1$-$C_4$ alkyl substituted with 1-3 halogens or cyano groups, $C_5$-$C_6$ cycloalkyl, $C_4$-$C_7$ cycloalkylalkyl or $C_2$-$C_4$ alkoxyalkyl;

R is

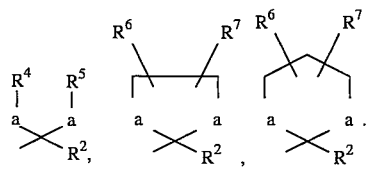

wherein, a is O or S; $R^2$ is $C_1$-$C_6$ alkyl substituted with 1-3 halogens; $R^4$ and $R^5$ are respectively $C_1$-$C_4$ alkyl; and $R_6$ and $R_7$ are respectively H, $C_1$-$C_3$ alkyl or $C_1$-$C_3$ haloalkyl;

E is $CH_2$ or single bond;

$R^3$ is H or $CH_3$;

W is O or S;

A is

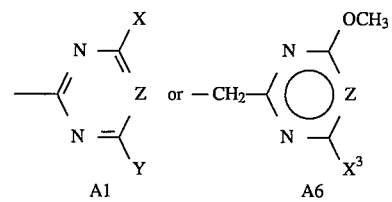

wherein,

X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, halogen, $C_2$-$C_5$ alkoxyalkyl, $C_2$-$C_5$ alkoxylalkoxy, amino, $C_1$–$C_3$ alkylamino, di($C_1$–$C_3$ alkyl) amino or $C_3$–$C_5$ cycloalkyl;

Y is H, $C_1$–$C_4$ alkyl, $C_1$–$C_4$ alkoxy, $C_1$–$C_4$ haloalkoxy, $C_1$–$C_4$ haloalkylthio, $C_1$–$C_4$ alkylthio, $C_2$–$C_5$ alkoxyalkyl, $C_1$–$C_5$ alkoxyalkoxy, amino, $C_1$–$C_3$ alkylamino, di($C_1$–$C_3$ alkyl) amino, $C_3$–$C_4$ alkenyloxy, $C_3$–$C_4$ alkynyloxy, $C_2$–$C_5$ alkylthioalkyl, $C_1$–$C_4$ haloalkyl, $C_2$–$C_4$ alkynyl, azido, cyano, $C_2$–$C_5$ alkylsulfinylalkyl, $C_2$–$C_5$ alkylsulfonylalkyl $CH_2OH$, $C_3$–$C_5$ cycloalkyl, $C_3$–$C_5$, cycloalkoxy, $C_2$–$C_5$ alkylthioalkoxy,

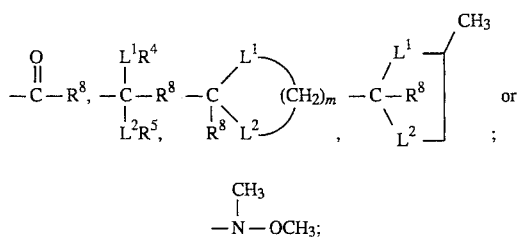 or $$-\overset{CH_3}{\underset{|}{N}}-OCH_3;$$

m is 2 or 3;

$L^1$ and $L^2$ are independently O or S;

$R^4$ and $R^5$ are independently $C_1$–$C_2$ alkyl;

$R^6$ is H or $CH_3$;

Z is N;

$X^3$ is $CH_3$ or $OCH_3$;

or agriculturally suitable salts thereof.

2. A compound as defined in claim 1, wherein W is O; E is single bond; and $R^3$ is H.

3. A compound as defined in claim 1, wherein $R^1$ is selected from the group consisting of H, halogen, $C_1$–$C_2$ alkyl, $C_1$–$C_2$ alkoxy, $C_1$–$C_2$ haloalkyl, $C_1$–$C_2$ alkylthio, haloalkoxy and $CH_2CN$; X is selected from the group consisting of $C_1$–$C_2$ alkyl, $C_1$–$C_2$ alkoxy, Cl, F, Br, I, $OCHF_2$, $CH_2F$, $CF_3$, $OCH_2CH_2F$, $OCH_2CHF_2$, $OCH_2CF_3$, $CH_2Cl$ and $CH_2Br$; and Y is H, $C_1$–$C_2$ alkyl, $C_1$–$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2\equiv CH$, $OCH_2CH_2OCH_3$, $CH_2SCH_3$,

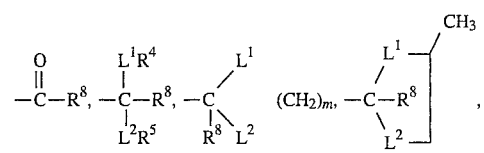

$OCHF_2$, $OCF_2Br$, $SCHF_2$, cyclopropyl, $C\equiv CH$ or $C\equiv C-CH_3$, and then $R^4$ and $R^5$ and $C_1$–$C_2$ alkyl, $R^8$ is H or $CH_3$, $L^1$ and $L^2$ are O or S, and m is 2 or 3.

4. A compound as defined in claim 1, wherein A is $A_1$; X is $CH_3$, $C_2H_5$, $OCH_3$, $OCH_{2CH3}$, Cl or $OCHF_2$; and Y is $CH_3$, $OCH_3$, $OC_2H_5$, $C_2H_5$, $CH_2OCH_3$, $NHCH_3$, $CH(OCH_3)_2$ or cyclopropyl.

5. A compound as defined in claim 1, wherein $R^2$ is $CH_2F$, $CH_2CH_2F$, $CHFCH_3$, $CH_2Cl$, $CH_2Br$, $CHCl_2$, $CHFCl$, $CH_2CHCl$, $CHClCH_3$, $CHF_2$, $CHClCH_2Cl$, $CHFCH_2Cl$, $CHFCH_2F$ or $CH_2CHF_2$.

6. A compound as defined in claim 1, wherein said general formula(I) is 3-(2-fluoromethyl-1,3-dioxalan-2-yl)-N-[(4-methoxy-6-methyltriazin-2-yl)aminocarbonyl]4-thiophene-sulfonamide.

7. A compound as defined in claim 1, wherein said general formula(I) is N-[ (4,6-dimethoxytriazin-2-yl)aminocarbonyl]-3-(2-fluoromethyl-1,3-dioxalan- 2-yl)-4-thiophene-sulfonamide.

8. A compound as defined in claim 1, wherein said general formula (I) is 2-(2-fluoromethyl-1,3-dioxalan-2-yl)-N-[(4-methoxy-6-methyltriazin-2-yl)aminocarbonyl]- 3-thiophene-sulfonamide.

9. A compound as defined in claim 1, wherein said general formula(I) is N-[( 4,6-dimethoxytriazin-2-yl)aminocarbonyl]-2-(2-fluoromethyl-1,3-oxalan- 2-yl)-3-thiophene-sulfonamide.

10. An herbicidal composition comprising one or more compounds of formula (I) of claim 1 in combination with an inert carrier.

11. A method of controlling weeds comprising applying an effective amount of one or more compounds of formula (I) of claim 1 to a weedy area.

* * * * *